United States Patent
Ando et al.

(10) Patent No.: US 7,964,732 B2
(45) Date of Patent: Jun. 21, 2011

(54) SUBSTITUTED BICYCLOCARBOXYAMIDE COMPOUNDS

(75) Inventors: Koji Ando, Chita-gun (JP); Andrew Anthony Calabrese, Sandwich (GB); Matthew Alexander James Duncton, San Francisco, CA (US); Kentaro Futatsugi, Chita-gun (JP); Misato Hirano, Chita-gun (JP); Satochi Nagayama, San Francisco, CA (US)

(73) Assignee: Pfizer Inc., New York, NY (US)

( * ) Notice: Subject to any disclaimer, the term of this patent is extended or adjusted under 35 U.S.C. 154(b) by 54 days.

(21) Appl. No.: 12/063,159

(22) PCT Filed: Nov. 9, 2007

(86) PCT No.: PCT/IB2007/003559
§ 371 (c)(1),
(2), (4) Date: May 19, 2008

(87) PCT Pub. No.: WO2008/059370
PCT Pub. Date: May 22, 2008

(65) Prior Publication Data
US 2010/0267769 A1    Oct. 21, 2010

Related U.S. Application Data

(60) Provisional application No. 60/866,285, filed on Nov. 17, 2006, provisional application No. 60/943,933, filed on Jun. 14, 2007, provisional application No. 60/983,343, filed on Oct. 29, 2007.

(51) Int. Cl.
| A61P 25/00 | (2006.01) |
| A61P 29/00 | (2006.01) |
| A61P 11/00 | (2006.01) |
| A61P 1/00  | (2006.01) |

(52) U.S. Cl. ...... 546/169; 514/314; 514/406; 548/375.1
(58) Field of Classification Search .................. None
See application file for complete search history.

(56) References Cited

U.S. PATENT DOCUMENTS

| 5,580,983 | A  | 12/1996 | Kraus .................... 546/336 |
| 6,774,136 | B2 | 8/2004  | Gerlach et al. ............. 514/319 |
| 6,979,686 | B1 | 12/2005 | Naraian et al. ............ 514/235.8 |
| 7,084,176 | B2 | 8/2006  | Morie et al. ................ 514/563 |
| 7,425,641 | B2 | 9/2008  | Ries et al. .................. 548/530 |
| 2003/0232818 | A1 | 12/2003 | Anderson et al. .......... 514/228.2 |
| 2004/0102449 | A1 | 5/2004  | Wu et al. .................. 514/252.1 |
| 2005/0009812 | A1 | 1/2005  | Seko et al. ................ 514/221 |
| 2005/0020644 | A1 | 1/2005  | Bisaha et al. .............. 514/355 |
| 2005/0165032 | A1 | 7/2005  | Norman et al. ........... 514/264.11 |
| 2005/0165046 | A1 | 7/2005  | Hulme et al. .............. 514/301 |
| 2005/0165049 | A1 | 7/2005  | Hulme et al. .............. 514/310 |
| 2006/0183909 | A1 | 8/2006  | Schmitt et al. ............. 546/158 |
| 2007/0105943 | A1 | 5/2007  | Nakamoto et al. .......... 514/430 |

FOREIGN PATENT DOCUMENTS

| DE | 4423353 | 1/1996 |
| EP | 0492178 | 7/1992 |
| EP | 0719760 | 9/1999 |
| FR | 2827599 | 1/2003 |
| GB | 2389580 | 12/2003 |
| WO | WO 9403432 | 2/1994 |
| WO | WO 9509159 | 4/1995 |
| WO | WO 9631475 | 10/1996 |
| WO | WO 9924442 | 5/1999 |
| WO | WO 9926927 | 6/1999 |
| WO | WO 0042026 | 7/2000 |
| WO | WO 0042213 | 7/2000 |
| WO | WO 0064888 | 11/2000 |
| WO | WO 0071512 | 11/2000 |
| WO | WO 0073283 | 12/2000 |
| WO | WO 0076970 | 12/2000 |
| WO | WO 0076971 | 12/2000 |
| WO | WO 0110823 | 2/2001 |
| WO | WO 0147866 | 7/2001 |
| WO | WO 0200651 | 1/2002 |
| WO | WO 0216318 | 2/2002 |
| WO | WO 0234718 | 5/2002 |
| WO | WO 02080928 | 10/2002 |
| WO | WO 02085908 | 10/2002 |

(Continued)

OTHER PUBLICATIONS

Vippagunta et al., Crystalline Solids, 48 Adv. Drug Delivery Rev. 3-26 (2001).*
Simon Frantz, The Trouble with Making Combination Drugs, 5 Nature Rev. 881-82 (2006).*
Siu, et al., Organic & Biomolecular Chemistry (2005), 3(17). pp. 3140-3160 (XP002478714).
Kariya, et al., Neuroscience Letters, vol. 392, pp. 2132-215 (2006).
Maeda, et al., Biol. Pharm. Bull., vol. 28(5), pp. 649-853 (2005).
Ding, et al., J. Med. Chem. vol. 48, p. 3171-3181 (2005).
Maeda, et al., Biorganic & Medicinal Chemistry, vol. 12, pp. 4351-4360 (2004).

(Continued)

Primary Examiner — Janet Andres
Assistant Examiner — Timothy R Rozof
(74) Attorney, Agent, or Firm — Jennifer Kispert; A. Dean Olson

(57) ABSTRACT

This invention provides a compound of the formula (I)

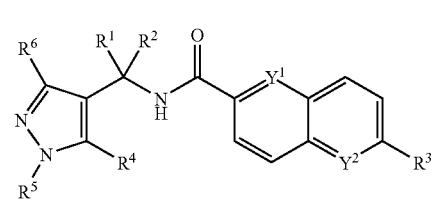

These compounds are useful for the treatment of disease conditions caused by overactivation of the VR1 receptor such as pain, or the like in mammal. This invention also provides a pharmaceutical composition comprising the above compound.

12 Claims, No Drawings

FOREIGN PATENT DOCUMENTS

| | | |
|---|---|---|
| WO | WO 02100819 | 12/2002 |
| WO | WO 03014064 | 2/2003 |
| WO | WO 03029210 | 4/2003 |
| WO | WO 03030937 | 4/2003 |
| WO | WO 03035621 | 5/2003 |
| WO | WO 03045920 | 6/2003 |
| WO | WO 03068749 | 8/2003 |
| WO | WO 03080578 | 10/2003 |
| WO | WO 03080596 | 10/2003 |
| WO | WO 03086377 | 10/2003 |
| WO | WO 03104178 | 12/2003 |
| WO | WO 2004019933 | 3/2004 |
| WO | WO 2004047743 | 6/2004 |
| WO | WO 2004052370 | 6/2004 |
| WO | WO 2004058164 | 7/2004 |
| WO | WO 2004058176 | 7/2004 |
| WO | WO 2004069792 | 8/2004 |
| WO | WO 2004078114 | 9/2004 |
| WO | WO 2004080463 | 9/2004 |
| WO | WO 2004104018 | 12/2004 |
| WO | WO 2004108133 | 12/2004 |
| WO | WO 2004113331 | 12/2004 |
| WO | WO 2005003084 | 1/2005 |
| WO | WO 2005009962 | 2/2005 |
| WO | WO 2005021509 | 3/2005 |
| WO | WO 2005021553 | 3/2005 |
| WO | WO 2005033079 | 4/2005 |
| WO | WO 2005035526 | 4/2005 |
| WO | WO 2005087742 | 9/2005 |
| WO | WO 2005105760 | 11/2005 |
| WO | WO 2006016548 | 2/2006 |

OTHER PUBLICATIONS

Halder, et al., Science of Synthesis, vol. 16(9), pp. 251-313 (2004).
Uesato, et al., Bioorganic & Medicinal Chemistry Letters. vol. 12, pp. 1347-1349 (2002).
Buolamwini, et al., J. Med. Chem. vol. 45, pp. 841-852 (2002).
Marsilje, et al., Bioorganic & Medicinal Chemistry Letters, vol. 20, pp. 477-481 (2000).
Stanczak, et al., Pharmazie, vol. 53(3), pp. 156-161 (1998).
Burke, et al., J. Med. Chem., vol. 38, pp. 4171-4178 (1995).
Burke, et al., Bioorganic & Medicinal Chemistry Letters, vol. 2(12), pp. 1772-1774 (1992).
Lanza, et al., J. Med. Chem., vol. 35, pp. 252-258 (1992).
El-Kerdawy, et al., J. Pharmaceutical Sciences, vol. 73(11), pp. 1652-1653 (1984).
Nair, et al., J. Org. Chem., vol. 38(12). pp. 2185-2189 (1973).

* cited by examiner

US 7,964,732 B2

SUBSTITUTED BICYCLOCARBOXYAMIDE COMPOUNDS

CROSS REFERENCE TO RELATED APPLICATIONS

This is a 35 U.S.C. §371 National Phase filing from PCT/IB07/003,559, filed Nov. 9, 2007, which claims priority to U.S. Provisional Application Ser. No. 60/866,285, filed Nov. 17, 2006, U.S. Provisional Application Ser. No. 60/943,933 filed Jun. 14, 2007 and U.S. Provisional Application Ser. No. 60/983,343, filed Oct. 29, 2007, the contents of each of which are incorporated by reference herein in their entirety.

TECHNICAL FIELD

This invention relates to novel substituted bicyclocarboxamide compounds and to their use in therapy. These compounds are particularly useful as modulators of the VR1 (Type I Vanilloid) receptor, and are thus useful for the treatment of diseases such as pain, neuralgia, neuropathies, nerve injury, burns, migraine, carpal tunnel syndrome, fibromyalgia, neuritis, sciatica, pelvic hypersensitivity, bladder disease, inflammation, or the like in mammals, especially humans. The present invention also relates to a pharmaceutical composition comprising the above compounds.

BACKGROUND ART

The Vanilloid receptor 1 (VR1) is a ligand gated non-selective cation channel. It is believed to be a member of the transient receptor potential super family. VR1 is recognized as a polymodal nociceptor that integrates multiple pain stimuli, e.g., noxious heat, protons, and vanilloids (European Journal of Physiology 451:151-159, 2005). A major distribution of VR1 is in the sensory (Aδ- and C-) fibres, which are bipolar neurons having somata in sensory ganglia. The peripheral fibres of these neurons innervate the skin, the mucosal membranes, and almost all internal organs. It is also recognized that VR1 exists in bladder, kidney, brain, pancreas, and various kinds of organs. A body of studies using VR1 agonists, e.g., capsaicin or resiniferatoxin, has suggested that VR1 positive nerves are thought to participate in a variety of physiological responses, including nociception (Clinical Therapeutics. 13(3): 338-395, 1991, Journal of Pharmacology and Experimental Therapeutics 314:410-421, 2005, and Neuroscience Letter 388: 75-80, 2005). Based on both the tissue distribution and the roles of VR1, VR1 antagonists would have good therapeutic potential.

WO2005070929 discloses heterocyclic amine derivatives as vanilloid receptor ligands. WO2005070885 discloses amide derivatives useful as vanilloid receptor ligands. WO2005003084 discusses 4-(methylsulfonylamino)phenyl analogues which are stated to have activity as VR1 antagonists. WO 2004069792 discloses quinoline-derived amide derivatives useful for prevention or treatment of e.g. inflammatory pain, burning pain, chronic obstructive pulmonary disease and osteoarthritis, are vanilloid receptor 1 modulators. WO 2003080578 discloses heteroaromatic urea derivatives are vanilloid-1 receptor modulators used for treating diseases and conditions in which pain and/or inflammation predominates. WO 2003068749 discloses quinoline or iso-quinoline carboxamide derivatives useful as antagonist of the vanilloid receptor (VR1). WO 2003014064 discloses amide derivatives useful as vanilloid receptor 1 antagonists. WO 2002100819 discloses N-arylphenylacetamide derivatives as vanilloid receptor VR1 antagonists for e.g. treating pain, mania and allergic rhinitis. WO2006051378 discloses a variety of N-sulfonylaminobenzyl-2-phenoxy amide derivatives as modulator of the vanilloid receptor. JP11080107 discloses amide compounds as bone formation promoters for use as antiosteoporotic agents. WO2005033079 discloses heterocyclic derivatives, useful for treating fungal infections. WO03035621 discloses naphthyl amide compounds as protein kinase and phosphatase inhibitors for treating e.g. diabetes, obesity and hearing loss.

It would be desirable if there were provided improved VR1 selective antagonist with enhanced binding activity with the VR1 receptor by systemic administration and with a good metabolic stability. Other potential advantages include less toxicity, good absorption, good solubility, low protein binding affinity, less drug-drug interaction, a reduced inhibitory activity at HERG channel, reduced QT prolongation and good metabolic stability.

BRIEF DISCLOSURE OF THE INVENTION

It has now been found that certain substituted carboxamide derivatives are potent VR1 antagonists with analgesic activity by systemic administration.

In one embodiment (A), the present invention provides a compound of the following formula (I):

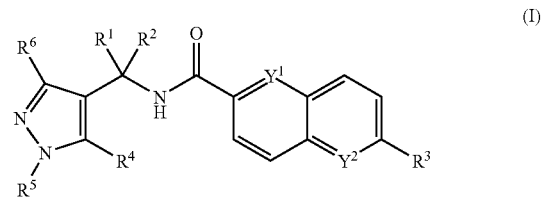

(I)

wherein
$Y^1$ and $Y^2$ are each independently N or CH; with the proviso that only one of $Y^1$ and $Y^2$ may be N;
$R^1$ and $R^2$ are each independently hydrogen, $(C_1-C_4)$alkyl, halo$(C_1-C_4)$alkyl, hydroxy$(C_1-C_4)$alkyl or $(C_1-C_2)$alkoxy $(C_1-C_2)$alkyl; or $R^1$ and $R^2$, together with the carbon atom to which they are linked, can form a cyclopropyl group;
$R^3$ is $(C_1-C_4)$alkyl, $(C_1-C_4)$alkyl-cyclopropyl, $(C_1-C_2)$alkoxy $(C_1-C_4)$alkyl or hydroxy$(C_1-C_4)$alkyl, each optionally substituted by halo or halo$(C_1-C_2)$alkyl;
$R^4$ and $R^6$ are each independently hydrogen, halo, cyano, $(C_3-C_6)$cycloalkyl, $(C_1-C_6)$alkoxy or $(C_1-C_6)$alkyl, wherein $(C_1-C_6)$alkyl is optionally substituted with one or more substituents selected from halo, amino, cyano, hydroxy, $R^7R^8NC(O)$— and $R^7OC(O)$—;
$R^5$ is hydrogen, $(C_3-C_6)$cycloalkyl, or $(C_1-C_6)$alkyl, wherein $(C_1-C_6)$alkyl is optionally substituted with one or more substituents selected from halo, amino, cyano, hydroxy, $R^7R^6NC(O)$— or $R^7OC(O)$—;
with the proviso that at least one of $R^4$, $R^5$ and $R^6$ is not hydrogen; and,
$R^7$ and $R^8$ are each independently hydrogen or $(C_1-C_4)$alkyl; or a pharmaceutically acceptable salt or solvate thereof.

Compounds of formula (I) containing one or more asymmetric carbon atoms can exist as two or more stereoisomers. Included within the scope of the present invention are all stereoisomers, geometric isomers and tautomeric forms of the compounds of formula (I), including compounds exhibiting more than one type of isomerism, and mixtures of one or more thereof. In particular, when the carbon atom to which $R^1$ and $R^2$ are attached is asymmetric, the invention includes the racemate, the (R)-enantiomer, and the (S)-enantiomer.

DETAILED DESCRIPTION OF THE INVENTION

As used herein, the term "halogen" or "halo" means fluoro, chloro, bromo or iodo, preferably fluoro or chloro.

As used herein, the term "$(C_1-C_6)$alkyl" or "$(C_1-C_4)$alkyl" mean straight or branched chain saturated radicals having the required number of carbon atoms, including, but not limited to methyl, ethyl, n-propyl, iso-propyl, n-butyl, iso-butyl, secondary-butyl, and tert-butyl groups. Preferred groups are methyl, ethyl, n-propyl, n-butyl, and tert-butyl groups.

As used herein, the term "hydroxy$(C_1-C_6)$alkyl" or "hydroxy$(C_1-C_4)$alkyl" means $(C_1-C_4)$alkyl radical as defined above which is substituted by at least one hydroxy group including, but not limited to, hydroxymethyl, hydroxyethyl, hydroxy n-propyl, hydroxy iso-propyl (e.g. 1-hydroxy-1,1-dimethylmethyl), hydroxy n-butyl, hydroxy iso-butyl, hydroxy secondary-butyl and hydroxy tert-butyl. Preferred groups are hydroxymethyl, hydroxyethyl, hydroxy n-propyl, hydroxy iso-propyl (e.g. 1-hydroxy-1,1-dimethylmethyl), hydroxy n-butyl and hydroxy tert-butyl.

As used herein, the terms "$(C_3-C_6)$cycloalkyl" means non-aromatic saturated or unsaturated hydrocarbon ring, having the required number of carbon atoms, including, but not limited to cyclopropyl, cyclobutyl, cyclopentyl and cyclohexyl groups.

As used herein the term "halo$(C_1-C_6)$alkyl" and "halo$(C_1-C_4)$alkyl" mean $(C_1-C_6)$alkyl or $(C_1-C_4)$alkyl radical which is substituted by one or more halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trifluoro-1,1-dimethylethyl, 2,2,2-trichloroethyl, 3-fluoropropyl, 4-fluorobutyl, chloromethyl, trichloromethyl, iodomethyl, bromomethyl and 4,4,4-trifluoro-3-methylbutyl groups. Preferred groups are fluoromethyl, difluoromethyl, trifluoromethyl, 2-fluoroethyl, 2,2-difluoroethyl, 2,2,2-trifluoroethyl and 2,2,2-trifluoro-1,1-dimethylethyl groups.

In a preferred embodiment (A1), $Y^1$ is CH and $Y^2$ is CH; or $Y^1$ is N and $Y^2$ is CH; or $Y^1$ is CH and $Y^2$ is N: and $R^1$-$R^8$ are each as defined herein, either in embodiment (A), or in the preferred embodiments below.

Preferably, when $Y^1$ is CH, $Y^2$ is CH and $R^1$ and $R^2$ are both hydrogen; then $R^4$ is hydrogen; $R^5$ is $C_3$-$C_6$ cycloalkyl or $(C_1-C_6)$alkyl, wherein $(C_1-C_6)$alkyl is optionally substituted with one or more substituents selected from halo, amino, cyano, hydroxy, $R^7R^8NC(O)$— or $R^7OC(O)$—; and $R^6$ is halo, cyano, $(C_3-C_6)$cycloalkyl, $(C_1-C_6)$alkoxy or $(C_1-C_6)$alkyl, wherein $(C_1-C_6)$alkyl is optionally substituted with one or more substituents selected from halo, amino, cyano, hydroxy, $R^7R^8NC(O)$— and $R^7OC(O)$—; or $R^5$ is hydrogen; and $R^4$ and $R^6$ are each independently halo, cyano, $(C_3-C_6)$cycloalkyl, $(C_1-C_6)$alkoxy or $(C_1-C_6)$alkyl, wherein $(C_1-C_6)$alkyl is optionally substituted with one or more substituents selected from halo, amino, cyano, hydroxy, $R^7R^8NC(O)$— and $R^7OC(O)$—; or $R^4$ is halo, cyano, $(C_3-C_6)$cycloalkyl, $(C_1-C_6)$alkoxy or $(C_1-C_6)$alkyl, wherein $(C_1-C_6)$alkyl is optionally substituted with one or more substituents selected from halo, amino, cyano, hydroxy, $R^7R^8NC(O)$— and $R^7OC(O)$—; $R^5$ is $(C_3-C_6)$cycloalkyl or $(C_1-C_6)$alkyl, wherein $(C_1-C_6)$alkyl is optionally substituted with one or more substituents selected from halo, amino, cyano, hydroxy, $R^7R^8NC(O)$— or $R^7OC(O)$—; and $R^6$ is hydrogen;

and $R^1$, $R^2$, $R^3$, $R^7$ and $R^8$ are as defined above in embodiment (A).

In a preferred embodiment (A2), $R^1$ and $R^2$ are each independently hydrogen, or $(C_1-C_2)$alkyl, wherein $(C_1-C_2)$alkyl is optionally substituted with one or more halo atoms; more preferably, $R^1$ is hydrogen, ethyl or methyl, wherein methyl and ethyl are optionally substituted with one or more fluoro atoms, and $R^2$ is hydrogen; and $Y^1$ and $Y^2$ are as defined in embodiments (A) and (A1) and $R^3$-$R^8$ are each as defined herein, either in embodiment (A), or in the preferred embodiments below.

In a preferred embodiment (A3), $R^3$ is 1-methylcylopropyl or $R^3$ is $(C_1-C_4)$alkyl, $(C_1-C_2)$alkoxy$(C_1-C_4)$alkyl or hydroxy$(C_1-C_4)$alkyl, each optionally substituted by halo or halo$(C_1-C_2)$alkyl; more preferably, $R^3$ is 1-methylcylopropyl, isopropyl, tert-butyl, trifluoromethyl, 1-hydroxy-1-methylethyl, 2,2,2-trifluoro-1-hydroxy-1-methyl-ethyl, 2,2,2-trifluoro-1-methoxy-1-methylethyl or 2,2,2-trifluoro-1,1-dimethylethyl; more preferably, $R^3$ is 1-methylcylopropyl, tert-butyl, trifluoromethyl, 2,2,2-trifluoro-1-hydroxy-1-methyl-ethyl or 2,2,2-trifluoro-1,1-dimethyl-ethyl: and $Y^1$, $Y^2R^1$ and $R^2$ are as defined above in embodiments (A), (A1) and (A2) and $R^4$-$R^8$ are each as defined herein, either in embodiment (A), or in the preferred embodiments below In a preferred embodiment (A4), $R^4$ is hydrogen, halo, cyano, $(C_1-C_6)$alkoxy or $(C_1-C_6)$alkyl, wherein $(C_1-C_6)$alkyl is optionally substituted with one or more substituents selected from halo and hydroxy; more preferably, $R^4$ is hydrogen, cyano, chloro, fluoro, hydroxymethyl, isopropyl, ethyl, methyl, or trifluoromethyl: and $Y^1$, $Y^2$ and $R^1$-$R^3$ are as defined above in embodiments (A) and (A1)-(A3) and $R^5$-$R^8$ are each as defined herein, either in embodiment (A), or in the preferred embodiments below.

In a preferred embodiment (A5), $R^5$ is hydrogen, cyclopropyl, cyclobutyl or $(C_1-C_4)$alkyl, wherein $(C_1-C_4)$alkyl is optionally substituted with one or more substituents selected from halo, amino, cyano, hydroxy, $R^7R^6NC(O)$— and $R^7OC(O)$; more preferably $R^5$ is hydrogen, cyclopropyl, cyclobutyl or $(C_1-C_4)$alkyl, wherein $(C_1-C_4)$alkyl is optionally substituted with one or more substituents selected from fluoro, amino, $(CH_3)_2NC(O)$—, $(CH_3)NHC(O)$—, $H_2NC(O)$—, $CH_3OC(O)$—, cyano or hydroxy; more preferably, $R^5$ is hydrogen, cyclopropyl, cyclobutyl, methyl, ethyl, isopropyl, trifluoromethyl, methoxyoxomethyl, 2-(dimethylamino)-2-oxoethyl, 2-(methylamino)-2-oxoethyl, 1-(2-amino)-2-oxoethyl, cyanomethyl, 2-amino-2-methylpropyl, 2-aminoethyl, 2-aminopropyl, 2-hydroxy-2-methylpropyl, hydroxyethyl, hydroxymethyl or 2,2,2,-trifluoroethyl: and $Y^1$, $Y^2$ and $R^1$-$R^4$ are as defined above in embodiments (A) and (A1)-(A4) and $R^6$-$R^8$ are each as defined herein, either in embodiment (A), or in the preferred embodiments below In a preferred embodiment (A6), $R^6$ is hydrogen or $(C_1-C_6)$alkyl; more preferably $R^6$ is hydrogen or $(C_1-C_4)$alkyl; more preferably $R^6$ is hydrogen or methyl: and $Y^1$, $Y^2$ and $R^1$-$R^5$ are as defined above in embodiments (A) and (A1)-(A5) and $R^7$-$R^8$ are each as defined herein, either in embodiment (A), or in the preferred embodiments below.

In a preferred embodiment (A7), $R^7$ and $R^8$ are each independently hydrogen or methyl; and $Y^1$, $Y^2$ and $R^1$-$R^6$ as defined above in embodiments (A) and (A1))-(A6).

As an alternative embodiment (A8), the invention provides a compound of formula (I), wherein $Y^1$ and $Y^2$ are each independently N or CH; with the proviso that only one of $Y^1$ and $Y^2$ is N; $R^1$ and $R^2$ are each independently hydrogen, $(C_1-C_4)$ alkyl or halo $(C_1-C_4)$ alkyl; or $R^1$ and $R^2$, together with the carbon atom to which they are linked, can form a cyclopropyl group; $R^4$, $R^5$ and $R^6$ are each independently hydrogen, $(C_1$-

C$_4$)alkyl or hydroxy(C$_1$-C$_4$) alkyl; with the proviso that at least one of R$^4$, R$^5$ and R$^6$ is not hydrogen; and, R$^3$ is (C$_1$-C$_4$) alkyl, (C$_1$-C$_4$)alkyl-cyclopropyl or 2,2,2-trifluoro-1,1-dimethyl-ethyl; or a pharmaceutically acceptable salt or solvate thereof.

As an alternative embodiment (A9), the invention provides a compound of formula (I), wherein Y$^1$ and Y$^2$ are each independently N or CH; with the proviso that only one of Y$^1$ and Y$^2$ is N; R$^1$ and R$^2$ are each independently hydrogen, (C$_1$-C$_4$) alkyl or halo (C$_1$-C$_4$) alkyl; or R$^1$ and R$^2$, together with the carbon atom to which they are linked, can form a cyclopropyl group; R$^4$, R$^5$ and R$^6$ are each independently hydrogen, (C$_1$-C$_6$)alkyl, halo (C$_1$-C$_6$) alkyl, cyano, (C$_3$-C$_6$)cycloalkyl or hydroxy(C$_1$-C$_6$) alkyl with the proviso that at least one of R$^4$, R$^5$ and R$^6$ is not hydrogen; and, R$^3$ is (C$_1$-C$_4$)alkyl, (C$_1$-C$_4$) alkyl-cyclopropyl, hydroxy (C$_1$-C$_4$) alkyl optionally substituted by halo or halo (C$_1$-C$_4$) alkyl; or a pharmaceutically acceptable salt or solvate thereof.

Specific preferred compounds of the invention are those listed in the Examples section below, and the pharmaceutically acceptable salts and solvates thereof.

The compounds of formula (I), being VR1 antagonists, are potentially useful in the treatment of a range of disorders, particularly the treatment of pain, including chronic pain, acute pain, nociceptive pain, neuropathic pain, inflammatory pain, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain and menstrual pain; bladder disease, such as urinary incontinence, lower urinary tract symptoms, micturition disorder, renal colic and cystitis; inflammation, such as burns, rheumatoid arthritis and osteoarthritis; neurodegenerative disease, such as stroke, post stroke pain and multiple sclerosis; diseases of the respiratory tree that have a contribution to symptons or pathology arising from the sensory afferent nervous system, such as cough, bronchoconstriction, irritation, inflammation and other pathways in diseases of the lower airway such as asthma and COPD as well as those of the upper airway, such as allergic rhinitis and chronic sinusitis; gastrointestinal disorders, such as gastroesophageal reflux disease (GERD), dysphagia, ulcer, irritable bowel syndrome (IBS), inflammatory bowel disease (IBD), colitis and Crohn's disease; ischemia, such as cerebrovascular ischemia and acute cerebral ischemia; emesis, such as cancer chemotherapy-induced emesis; diabetes and obesity; or the like in mammals, especially humans. The treatment of pain, particularly inflammatory pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain includes functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

Urinary incontinence (any condition in which there is an involuntary leakage of urine), includes stress urinary incontinence, urge urinary incontinence and mixed urinary incontinence, overactive bladder with associated urinary incontinence, enuresis, nocturnal enuresis, continuous urinary incontinence, and situational urinary incontinence such as incontinence during sexual intercourse.

Lower urinary tract symptoms comprise three groups of urinary symptoms, which may be defined as storage (irritative), voiding (obstructive) and post-micturition symptoms. Storage symptoms comprise urgency, frequency, nocturia, urgency incontinence and stress incontinence, which can be associated with overactive bladder (OAB) and benign prostatic hyperplasia (BPH). Voiding symptoms comprise hesitancy, poor flow, intermittency, straining and dysuria. Post-micturition symptoms comprise terminal dribbling, post-void dribbling and a sense of incomplete emptying.

Over Active Bladder (OAB) is defined as urgency, with or without urge incontinence, usually with frequency and nocturia [Abrams et al., Neurourology and Urodynamics 21:167-178 (2002)]. Prevalence of OAB in men and women is similar, with approximately 16% of the population of the USA suffering from the condition [Stewart et al, Prevalence of Overactive Bladder in the United States: Results from the NOBLE Program; Abstract Presented at the $2^{nd}$ International Consultation on Incontinence, July 2001, Paris, France]. OAB includes OAB Wet and OAB Dry. The terms OAB Wet and OAB Dry describe OAB patients with or without urinary incontinence, respectively. Until recently, the cardinal symptom of OAB was believed to be urinary incontinence. However, with the advent of the new terms this is clearly not meaningful for the large number of sufferers who are not incontinent (i.e. OAB Dry patients). Thus, a recent study from Liberman et al ['Health Related Quality of Life Among Adults with Symptoms of Overactive Bladder: Results From A US Community-Based Survey'; Urology 57(6), 1044-1050, 2001] examined the impact of all OAB symptoms on the quality of life of a community-based sample of the US population. This study demonstrated that individuals suffering from OAB without any demonstrable loss of urine have an impaired quality of life when compared with controls.

BPH is a chronically progressive disease that can lead to complications such as acute urinary retention, recurrent urinary tract infections, bladder stones and renal dysfunction. The prevalence and average severity of LUTS associated with BPH in men increases with age. BPH leads to an increase in prostate volume, creating urethral and bladder outflow obstruction as well as secondary changes in bladder function. The effects of this are manifested by both storage (irritative) and voiding (obstructive) symptoms.

The present invention provides a pharmaceutical composition including a compound of formula (I), or a pharmaceutically acceptable salt or solvate thereof, together with a pharmaceutically acceptable excipient. The composition is preferably useful for the treatment of the disease conditions defined above.

The present invention further provides a compound of formula (I), or a pharmaceutically acceptable salt or solvate thereof, for use as a medicament.

The present invention further provides a compound of formula (I), or a pharmaceutically acceptable salt or solvate thereof, for use in the treatment of the disease conditions defined above.

Further, the present invention provides a method for the treatment of the disease conditions defined above in a mammal, preferably a human, which includes administering to said mammal a therapeutically effective amount of a compound of formula (I), or a pharmaceutically acceptable salt or solvate thereof.

Yet further, the present invention provides the use of a compound of formula (I), or a pharmaceutically acceptable salt or solvate thereof, in the manufacture of a medicament for the treatment of the disease conditions defined above.

Yet further, the present invention provides a combination of a compound of the formula (I), or a pharmaceutically acceptable salt or solvate thereof, and another pharmacologically active agent.

In this specification, especially in "General Synthesis" and "Examples", the following abbreviations can be used:

| | |
|---|---|
| BEP | 2-bromo-1-ethylpyridinium tetrafluoroborate |
| BOP | benzotriazol-1-yloxy-tris(dimethylamino)phosphonium hexafluorophosphate |
| CDI | 2-chloro-1,3-dimethylimidazolinium chloride |
| DCC | dicyclohexylcarbodiimide |
| DCM | dichloromethane |
| DME | 1,2-dimethoxyethane, dimethoxyethane |
| DMF | N,N-dimethylformamide |
| DMSO | dimethyl sulfoxide |
| EDC | 1-ethyl-3-(3'-dimethylaminopropyl)carbodiimide hydrogen chloride |
| Et | ethyl |
| Et$_2$O | diethylether |
| EtOAc | ethyl acetate |
| EtOH | ethanol |
| HBTU | 2-(1H-benzenotriasol-1-yl)-1,1,3,3-tetramethyluronium hexafluorophosphate |
| HOBt | 1-hydroxybenzotriazole |
| Me | methyl |
| MeOH | methanol |
| NMP | N-methyl-2-pyrroliidone |
| T3P | 1-propylphosphonic acid cyclic anhydride |
| THF | tetrahydrofuran |
| TFA | trifluoroacetic acid |

General Synthesis

The compounds of the present invention may be prepared by a variety of processes well known for the preparation of compounds of this type, for example as shown in the following reaction Schemes.

All starting materials in the following general syntheses may be commercially available or obtained by conventional methods known to those skilled in the art.

Scheme 1:

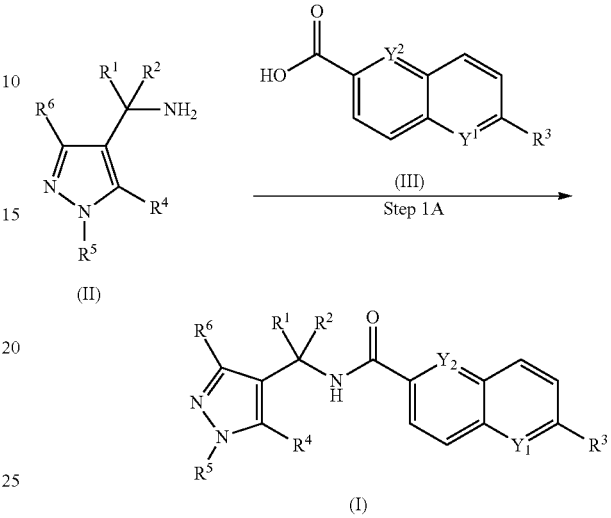

This illustrates the preparation of compounds of formula (I).

Step 1A: In this Step, amide compounds of formula (I) can be prepared by the coupling reaction of an amine compound of formula (II) with the acid compound of formula (III) in the presence or absence of a coupling reagent in an inert solvent. Suitable coupling reagents are those typically used in peptide synthesis including, for example, diimides (e.g., DCC, EDC, 2-ethoxy-N-ethoxycarbonyl-1,2-dihydroquinoline, BEP, CDI, BOP, diethyl azodicarboxylate-triphenylphosphine, diethylcyanophosphate, diethylphosphorylazide, 2-chloro-1-methylpyridinium iodide, N,N'-carbonyldiimidazole, benzotriazole-1-yl diethyl phosphate, ethyl chloroformate or isobutyl chloroformate. The reaction can be carried out in the presence of a base such as HOBt, N,N-diisopropylethylamine, N-methylmorpholine or triethylamine. The amide compound of formula (I) can be formed via an acylhalide, which can be obtained by the reaction with halogenating agents such as oxalylchloride, phosphorus oxychloride or thionyl chloride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone; nitromethane; DMF; NMP; sulfolane; DMSO; 2-butanone; acetonitrile; halogenated hydrocarbons such as DCM, dichloroethane or chloroform; and ethers such as THF or 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from about 0° C. to 60° C. The time required for the reaction can also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice.

A compound of formula (II) can be prepared from a compound of formula (IV), as illustrated by schemes 2 and 2'.

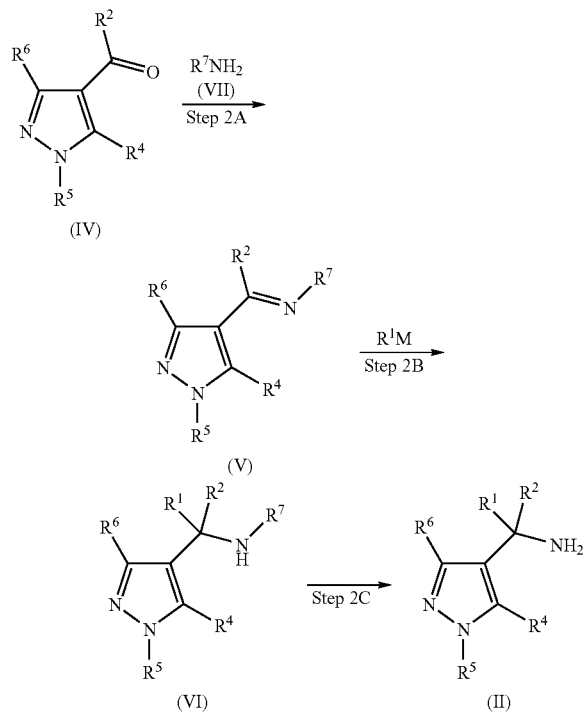

wherein $R^7$ is tert-butylsulfinyl, hydrogen, benzyl or diphenylmethyl; and

M is a suitable metal, such as lithium; or MgZ, wherein Z is halogen.

Step 2A: In the above formula, a compound formula (V) can be prepared by coupling reaction of the compound of formula (IV) with the amine of formula (VII) with dehydrating reagent and/or HCl-MeOH and/or Lewis Acid. A preferred dehydrating reagent includes sodium sulfate, magnesium sulfate, calcium sulfate or methylformate. Examples of Lewis acid include: titanium(IV) ethoxide; titanium(IV) isopropoxide; or titanium(IV) chloride. Examples of suitable solvents include: THF; 1,4-dioxane; DMF; acetonitrile; alcohols such as MeOH or EtOH; halogenated hydrocarbons such as DCM, 1,2-dichloroethane, chloroform or carbon tetrachloride; or acetic acid. Reaction temperature is generally in the range of 0 to 200° C., preferably in the range of from 100° C. to 140° C. Reaction time is, in general, from 1 minute to a day, preferably from 5 minutes to 1 hour. If necessary, microwave condition is applied to the reaction.

Step 2B: When $R^1$ is alkyl group, the compound of formula (VI) can be prepared by reaction of the compound of formula (V) with an appropriate organometallic reagent $R^1M$. $R^1M$ can be prepared by reaction of a halide compound of $R^1$. For example, $R^1M$, in which M represents MgZ, can be generated with stirring Mg and $R^1Z$, dibromoethane and $I_2$ under warming condition from the range of between 30-80° C. This reaction may be carried out in the presence of an organometallic reagent or a metal. Examples of suitable organometallic reagents include alkyllithiums such as n-butyllithium, sec-butyllithium or tert-butyllithium; aryllithiums such as phenyllithium or lithium naphthalenide. Examples of suitable metal include magnesium. If necessary, various metal salts such as cerium, copper, iron, nickel, or zinc, and/or Lewis acidic additive such as trimethylaluminum, boron trifluoride diethylether complex, can be employed to facilitate this reaction. Preferred inert solvents include, for example, hydrocarbons, such as hexane or benzene; halogenated hydrocarbons such as DCM; ethers, such as diethyl ether, diisopropyl ether, DME, THF or 1,4-dioxane; or mixtures thereof. Reaction temperature is generally in the range of −100 to 50° C., preferably in the range of from −100° C. to room temperature. Reaction time is, in general, from 1 minute to a day, preferably from 1 hour to 10 hours.

When $R^1$ is hydrogen, the compound of formula (VI) can be prepared by reaction of the compound of formula (V) with a reducing agent such as diborane, borane-methyl sulfide complex, sodium borohydride, lithium borohydride, L-selectride, Super-Hydride or lithium aluminum hydride in an inert solvent selected from THF, diethyl ether or 1,4-dioxane. This reduction may also be carried out under known hydrogenation conditions such as in the presence of a metal catalyst such as Raney nickel catalysts in the presence or absence of hydrazine, palladium catalysts or platinum catalysts under hydrogen atmosphere. This reaction may be carried out in an inert solvent such as MeOH, EtOH, and THF in the presence or absence of hydrogen chloride. If necessary, this reduction may be carried out under the adequate pressure in the range from about 0.5 to 10 kg/cm², preferably in the range from 1 to 6 kg/cm².

Step 2C: In this Step, the compound of the formula (II) can be prepared by deprotection and/or salt formation of the compound of formula (VI) under acidic condition in an inert solvent using a method of Journal of American Chemical Society, 1999, 121, 268-269 by By D. Cogan et. al. An acid includes, for example, but not limited to hydrogen chloride, hydrogen bromide, trifluoromethane sulfonic acid, acetic acid or p-toluenesulfonic acid. The reaction may be also carried out under known hydrogenation conditions such as in the presence of a metal catalyst such as palladium-carbon catalyst or platinum catalysts under hydrogen atmosphere. This reaction may be carried out in an inert solvent such as MeOH, EtOH, and THF in the presence or absence of hydrogen chloride. If necessary, this reduction may be carried out under the adequate pressure in the range from about 0.5 to 10 kg/cm², preferably in the range from 1 to 6 kg/cm². Reaction temperature is generally in the range of −100° C. to 250° C., preferably in the range of 0° C. to the reflux temperature, but if necessary, lower or higher temperature can be employed. Reaction time is, in general, from 1 minute to 2 days, preferably from 20 minutes to 24 hours.

Scheme 2'

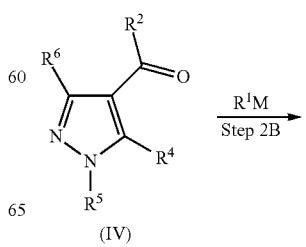

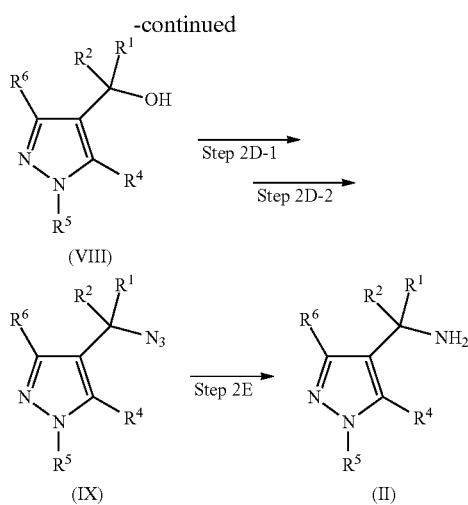

Step 2D-1: In this Step, a compound of formula (VIII) may be converted to a compound with a leaving group under conditions known to those skilled in the art. For example, the hydroxy group of the compound of formula (VIII) may be converted to chloride using a chlorinating agent, e.g. thionyl chloride, oxalyl chloride in the presence or absence of an inert solvent, e.g. halogenated hydrocarbons such as methylene chloride, chloroform, carbon tetrachloride or 1,2-dichloroethane; or ethers such as diethyl ether, diisopropyl ether, THF or 1,4-dioxane; DMF or DMSO. The hydroxy group of the compound of formula (VIII) may also be converted to the sulfonate group using a sulfonating agent, e.g. para-toluenesulfonyl chloride, para-toluenesulfonic anhydride, methanesulfonyl chloride, methanesulfonic anhydride, trifluoromethanesulfonic anhydride in the presence of, or absence of a base, e.g. an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of an inert solvent, e.g. aliphatic hydrocarbons, such as hexane, heptane or petroleum ether; aromatic hydrocarbons, such as benzene, toluene, o-dichlorobenzene, nitrobenzene, pyridine or xylene; halogenated hydrocarbons such as methylene chloride, chloroform, carbon tetrachloride or 1,2-dichloroethane; ethers such as diethyl ether, diisopropyl ether, THF or 1,4-dioxane; DMF or DMSO.

Step 2D-2: A compound of formula (IX) may be prepared by azide introduction. The compound obtained in the Step 2D-1 may be treated with diphenylphosphoryl azide (DPPA), sodium azide, or $HN_3$ in the presence of dialkyl azodicarboxylate such as diethyl azodicarboxylate (DEAD) and phosphine reagent such as triphenylphosphine. Preferably, this reaction may be carried out in an inert solvent. Preferred inert solvents include, but are not limited to, THF, diethyl ether, DMF, benzene, toluene, xylene, o-dichlorobenzene, nitrobenzene, DCM, 1,2-dichloroethane or DME; or mixtures thereof. Reaction temperature is generally in the range of −100 to 250° C., preferably in the range of 0° C. to the reflux temperature, but if necessary, lower or higher temperature can be employed. Reaction time is, in general, from 1 minute to a day, preferably from 20 minutes to 5 hours, however shorter or longer reaction times, if necessary, can be employed.

Step 2E: In this Step, a compound of formula (II) can be prepared by reduction of the azide compound of formula (IX) with a reducing agent. This reaction may be carried out in the presence of a suitable reducing agent such as diboran, boran-methyl sulfide complex, or lithium aluminum hydride in an inert solvent such as THF or diethyl ether. The reaction may also be carried out in similar conditions to those described in Step 2C above.

A compound of formula (IV) can be synthesized from a compound of formula (X) as illustrated by Schemes 3,3' and 3" below.

Scheme 3:

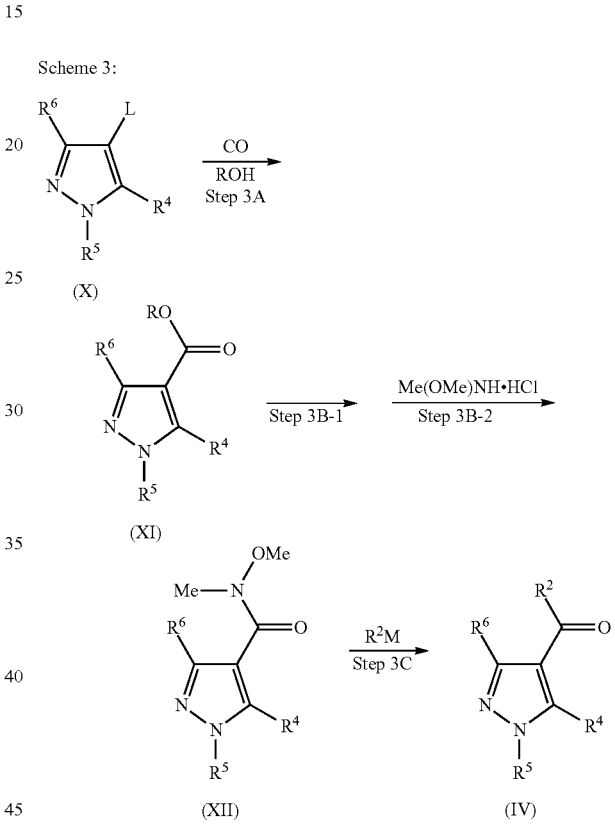

wherein L is a suitable leaving group such as O-triflate, O-tosylate or halogen;

R is $(C_1-C_6)$alkyl; and

M is a metal, such as lithium; or MgZ, wherein Z is halogen.

Step 3A: When L is a leaving group such as trifluoromethanesulfonate, tosylate, iodide, bromide, or chloride, the compound of formula (XI) can be prepared by reacting the compound of formula (X) with carbon monoxide and alcohol (e.g. MeOH or EtOH) in the presence of a catalyst and/or base in an inert solvent. Examples of suitable catalysts include: palladium reagents, such as palladium acetate or palladium dibenzylacetone. Examples of suitable bases include: N,N-diisopropylethylamine, N-methylmorpholine or triethylamine. If desired, this reaction may be carried out in the presence or absence of an additive such as 1,1'-bis(diphenylphosphino)ferrocene, triphenylphosphine or 1,3-bis-(diphenylphosphino)propane (DPPP). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone; nitromethane; DMF; sulfolane; DMSO; NMP; 2-butanone; acetonitrile; halogenated hydrocarbons such as DCM, dichloroethane or chloroform; or ethers, such as THF or 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from about 50° C. to 80° C. The time required for the reaction may also vary widely, depending on many factors, notably the reaction temperature and the nature of the reagents and solvent employed. However, provided that the reaction is effected under the preferred conditions outlined above, a period of 30 minutes to 24 hours, more preferably 1 hour to 10 hours, will usually suffice.

Step 3B-1: In this Step, an acid compound may be prepared by hydrolysis of the compound of formula (XI) in a solvent. The hydrolysis may be carried out by conventional procedures. In a typical procedure, the hydrolysis carried out under the basic condition in the presence of water, suitable bases include, for examples, sodium hydroxide, potassium hydroxide or lithium hydroxide. Suitable solvents include, for example, alcohols such as MeOH, EtOH, propanol, butanol, 2-methoxyethanol or ethylene gylcol; ethers such as THF, DME or 1,4-dioxane; amides such as DMF or hexamethylphosphorictriamide; or sulfoxides such as DMSO. This reaction may be carried out at a temperature in the range from −20 to 100° C., usually from 20° C. to 65° C. for 30 minutes to 24 hours, usually 60 minutes to 10 hours. The hydrolysis may also be carried out under an acid condition, e.g. in the presence of hydrogen halides, such as hydrogen chloride and hydrogen bromide; sulfonic acids, such as p-toluenesulfonic acid and benzenesulfonic acid; pyridium p-toluenesulfonate; and carboxylic acid, such as acetic acid and trifluoroacetic acid. Suitable solvents include, for example, alcohols such as MeOH, EtOH, propanol, butanol, 2-methoxyethanol, and ethylene gylcol; ethers such as THF, DME and 1,4-dioxane; amides such as DMF and hexamethylphosphorictriamide; and sulfoxides such as DMSO. This reaction may be carried out at a temperature in the range from −20 to 100° C., usually from 20° C. to 65° C. for 30 minutes to 24 hours, usually 60 minutes to 10 hours.

Step 3B-2: In this step, an amide compound of formula (XII) can be prepared from the product of 3B-1 by the same procedure as Step 1. Alternatively, a compound of formula (XII) can be prepared directly from the compound of formula (XI) by following the literature procedure (Tetrahedron Letters, 1995, 36, 5461-5464 by J. M. Williams et. al.).

Step 3C: When $R^2$ is alkyl group, the compound of formula (IV) can be prepared by reaction of the compound of formula (XII) with an organometallic reagent $R^2M$ as described in Step 2B.

When $R^2$ is hydrogen, the compound of formula (IV) can be prepared by reaction of the compound of formula (XII) with an appropriate reducing reagent such as DIBAL-H, lithium alunium hydride, sodium borohydride in a suitable solvent such as toluene, THF, or diethyl ether. Reaction temperature is generally in the range of −100° C. to 50° C., preferably in the range of −100° C. to room temperature. Reaction time is, in general, from 1 minute to a day, preferably from 1 hour to 10 hours.

Scheme 3′:

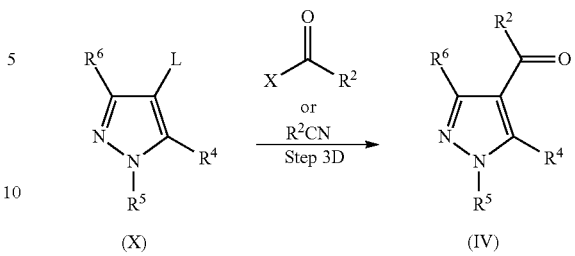

wherein L is iodide, bromide or hydrogen; and
X is halogen or N(OMe)Me.

Step 3D: When L is halogen group such as bromine or iodine, a compound of formula (IV) can be prepared by the reaction of the corresponding organometallic reagent of the compound of formula (X), generated by halogen-metal exchange reaction using an appropriate organometallic reagent, with a suitable electrophile. Suitable organometallic reagents for halogen-metal exchange include: n-butyl lithium, sec-butyl lithium, tert-butyl lithium, iso-propylmagnesium chloride with metal salt as LiBr, LiCl, or mixtures thereof. Examples of solvents for this reaction includes, but are not limited to: ethers, such as diethyl ether, diisopropyl ether, DME, THF or 1,4-dioxane; hydrocarbons, such as hexane or benzene; or the mixture of thereof. Reaction temperature is generally in the range of −100° C. to 0° C., preferably in the range of −100° C. to −10° C. Reaction time is, in general, from 1 minute to a day, preferably from 1 hour to 10 hours. When $R^2$ is an alkyl group, suitable electrophiles for this reaction include the corresponding Weinreb amide, acid halide, or nitrile compound. When $R^2$ is hydrogen, N,N-dimethylformamide (DMF) can be used as a electrophile. The reaction temperature for this stage is generally in the range of −100° C. to 90° C., preferably in the range of −100° C. to room temperature.

When L is hydrogen and $R^2$ is an alkyl group, a compound of formula (IV) can be prepared by Friedel-Crafts type reaction of the compound of formula (X) and suitable electrophile in the presence or absence of acid catalysts. Examples of electrophile for this type of reaction include, but not are limited to: acid halide or acid anhydride. Examples of suitable solvents include: halogenated hydrocarbons such as DCM, 1,2-dichloroethane, chloroform or carbon tetrachloride; or DME. This reaction can be carried out in the presence of a suitable catalyst such as aluminium(III) chloride, titanium (IV) chloride or zirconium(IV) chloride. Reaction temperature is generally in the range of −100 to 90° C., preferably in the range of from room temperature to 70° C. Reaction time is, in general, from 1 minute to a day, preferably from 1 hour to 10 hours.

When L is hydrogen and $R^2$ is hydrogen, a compound of formula (IV) can be prepared by Vilsmeier reaction of the compound of formula (X) under standard conditions (for example, DMF-POCl$_3$).

When L is hydrogen and placed in the active position for deprotonation (for example, the adjacent substituent act as a directed metalating group or L is positioned next to the hetero atom of the heteroaromatic ring) a compound of formula (IV) can be prepared by the reaction of the corresponding organometallic reagent of the compound of formula (X), generated by deprotonation reaction using an appropriate organometallic base with a suitable electrophile. Examples of organometallic base applicable for this reaction include, but are not limited to: n-butyl lithium, sec-butyl lithium, tert-butyl lithium, LDA, LHMDS, LTMP, iso-propylmagnesium chloride with metal salt as LiBr, LiCl, or the mixture of thereof. Examples of directed metalating group include, but are not limited to: trifluoromethyl, carboxamide, sulfonamide, alkoxy, halogen, carboxylic acid, ester or amide. Other detailed conditions (electrophile, solvent, reaction temperature, reaction time) is similar to that of halogen-metal exchange reaction as described in Step 3D above.

Scheme 3″:

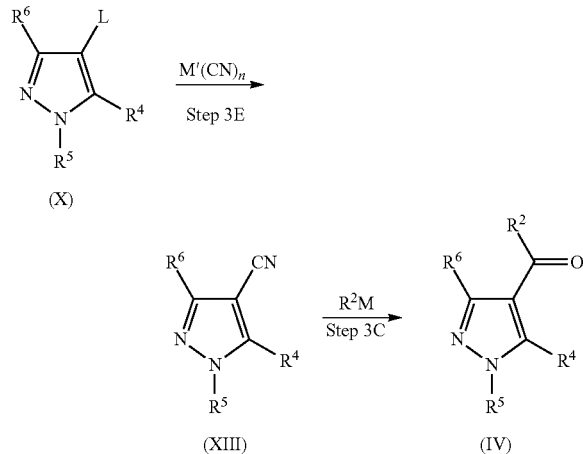

wherein L is a suitable leaving group such as trifluoromethanesulfonate, tosylate, iodide, bromide, or chloride; M is M is a metal, such as lithium; or MgZ, wherein Z is halogen; and
M' is a suitable metal.

Step 3E: A compound of formula (XIII) can be prepared by cyanating the compound of formula (X) under a cyanating condition with a transition metal catalyst and metal cyanide reagent in an inert solvent. Examples of suitable solvents include: THF; 1,4-dioxane; DMF; acetonitrile; alcohols such as MeOH or EtOH; halogenated hydrocarbons such as DCM, 1,2-dichloroethane, chloroform or carbon tetrachloride; or DME. Suitable reagents include, for example, alkalimetal cyanide such as lithium cyanide, sodium cyanide, potassium cyanide, transition metal cyanide such as ferric(II) cyanide, cobalt(II) cyanide, copper(I) cyanide, copper(II) cyanide, zinc(II) cyanide or trimethylsilyl cyanide. This reaction can be carried out in the presence of a suitable catalyst. There is likewise no particular restriction on the nature of the catalysts used, and any catalysts commonly used in reactions of this type can equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris(dibenzylideneacetone) dipalladium(0) or [1,1'-bis(diphenylphosphino)ferrocene] palladium(II) dichloride. Preferable catalysts are tetrakis (triphenylphosphine)-palladium, bis(triphenylphosphine) palladium(II) chloride, palladium(II) acetate, palladium(II) chloride, bisacetonitriledichloropalladium(0), bis(dibenzylideneacetone)palladium(0), tris(dibenzylideneacetone) dipalladium(0) or [1,1'-bis(diphenylphosphino)ferrocene] palladium(II) dichloride The reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl or triphenylarsine. The reaction can be carried out at a temperature of from 0° C. to 200° C., more preferably from 20° C. to 120° C. Reaction time is, in general, from 5 minutes to 48 hours, more preferably 30 minutes to 24 hours, will usually suffice. If necessary, microwave is applied to the reaction.

Scheme 4:

When $R^2$ is methyl, a compound of formula (IV) may be prepared from a compound of formula (X) as illustrated below.

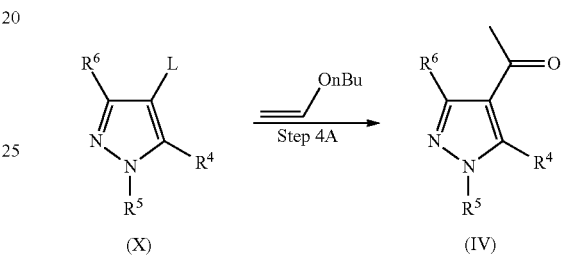

wherein L is a suitable leaving group such as trifluoromethanesulfonate, tosylate, iodide, bromide, or chloride.

Step 4A: When L is a leaving group such as and $R^2$ is methyl, a compound of formula (IV) can be prepared from the compound of formula (X) via Heck-type reaction with an appropriate transition metal catalyst, base, and additives in a solvent. Examples of suitable solvents include: protic solvents such as water, alcohols such as MeOH or EtOH and co-solvents of water or alcohols as protic solvents mixed with THF, 1,4-dioxane, DMF or acetonitrile. This reaction can be carried out in the presence of a suitable catalyst. There is likewise no particular restriction on the nature of the catalysts used, and any catalysts commonly used in reactions of this type can equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris(dibenzylideneacetone) dipalladium(0) or [1,1'-bis(diphenylphosphino)ferrocene] palladium(II) dichloride. Preferable catalysts are tetrakis (triphenylphosphine)-palladium, bis(triphenylphosphine) palladium(II) chloride, palladium(II) acetate, palladium(II) chloride, bisacetonitriledichloropalladium(0), bis(dibenzylideneacetone)palladium(0), tris(dibenzylideneacetone) dipalladium(0) or [1,1'-bis(diphenylphosphino)ferrocene] palladium(II) dichloride. This reaction can be carried out in the presence of a suitable additive agent. Examples of such additive agents include: triphenylphosphine, tri-tert-butylphosphine, 1,2-bis(diphenylphosphino)ethane, 1,3-bis (diphenylphosphino)propane, 1,1'-bis(diphenylphosphino) ferrocene, tri-2-furylphosphine, tri-o-tolylphosphine, 2-(dichlorohexylphosphino)biphenyl or triphenylarsine. This reaction can be carried out in the presence of bases such as potassium carbonate, sodium carbonate or cesium carbonate. The reaction can be carried out at a temperature of from 0° C. to 200° C., more preferably from 20° C. to 120° C. Reaction time is, in general, from 5 minutes to 48 hours, more preferably 30 minutes to 24 hours, will usually suffice. If necessary, microwave irradiation can be applied for this reaction.

Scheme 5:

A compound of formulae (IV), (XI), and (XIII) can be synthesized through pyrazole ring formation as illustrated below. This synthetic route can be regarded as an alternative method for the preparation of functionalized pyrazole derivatives.

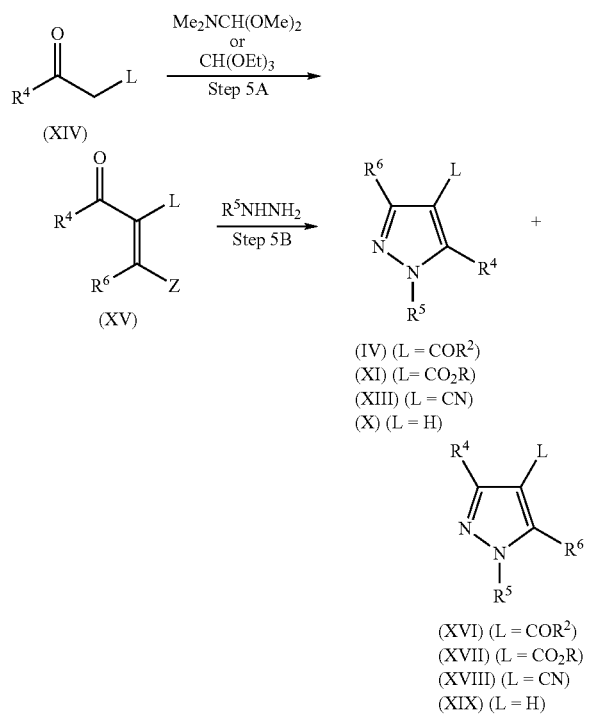

wherein L is $COR^2$, $CO_2R$, CN, or hydrogen; and Z is OEt, $NMe_2$ or OH.

Step 5A: When Z is OEt or $NMe_2$, the compound of formula (XV) can be prepared from the compound of formula (XIV) by the reaction with N,N-dimethylformamide dimethylacetal or triethylorthoformate under known standard conditions. In the case of the reaction with triethylorthoformate, the reaction can be done in acetic anhydride as solvent, while no particular additive or solvent is required for the reaction with N,N-dimethylformamide dimethylacetal. The reaction can be carried out at a temperature from 0° C. to 200° C., more preferably from 20° C. to 120° C. Reaction time is, in general, from 5 minutes to 48 hours, more preferably 30 minutes to 24 hours, will usually suffice. If necessary, microwave irradiation can be applied for this reaction.

Step 5B: The compounds of formula (IV), (XI), (X) and (XIII) can be synthesized through pyrazole ring formation with the compound of formula (XV) and the suitable hydrazine derivative under acidic or neutral condition in an appropriate solvent. This reaction may afford regioisomeric products such as the compound of formula (XVI), (XVII), (XVIII) or (XIX) in each case, and the ratio of regioisomers varies depending on the reaction conditions. Under acidic condition, protic acids such as hydrochloric acid, sulfonic acid, triflic acid, nitric acid, and p-toluenesulfonic acid can be added for this reaction. A suitable solvent includes: ethers such as diethyl ether, THF or 1,4-dioxane; alcohols such as MeOH, EtOH, or iPrOH; halogenated hydrocarbons such as DCM; or hydrocarbons such as pentane, hexane, or toluene. The reaction can be carried out at a temperature from −100° C. to 150° C., more preferably from −20° C. to 100° C. Reaction time is, in general, from 5 minutes to 48 hours, more preferably 30 minutes to 24 hours, will usually suffice.

Scheme 6:

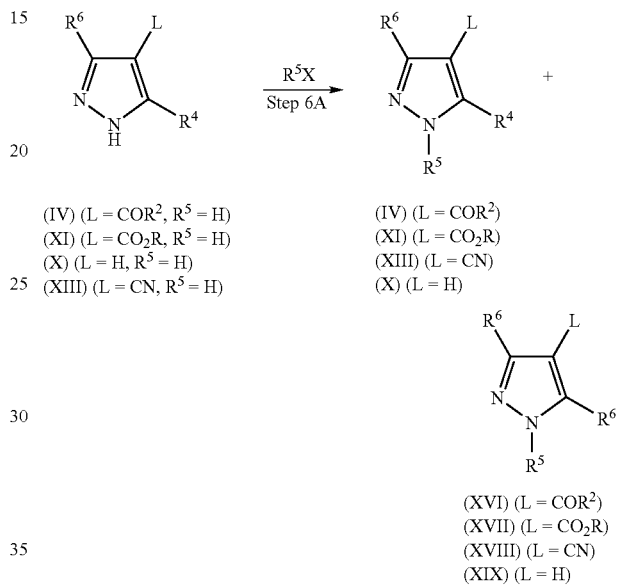

wherein X is a suitable leaving groups such as halogen, O-triflate, O-tosylate or O-mesylate.

Step 6A: The compounds of formula (IV), (XI), (X) and (XIII) can be synthesized through N-alkylation of the compounds of formula (IV), (XI), (X) and (XIII) (where $R^5$ is hydrogen) with the suitable alkylating reagent and the suitable base in an appropriate solvent, or with the corresponding alcohol under standard Mitsunobu condition in the presence of dialkyl azodicarboxylate such as diethyl azodicarboxylate (DEAD) and phosphine reagent such as triphenylphosphine. This reaction may afford regioisomeric products such as the compound of formula (XVI), (XVII), (XVIII) or (XIX) in each case, and the ratio of regioisomers varies depending on the reaction conditions. Examples of base include, but not limited to: alkali metal hydride and hydroxide, potassium carbonate. A suitable solvent includes: ethers such as diethyl ether, THF, DME or 1,4-dioxane; alcohols such as MeOH, EtOH, or iPrOH; halogenated hydrocarbons such as DCM; hydrocarbons such as pentane, hexane, or toluene; acetone; ethyl acetate; acetonitrile; DMSO; or DMF. The reaction can be carried out at a temperature from −100° C. to 150° C., more preferably from −20° C. to 100° C. Reaction time is, in general, from 5 minutes to 48 hours, more preferably 30 minutes to 24 hours, will usually suffice.

Scheme 7:

When $R^2$, $R^4$ and $R^5$ are all hydrogen, a compound of formula (IV) may be prepared as illustrated below.

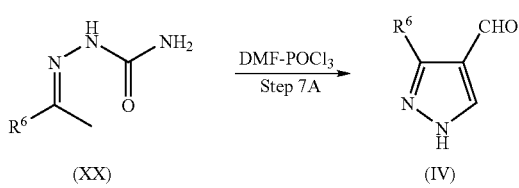

Step 7A: When $R^2$, $R^4$, and $R^5$ are all hydrogen, the compound of formula (IV) can be synthesized from the compound of formula (XX) and DMF-POCl$_3$. The reaction can be generally performed without any solvent. The reaction can be carried out at a temperature from –100° C. to 150° C., more preferably from –20° C. to 100° C. Reaction time is, in general, from 5 minutes to 48 hours, more preferably 30 minutes to 24 hours, will usually suffice.

Scheme 8:

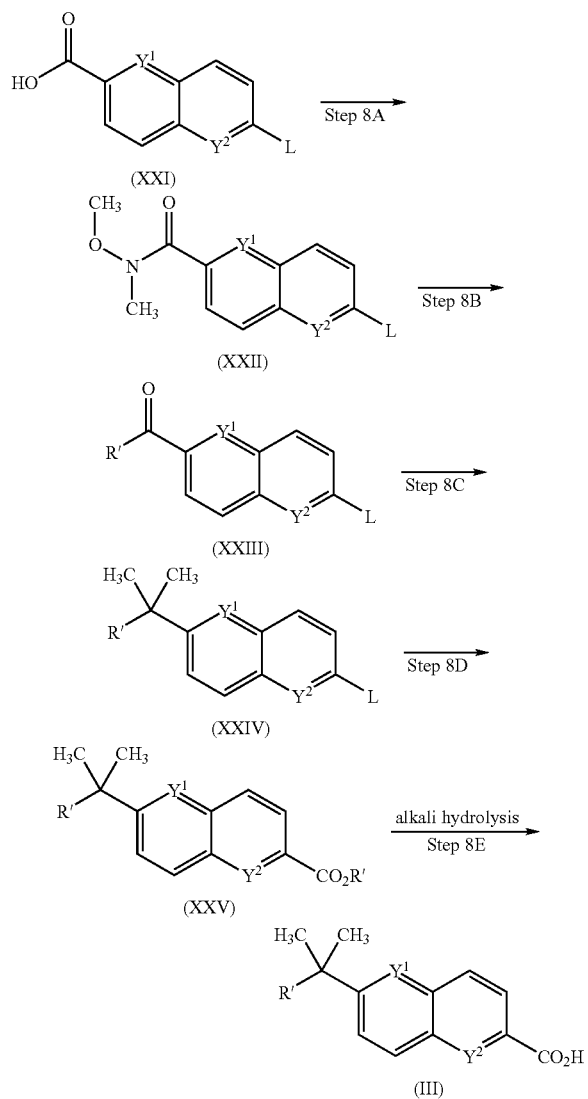

wherein R' is an optionally substituted alkyl group; and L is a suitable leaving group.

Step 8A: In this Step, an amide compound of formula (XXII) can be prepared from the compound of formula (XXI) by the same procedure as Step 1.

Step 8B: In this Step, the ketone compound of formula (XXIII) can also be prepared from the compound of formula (XXII) by the same procedure as Step 2B.

Step 8C: In this Step, a compound of formula (XXIV) can also be prepared by an alkylation reaction of the compound of formula (XXIII) with geminal-alkylating reagent in an inert solvent. Examples of preferred alkylating agents include trialkylmetals such as trimethylaluminum, triethylaluminum; alkylmagnesium halides such as methylmagnesium bromide in the presence of additive compound such as lithium bromide; dialkyltitanium halides such as dimethyltitanium dichloride prepared by dimethylzinc and titanium chloride; and is most preferably dimethyltitanium dichloride. Examples of preferred inert solvents for the reaction include halogenated hydrocarbons, such as DCM, 1,2-dichloroethane, chloroform or carbon tetrachloride; ethers, such as diethyl ether, diisopropyl ether, DME, THF and 1,4-dioxane; hydrocarbons, such as n-hexane, cyclohexane, benzene and toluene; or mixtures thereof. Reaction temperatures are generally in the range of from –100 to 200° C., preferably in the range of from –40° C. to 100° C. Reaction times are, in general, from 1 minute to a day, preferably from 1 hour to 10 hours.

Step 8D: In this Step, the compound of formula (XXV) can also be prepared from the compound of formula (XXIV) by the same procedure as Step 3A.

Step 6E: In this Step, an acid compound of formula (III) can be prepared from the compound of formula (XXV) by the same procedure as Step 3B-1 in a solvent.

Scheme 9:

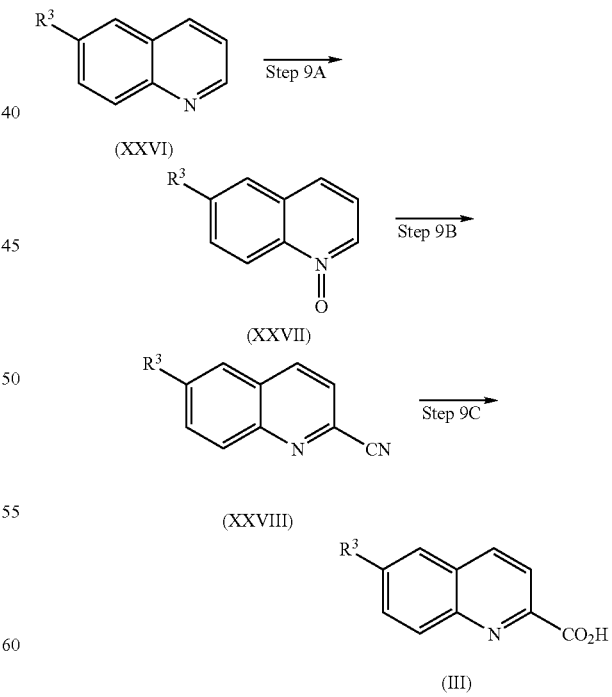

Step 9A: In this Step, a N-oxide compound of formula (XXVII) can be prepared by oxidation of the compound of formula (XXVI) in a reaction inert solvent. The oxidation reaction may be carried out in the absence or presence of an additive agent in a reaction inert solvent. Examples of preferred oxidation reagents meta-chloroperbenzoic acid (mCPBA), hydrogen peroxide, peracetic acid. Examples of preferred reaction inert solvents include halogenated hydrocarbons, such as methylene chloride, chloroform, carbon tetrachloride and dichloroethane; ethers, such as diethyl ether, diisopropyl ether, DME, THF and 1,4-dioxane; acetonitrile, acetic acid and water or mixtures thereof. Reaction temperatures are generally in the range of 0° C. to 250° C., more preferably in the range of 0° C. to 100° C. Reaction times are, in general, from 1 minute to a 10 day, more preferably from 20 minutes to 6 hours. This reaction may be carried out in the presence of a suitable catalyst. There is likewise no particular restriction on the nature of the catalyst used, and any catalyst commonly used in reactions of this type may equally be used here. Examples of such catalysts include methyltrioxorhenium(VII), tungstic acid and sodium tungstate dehydrate.

Step 9B: In this Step, a cyano compound of formula (XXVIII) can be prepared by cyanation of the compound of formula (XXVII) in a reaction inert solvent. Examples of preferred cyanation reagents include trimethylsilanecarbonitrile (TMSCN), the combination of trimethylchlorosilane and sodium cyanide, the combination of acylating agents such as N,N-dimethylcarbamoyl chloride with trimethylsilanecarbonitrile (TMSCN). A preferred cyanation reagent is trimethylsilanecarbonitrile (TMSCN) in the presence of a base such triethylamine in a reaction inert solvent. Examples of preferred reaction inert solvents include halogenated hydrocarbons, such as methylene chloride, chloroform, carbon tetrachloride and dichloroethane; ethers, such as diethyl ether, DME, THF and 1,4-dioxane; acetonitrile, DMF, DMSO or mixtures thereof. Reaction temperatures are generally in the range of 0° C. to 250° C., more preferably in the range of 0° C. to 100° C. Reaction times are, in general, from 1 minute to 10 days, more preferably from 20 minutes to 24 hours.

Step 9C: In this Step, an acid compound of formula (III) can be prepared by hydrolysis of the cyano compound of formula (XXVIII) in a solvent. The hydrolysis can be carried out by conventional procedures. In a typical procedure, the hydrolysis may be carried out under basic conditions, e.g. in the presence of sodium hydroxide, potassium hydroxide or lithium hydroxide. Examples of suitable solvents include alcohols such as MeOH, EtOH, propanol, butanol, 2-methoxyethanol, and ethylene gylcol; ethers such as THF, DME, and 1,4-dioxane; amides such as DMF and hexamethylphospholictriamide; and sulfoxides such as DMSO. Preferable solvents are MeOH, EtOH, propanol, THF, DME, 1,4-dioxane, DMF and DMSO. This reaction can be carried out at a temperature in the range from −20 to 150° C., usually from 20° C. to 100° C. for 30 minutes to 24 hours, usually 60 minutes to 10 hours.

Scheme10:

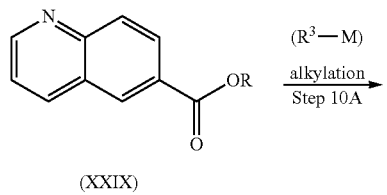

(XXIX)

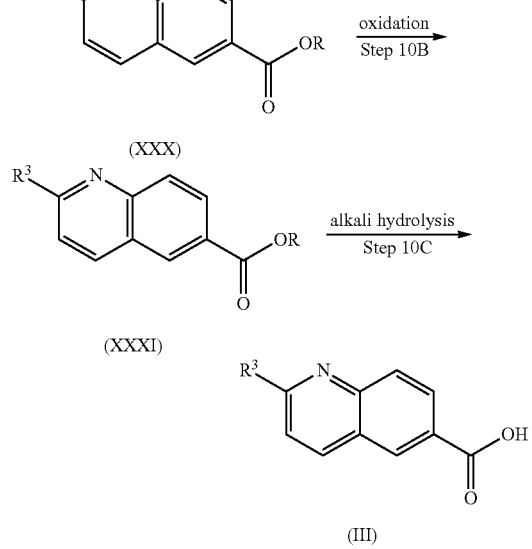

wherein R is $(C_1-C_6)$alkyl or benzyl; and
M is a suitable metal, metal hydride, or metal halide.

Step 10A: In this Step, a 1,2-dihydroquinoline compound of formula (XXX) can be prepared by alkylation of the compound of formula (XXIX) in a reaction inert solvent. The organometallic compound of formula $R^3$-M can be prepared from the corresponding alkyl halide. M represents metal such as lithium, or MgX, wherein X represents a hydrogen atom, a halogen atom such as, fluorine, chlorine, bromine or iodine. Examples of suitable organometallic reagents include alkyllithiums such as methyllithium, n-butyllithium, n-butyllithium, sec-butyllithium and tert-butyllithium; aryllithiums such as phenyllithium and lithium naphtilide; alkylmagnesium halide such as methylmagnesium halide, isopropylmagnesium halide, and t-butylmagnesium halide; arylmagnesium halide such as phenylmagnesium halide. Examples of preferred reaction inert solvents include hydrocarbons, such as hexane; ethers, such as diethyl ether, diisopropyl ether, DME, THF and 1,4-dioxane; or mixtures thereof. Reaction temperatures are generally in the range of −100 to 100° C., preferably in the range of from −100° C. to room temperature. Reaction times are, in general, from 1 minute to a day, preferably from 1 hour to 24 hours.

Step 10B: In this Step, a compound of formula (X)(XI) can be prepared by oxidation of the compound of formula (X)(X) in a solvent. Examples of suitable oxidative agents include Cr-reagents, such as chromium trioxide ($CrO_3$), potassium chromate ($K_2CrO_4$), potassium dichromate ($K_2Cr_2O_7$); Mn-reagents, such as manganese dioxide ($MnO_2$), potassium permanganate ($KMnO_4$), quinine reagents, such as 2,3,5,6,-tetrachloro-1,4-benzoquinone (p-chloranil), 2,3-dichloro-5,6-dicyano-1,4-benzoquinone (DDQ), and air oxidation. Examples of suitable solvents include THF, 1,4-dioxane, acetone, DMF, acetonitrile, halogenated hydrocarbons (e.g., DCM, dichloroethane, chloroform), water; or mixtures thereof. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° C. to 100° C., more preferably from about −60° C. to 60°

C. The time required for the reaction may also vary widely, depending on many factors, notably the reaction temperature and the nature of the reagents and solvent employed. However, provided that the reaction is effected under the preferred conditions outlined above, a period of 1 minute to 24 hours, more preferably 30 minutes to 12 hours, will usually suffice.

Step 10C: In this Step, an acid compound of formula (III) can be prepared by hydrolysis of the compound of formula (XXXI) in a solvent by the method as described in Step 3B-1.

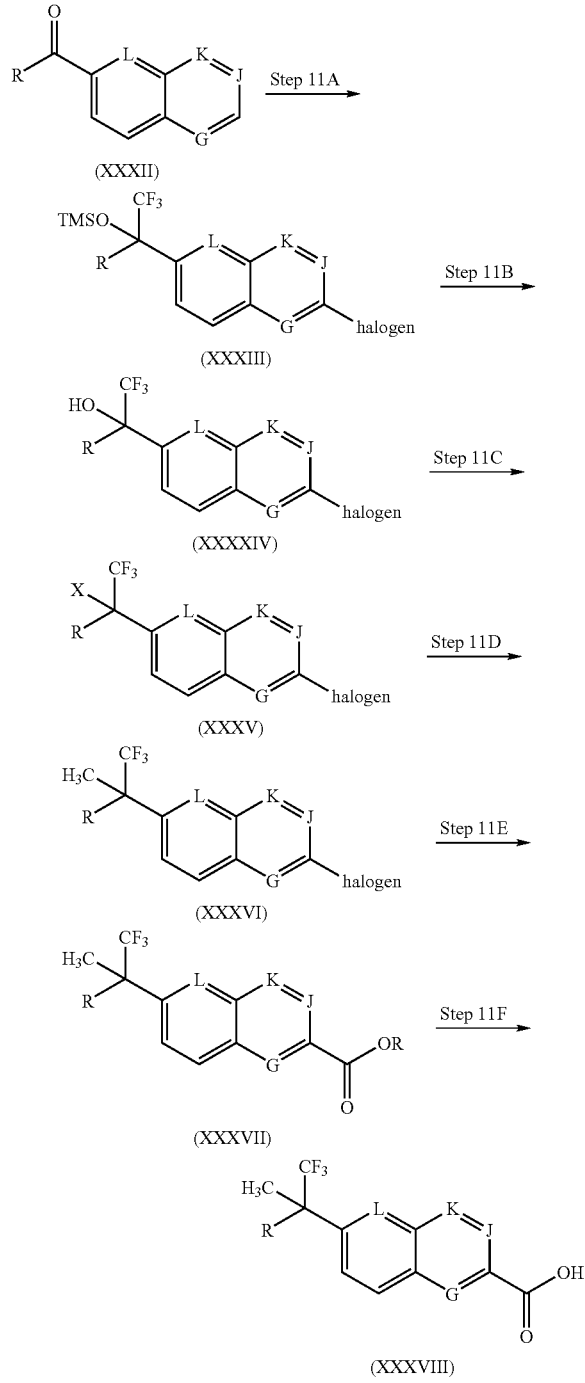

wherein X is halogen, O-mesylate, O-tosylate or O-triflate; and
R is $(C_1-C_2)$alkyl or benzyl.

Step 11A: In this Step, a compound of formula (XXXIII) can be prepared by nucleophilic trifluoromethylation of formula (XXXII) in a reaction inert solvent. Examples of preferred trifluoromethylation reagents include the combination of trifluoromethyltrimethylsilane ($TMSCF_3$) and initiator reagents. Examples of preferred catalytic initiator reagents include tetrabutylammonium fluoride (TBAF), cesium fluoride (CsF), lithium acetate (AcOLi), sodium acetate (AcONa), potassium acetate (AcOK), tetrabutylammonium acetate (AcO-nNBu$_4$), lithium pivalate (t-BuCO$_2$Li), lithium benzoate (PhCO$_2$Li), potassium t-butoxide (KO-tBu), and sodium t-butoxide (NaO-tBu). Examples of preferred reaction inert solvents include hydrocarbons, such as hexane, benzene, toluene; halogenated hydrocarbons, such as methylene chloride, chloroform, carbon tetrachloride and dichloroethane; ethers; such as diethyl ether, diisopropyl ether, 1,2-dimethoxyethane (DME), tetrahydrofuran and dioxane; acetonitrile, ethyl acetate, N,N-dimethylformamide (DMF), dimethylsulfoxide (DMSO) or mixtures thereof. Reaction temperatures are generally in the range of −78° C. to 200° C., more preferably in the range of −78° C. to 100° C. Reaction times are, in general, from 1 minute to 10 days, more preferably from 10 minutes to 24 hours.

Step 11B: In this Step, a hydroxyl compound of formula (XXXIV) can be prepared from the O-trimethylsilyl compound of formula (XXXIII) by hydrolysis under acid conditions, in a solvent, by the method as described in Step 3B-1.

Step 11C: In this Step, a compound of formula (XXXV) can be prepared by treating a compound of formula (O)XXXIV) with a suitable halogenating or O-activating agent, in a reaction inert solvent or without solvent. The halogenation reaction can be carried out under halogenating reagent in an inert solvent or without solvent. Examples of suitable solvents include tetrahydrofuran, 1,4-dioxane, N,N-dimethylformamide, acetonitrile; halogenated hydrocarbons, such as dichloromethane, 1,2-dichloroethane, chloroform or carbon tetrachloride and acetic acid. Example of suitable halogenating reagents includes thionyl chloride, oxalyl chloride, phosphorus pentachloride, phosphorus tribromide; phosphorus oxyhalide such as phosphorus oxychloride and phosphorus oxybromide; lewis acids such as titanium chloride, tin chloride and aluminium chloride. The reaction can be carried out at a temperature of from −78° C. to 200° C., more preferably from −20° C. to 150° C. Reaction times are, in general, from 5 minute to 10 days, more preferably from 30 minutes to 24 hours. The O-mesylation, O-tosylation and O-triflate reactions can be carried out by the reaction of O-activating reagents with the compound of formula (XLVII) in the presence of a base in an inert solvent or without solvent. Examples of suitable O-activation reagents include methanesulfonyl chloride, p-toluenesulfonyl chloride, trifluoromethanesulfonyl chloride and trifluoromethanesulfonic acid anhydride. Examples of suitable base include alkyl lithium such as n-butyl lithium, sec-butyl lithium and tert-butyl lithium; potassium t-butoxide and sodium t-butoxide (NaO-tBu); triethylamine, diisopropylethylamine, 4-dimethylaminopyridine and pyridine. Examples of preferred reaction inert solvents include hydrocarbons, such as hexane, benzene, toluene; halogenated hydrocarbons, such as methylene chloride, chloroform, carbon tetrachloride and dichloroethane; ethers; such as diethyl ether, diisopropyl ether, 1,2-dimethoxyethane (DME), tetrahydrofuran and dioxane; acetonitrile, N,N-dimethylformamide (DMF), dimethylsulfoxide (DMSO) or mixtures thereof. The reaction can be carried out at a temperature of from −78° C. to 150° C., more preferably from −78° C. to 100° C. Reaction times are, in general, from 5 minute to 48 days, more preferably from 30 minutes to 24 hours.

Step 11D: In this Step, a compound of formula (XXXVI) can be prepared by an alkylation reaction of the compound of formula (XXXV) with alkylating reagent in an inert solvent. Examples of preferred alkylating agents include trialkylmetals such as trimethylaluminum, triethylaluminum; alkylmagnesium halides such as methylmagnesium bromide in the presence of additive compound such as lithium bromide; dialkyltitanium halides such as dimethyltitanium dichloride prepared by dimethylzinc and titanium chloride; and most preferably trimethylaluminum. Examples of preferred inert solvents for the reaction include halogenated hydrocarbons, such as dichloromethane (DCM), 1,2-dichloroethane, chloroform or carbon tetrachloride; ethers, such as diethyl ether, diisopropyl ether, 1,2-dimethoxyethane (DME), tetrahydrofuran (THF) and 1,4-dioxane; hydrocarbons, such as n-hexane, cyclohexane, benzene and toluene; or mixtures thereof. Reaction temperatures are generally in the range of from −100° C. to 200° C., preferably in the range of from −40° C. to 100° C. Reaction times are, in general, from 1 minute to 10 days, preferably from 1 hour to 24 hours.

Step 11E: In this Step, a compound of formula (XXXVII) can be prepared by alkoxycarbonyl insertion reaction of the compound of formula (XXXVI) in a solvent by the method as described in Step 6E.

Step 11F: In this Step, an acid compound of formula (XXXVIII) can be prepared by hydrolysis of the compound of formula (XXXVII) in a solvent by the method as described in Step 3B-1.

Scheme 12

When $R^1$ is hydrogen, an amine of formula (II) may be prepared as illustrated below.

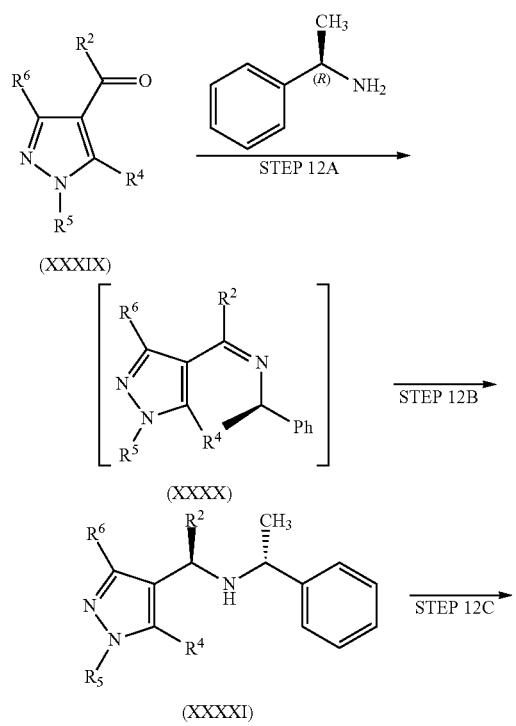

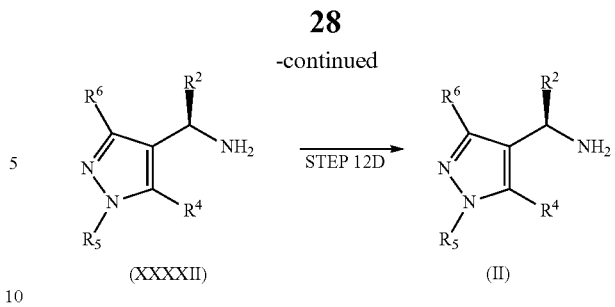

Step 12A: In this step, the compound of formula (XXXX) can be prepared by dehydration of the compound of formula (XXXIX) using a Lewis acid under basic conditions in an inert solvent. Examples of preferred Lewis acids include titanium tetrachloride, aluminium tetrachloride or zirconium tetrachloride. Examples of preferred bases include an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as triethylamine, tributylamine, diisopropylethylamine, 2,6-lutidine, pyridine or dimethylaminopyridine.

Examples of suitable solvents include THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid. Reaction temperatures are generally in the range of from −78 to 200° C., preferably in the range of from 0° C. to room temperature. Reaction times are, in general, from 1 minute to a day, preferably from 1 hour to 20 hours.

Step 12B: In this Step, the compound of formula (XXXXI) can be prepared by the reduction of the compound of formula (XXXX) in the presence of a suitable reducing agent in an inert solvent or without solvent. Examples of preferred reducing agents include $NaBH_4$, $LiAlH_4$, $LiBH_4$, Fe, Sn or Zn. Reaction temperatures are generally in the range of from −78° C. to room temperature, preferably in the range of from −70° C. to 0° C. Reaction times are, in general, from 1 minute to a day, preferably from 3 hours to 6 hours. Examples of suitable solvents include THF; 1,4-dioxane; DMF; acetonitrile; alcohols, such as methanol or ethanol; halogenated hydrocarbons, such as DCM, 1,2-dichloroethane, chloroform or carbon tetrachloride; and acetic acid.

The reduction may also be carried out in the presence of a suitable metal catalyst under a hydrogen atmosphere in an inert solvent. Example of preferred metal catalysts include nickel catalysts such as Raney nickel; Pd—C; palladiumhydroxide-carbon; platinumoxide; platinum-carbon; ruthenium-carbon; rhodium-aluminumoxide; and tris[triphenyphosphine]rhodiumchloride. Examples of suitable inert aqueous or non-aqueous organic solvents include: alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours. This reaction can be carried out under a hydrogen atmosphere at a pressure ranging from 1 to 100 atoms, preferably from 1 to 10 atoms.

Step 12C: In this step, the compounds of formula (XXXXII) can be prepared by hydrogenation of the compound of formula (X)(XXI) under, for example, known hydrogenolysis conditions in the presence of a metal catalyst under hydrogen atmosphere, or in the presence of hydrogen sources such as formic acid or ammonium formate, in an inert solvent. If desired, the reaction is carried out under acidic conditions, for example, in the presence of hydrochloric acid or acetic acid. Examples of preferred metal catalysts include nickel catalysts such as Raney nickel; Pd—C; palladiumhydroxide-carbon; platinumoxide; platinum-carbon; ruthenium-carbon; rhodium-aluminumoxide; and tris[triphenyphosphine]rhodiumchloride. Examples of suitable inert aqueous or non-aqueous organic solvents include alcohols, such as methanol or ethanol; ethers, such as THF or 1,4-dioxane; acetone; dimethylformamide; halogenated hydrocarbons, such as DCM, dichloroethane or chloroform; and acetic acid; or mixtures thereof. The reaction can be carried out at a temperature in the range of from 20° C. to 100° C., preferably in the range of from 20° C. to 60° C. Reaction times are, in general, from 10 minutes to 4 days, preferably from 30 minutes to 24 hours. This reaction can be carried out under a hydrogen atmosphere at a pressure ranging from 1 to 100 atoms, preferably from 1 to 10 atoms.

Step 12D: In this step, the compounds of formula (XXXXIII) can be prepared from the compound of formula (XXXXII) by salt formation with, for example, hydrogenchloride methanol solution, 1,4-dioxane solution and aqueous solution. The reaction can be carried out at a temperature in the range from of from 20° C. to 100° C., preferably in the range of from 20° C. to 60° C. Reaction times are, in general, from 10 minutes to 4 days, preferably from 30 minutes to 24 hours.

Scheme 13:

When $R^3$ is a fluoro alkyl group, such as trifluoromethyl or pentafluoroethyl, a carboxylic acid of formula (III) may be prepared as illustrated below.

ethylation reagent is (trifluoromethyl)trimethylsilane. The reaction is performed in the presence of a fluoride source either catalytic or stoichiometric. Examples of preferred fluoride sources are CsF, KF, tetrabutylammonium fluoride and tetraethylammonium fluoride. Examples of preferred reaction inert solvents include halogenated hydrocarbons, such as methylene chloride, chloroform, carbon tetrachloride and dichloroethane; ethers, such as diethyl ether, DME, THF and 1,4-dioxane; acetonitrile, DMF, DMSO or mixtures thereof. Reaction temperatures are generally in the range of −10° C. to 50° C., more preferably in the range of 0° C. to 25° C. Reaction times are, in general, from 1 minute to 10 days, more preferably from 20 minutes to 24 hours.

Step 13B-2: In this step, a compound of formula (III) may be prepared from the product of Step 13B-1 by hydrolysis, as described in Step 3B-1.

Step 13C: In this step, a trifluoromethyl compound of formula (XXXXV) can be prepared by trifluoromethylation of the compound of formula (XXXXIV) in a reaction inert solvent. An example of a preferred trifluoromethylation reagent is (trifluoromethyl)trimethylsilane. The reaction is performed in the presence of a base. Examples of preferred bases are potassium t-butoxide, sodium ethoxide and sodium methoxide. Examples of preferred reaction inert solvents include halogenated hydrocarbons, such as methylene chloride, chloroform, carbon tetrachloride and dichloroethane; ethers, such as diethyl ether, DME, THF and 1,4-dioxane; acetonitrile, DMF, DMSO or mixtures thereof. Reaction temperatures are generally in the range of −10° C. to 50° C., more preferably in the range of 0° C. to 25° C. Reaction times are, in general, from 1 minute to 10 days, more preferably from 20 minutes to 24 hours.

Step 13D-1: In this step, an ester derivative of the trifluoromethyl compound of formula (III) can be prepared by

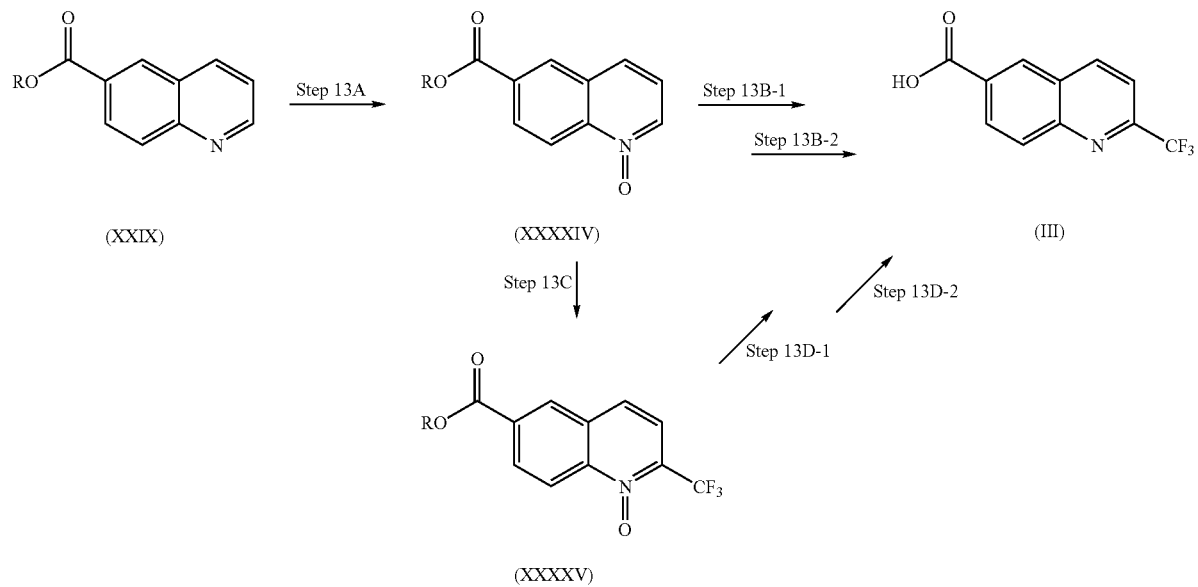

wherein R is $(C_1-C_6)$alkyl or benzyl.

Step 13A: In this step, an N-oxide compound of formula (XX)(XIV) can be prepared by oxidation of the compound of formula (XXIX) in a reaction inert solvent, as described in Step 9A.

Step 13B-1: In this step, an ester derivative of the trifluoromethyl compound of formula (III) can be prepared by trifluoromethylation of the compound of formula (XXXXIV) in a reaction inert solvent. An example of a preferred trifluoromreduction of the compound of formula (XXXXV) in a reaction inert solvent. This would typically be a hydrogenation under a pressure of 15 mmHg to 100 mmHg of hydrogen gas. Reaction temperatures are generally in the range of 20° C. to 100° C., more preferably in the range of 20° C. to 50° C. Reaction times are, in general, from 30 minutes to 3 days, more preferably from 60 minutes to 6 hours. This reaction is carried out in the presence of a suitable catalyst. There is likewise no particular restriction on the nature of the catalyst used, and any catalyst commonly used in reactions of this type may equally be used here. Examples of such catalysts include palladium on carbon, palladium hydroxide on carbon and Raney nickel.

Step 13D-2: In this step, a compound of formula (III) may be prepared from the product of Step 13D-1 by hydrolysis, as described in Step 3B-1.

Scheme 14:

When $R^2$ is hydrogen, $R^6$ is hydrogen, $R^4$ is hydroxy and $R^5$ is alkyl, a compound of formula (IV) may be prepared as illustrated below.

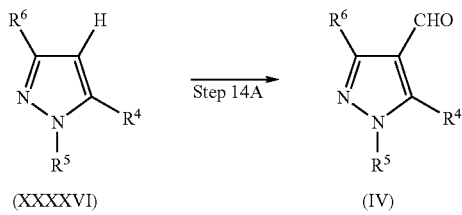

(XXXXVI)   (IV)

Step 14A: A compound of formula (IV) can be synthesized from the compound of formula (XXXXVI) and DMF-POCl$_3$. The reaction can be generally performed without any solvent. The reaction can be carried out at a temperature from −100° C. to 150° C., more preferably from −20° C. to 100° C. Reaction time is, in general, from 5 minutes to 48 hours, more preferably 30 minutes to 24 hours, will usually suffice.

Scheme 15

When $R^2$ is hydrogen, a compound of formula (IV) may be prepared as illustrated below.

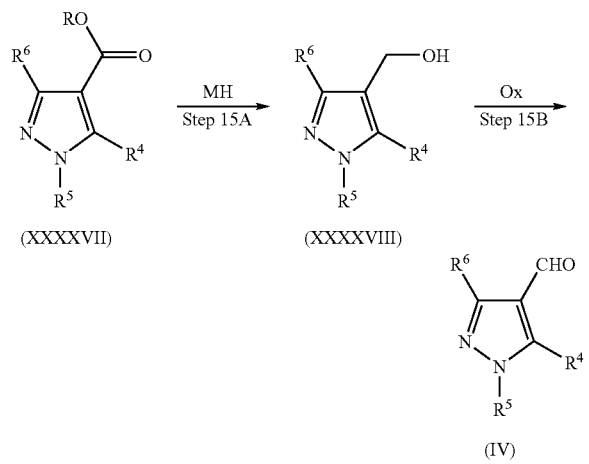

(XXXXVII)   (XXXXVIII)

(IV)

wherein MH is a suitable metal hydride reducing agent.

Step 15A: A compound of formula (XXXXVIII) can be prepared by reaction of a compound of formula (XXXXVII) with an appropriate reducing reagent such as lithium aluminium hydride, sodium borohydride or lithium borohydride in a suitable solvent such as toluene, THF, or diethyl ether. Reaction temperature is generally in the range of −100 to 100° C., preferably in the range of from 0° C. to 70° C. Reaction time is, in general, from 1 minute to a day, preferably from 2 hours to 20 hours.

Step 15B: A compound of formula (IV) can be prepared by reaction of a compound of formula (XXXXVIII) with an appropriate oxidizing agent such as "activated" DMSO reagents e.g. Swern, Dess-Martin's reagent, pyridinium chlorochromate, manganese dioxide, sodium hypochlorite and ruthenium dioxide.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

Examples

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times are given for illustration only; given melting points (mp) are uncorrected (polymorphism may result in different melting points); the structure and purity of all isolated compounds were assured by at least one of the following techniques: TLC (Merck silica gel 60 F$_{254}$ precoated TLC plates), mass spectrometry, nuclear magnetic resonance spectra (NMR), infrared red absorption spectra (IR) or microanalysis. Yields are given for illustrative purposes only. Flash column chromatography was carried out using Merck silica gel 60 (230-400 mesh ASTM) or Fuji Silysia amino bounded silica (Chromatorex, 30-50 uM) or Biotage amino bounded silica (35-75 μm, KP-NH) or Biotage silica (32-63 μm, KP-Sil). The purification using HPLC was performed by the following apparatus and conditions. Apparatus: UV-trigger preparative HPLC system, Waters (Column: XTerra MS C18, 5 um, 19×50 mm or 30×50 mm), Detector: UV 254 nm Conditions: CH$_3$CN/0.05% HCOOH aqueous solution or CH$_3$CN/0.01% NH$_3$ aqueous solution; 20 ml/min (19×50 mm) or 40 ml/min (30×50 mm) at ambient temperature. Microwave apparatus used in the reaction was Emrys optimizer (Personal chemistry). Optical rotation was measured by P-1020 (Jasco). Low-resolution mass spectral data (EI) were obtained on a Integrity (Waters) mass spectrometer. Low-resolution mass spectral data (ESI) were obtained on a ZMD (Micromass) mass spectrometer. NMR data were determined at 270 MHz (JEOL JNMLA 270 spectrometer) or 300 MHz (JEOL JNMLA300 spectrometer) using deuterated chloroform (99.8% D) or DMSO (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; by (boiling point), mp (melting point), L (liter(s)), ml (milliliter(s)), g (gram(s)), mg (milligram(s)), mol (moles), mmol (millimoles), eq. (equivalent(s)), quant. (quantitative yield), rt (room temperature), sat. (saturated), aq (aqua). In the following Examples, "Me" means methyl and "Et" means ethyl.

Preparations

The following Preparations illustrate the preparation of certain Amine and Carboxylic Acid intermediates used to prepare the Examples herein below.

Amine 1: (1,5-dimethyl-1H-pyrazol-4-yl)ethanamine Dihydrochloride

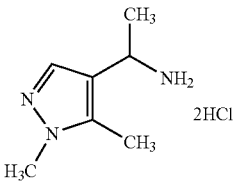

A solution of 1-(1,5-dimethyl-1H-pyrazol-4-yl)ethanone (*J. Heterocyclic Chem.* 1986, 23, 275-279, 2.17 g, 15.7 mmol, containing 14% of 1-(1,3-dimethyl-1H-pyrazol-4-yl)ethanone), (R)-(—F)-2-methyl-2-propanesulfinylamide (2.00 g, 16.5 mmol) and titanium(IV) ethoxide (9.86 ml, 47.3 mmol) in THF (5 ml) was heated at 90° C. for 3 h, then stirred under irradiation of microwave (80° C., 2 h, 90° C. 2 h), heated at 90° C. for 14 h. Then additional amount of titanium (IV) ethoxide (16.44 ml, 78.7 mmol) was added and the whole mixture was heated at 90° C. for 24 h. After being cooled to rt, the resulting mixture was added to a suspension of NaBH$_4$ (4.75 g, 126 mmol) in THF (42 mL) at 0° C., then the whole mixture was stirred for 3 h at this temperature. The reaction mixture was quenched by the addition of MeOH (8 ml) at 0° C. Celite was added to the mixture and stirred vigorously for 10 min. After that, H$_2$O (4 ml) was added and the resulting mixture was further stirred for 60 min. The resulting suspension was filtered through a celite pad, and the residue was well washed with THF. The combined filtrate was concentrated to give a dark-brown oily material. The crude material was purified by silica gel column chromatography (CH$_2$Cl$_2$: MeOH=50:1), followed by amine-gel column (CH$_2$Cl$_2$: MeOH=200:1) to give N-1-(1,5-dimethyl-1H-pyrazol-4-yl)ethyl)-2-methylpropane-2-sulfinamide as a diastereo-enriched mixture (1.26 g, 42% yield, diastereomeric ratio ca. 2:1 by $^1$H NMR). $^1$H NMR (300 MHz, CDCl$_3$) δ 1.21 (9H, s), 1.49 (3H, d, J=6.0 Hz), 2.35 (3H, s), 3.18 (1H, brs), 3.88 (3H, s), 4.44-4.52 (1H, m), 7.65 (1H, s). This compound was treated with 10 wt % HCl-MeOH (4.5 ml), and the reaction mixture was stirred for 2 h at r.t. After removal of all the volatile, the crude material was recrystallized from MeOH/ether to give 1-(1,5-dimethyl-1H-pyrazol-4-yl)ethanamine dihydrocloride as a white solid (0.44 g, 46% yield). $^1$H NMR (300 MHz, DMSO-d$_6$) δ 1.47 (3H, d, J=6.0 Hz), 2.25 (3H, s), 3.72 (3H, s), 4.21-4.28 (1H, m), 7.63 (1H, s), 8.42 (3H, brs). MS (ESI) m/z 140 (M+H)$^+$.

Amine 2: (1R)-1-(1,5-dimethyl-1H-pyrazol-4-yl)ethanamine Dihydrochloride

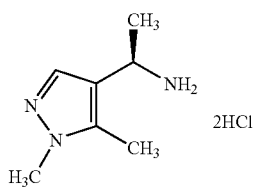

Step A2A: (1R)-1-(1,5-dimethyl-1H-pyrazol-4-yl)-N-[(1R)-1-phenylethyl]ethanamine 1-(1,5-Dimethyl-1H-pyrazol-4-yl)ethanone (*J. Heterocyclic Chem.* 1986, 23, 275-279, 4.82 g, 34.9 mmol) and (R)-1-Phenylethylamine (5.07 g, 41.9 mmol) in Titanium tetraisopropoxide (22.1 g, 77.7 mmol) were stirred at room temperature for 16 hours. Ethanol (30 ml) and THF (30 ml) were added at –20° C., then Sodium borohydride (3.96 g, 105 mmol) was added at –20° C. then the whole mixture was stirred for 3 h whilst warming to room temperature. The reaction was quenched with water (20 ml) and diluted with ethyl acetate-THF. Then the mixture was filtered through celite and washed with ethyl acetate. The filtrate was dried over Na$_2$SO$_4$, concentrated and purified by silica gel column chromatography eluted with ethyl acetate/n-Hexane=2/1 to 100/0 to furnish the title compound (3.44 g, 41% yield) as colorless oil. $^1$H NMR (270 MHz, CDCl$_3$) δ 1.26 (3H, d, J=6.6 Hz), 1.27 (3H, d, J=6.6 Hz), 1.96 (3H, s), 3.44 (1H, q, J=6.6 Hz), 3.60 (1H, q, J=6.6 Hz), 3.76 (3H, s), 7.20-7.38 (6H, m).

Step A2B: (1R)-1-(1,5-dimethyl-1H-pyrazol-4-yl)methanamine Dihydrochloride

A suspension of the compound of step A2A (3.44 g, 13.3 mmol) and 10% palladium on carbon (300 mg) in ethanol (80 ml) was stirred at 70° C. under hydrogen (1 atm) for 6 hours. After the mixture was cooled to room temperature, the catalyst was removed by filtration through celite, washed with methanol. The filtrate was concentrated to give a colorless oil. The oil was dissolved in methanol and 10% HCl-MeOH (10 ml) was added. After 30 min, the solvent was removed in vacuo and co-evaporated with toluene, ethyl acetate to furnish the title compound (2.48 g, 88% yield, >99% ee detected by HPLC; DACEL CHIRALPAK AD-H 4.6×250 mm, n-Hexane/Ethanol/Diethylamine=98/2/0.1~50/50/0.1 as eluent, less polar peak, retention time: 11.4 min) as a white solid. $^1$H NMR (270 MHz, DMSO-d$_6$) δ 1.47 (3H, d, J=6.6 Hz), 2.24 (3H, s), 3.71 (3H, s), 4.21-4.28 (1H, m), 7.51 (1H, s), 8.27 (3H, brs).

Amine 3: (R)-4-(1-aminoethyl)-1-methyl-1H-pyrazole-5-carbonitrile Dihydrochloride

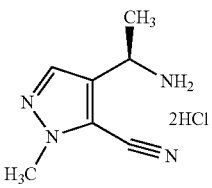

Step A3A: 5-chloro-N-methoxy-N,1-dimethyl-1H-pyrazole-4-carboxamide

To a stirred suspension of N,O-dimethylhydroxyamine hydrochloride (0.668 g, 6.85 mmol) and triethylamine (2.60 mL, 18.7 mmol) in DMF (6 mL) was added 5-chloro-1-methyl-1H-pyrazole-4-carboxylic acid (1.00 g, 6.23 mmol, purchased from Nissan Chemical) and HBTU (2.60 g, 6.85 mmol), and the resulting mixture was stirred at room temperature for 2 hours. The reaction mixture was diluted with ethyl acetate-toluene (1:1, 200 mL), washed with water (200 mL), saturated aqueous sodium bicarbonate (200 mL), water (200 mL) and brine (200 mL). The organic layer was dried over sodium sulfate, filtered and evaporated. The residue was chromatographed on a column of silica gel, using ethyl acetate-hexane (1:1) as eluent to give the title compound (1.39 g, quant.) as white solid. $^1$H NMR (270 MHz, CDCl$_3$) δ ppm 3.34 (3H, s), 3.67 (3H, s), 3.88 (3H, s), 7.93 (1H, s). MS (ESI): m/z 204 (M+H)$^+$.

Step A3B: 1-(5-chloro-1-methyl-1H-pyrazol-4-yl)ethanone

To a stirred solution of the product of Step A3A (1.39 g, 6.83 mmol) in THF (34 ml) was added methylmagnesium bromide (0.97 M in THF, 14.1 mL, 13.7 mmol) at 0° C., and the resulting mixture was stirred at room temperature for 3 hours. The reaction mixture was quenched with brine (30 mL)

and 10% aqueous solution of citric acid (10 ml), and extracted with ethyl acetate (150 ml 3 times). The combined organic layer was dried over sodium sulfate, filtered and evaporated. The residue was chromatographed on a column of silica gel eluting ethyl acetate-hexane (1:1) to give a title compound (0.98 g, 91% yield) as white solid. $^1$H NMR (270 MHz, CDCl$_3$) δ 2.48 (3H, s), 3.88 (3H, s), 7.93 (1H, s). MS (ESI): m/z 159 (M+H)$^+$.

Step A3C:
4-acetyl-1-methyl-1H-pyrazole-5-carbonitrile

A mixture of the product of Step A3B (0.96 g, 4.71 mmol) and sodium cyanide (462 mg, 9.43 mmol) in DMF (8 ml) was heated at 100° C. for 24 hours. After cooling, the reaction mixture was diluted with ethyl acetate-toluene (1:1, 100 mL), and washed with a 20% aqueous solution of sodium thiosulfate (50 mL), water (50 mL) and brine (50 mL). The organic layer was dried over sodium sulfate, filtered and evaporated. The residue was chromatographed on a column of silica gel eluting with ethyl acetate-hexane (1:1) to give the title compound (774 mg, quant.) as white solid. $^1$H NMR (270 MHz, CDCl$_3$) δ 2.54 (3 H, s), 4.11 (3H, s), 7.95 (1H, s). MS (ESI) m/z: not observed M$^+$ peak.

Step A3D (R)-N-((R)-1-(5-cyano-1-methyl-1H-pyrazol-4-yl-ethyl)-2-methylpropane-2-sulfinamide To a solution of titanium(IV) ethoxide (4.34 ml, 20.7 mmol) and the product of Step A3C (400 mg, 2.07 mmol) in THF (4.34 ml), (R)-(+)-tert-butanesulfinamide (276 mg, 2.26 mmol) was added under a nitrogen atmosphere and the mixture was heated at 80° C. for 16 hours. After cooling, the reaction mixture was added dropwise to a suspension of sodium borohydride (235 mg, 6.21 mmol) in THF (10 ml) at 0° C. over 30 minutes. The reaction mixture was stirred at room temperature for 2 hours. The resulting mixture was carefully quenched with MeOH and water, and the formed precipitate was removed by filtering through celite, washing with ethyl acetate. The organic layer was dried over sodium sulfate, concentrated, purified by silica gel eluting with ethyl acetate-hexane (4:1 to 1:0) to give the title compound as colorless oil (473 mg, 90% yield). $^1$H NMR (270 MHz, CDCl$_3$) δ 1.24 (9H, s), 1.59 (3H, d, J=6.6 Hz), 3.45 (1H, br s), 4.04 (3H, s), 4.57-4.75 (1H, m), 7.54 (1H, s). MS (ESI) m/z: 255 (M+H)$^+$.

Step A3E: (R)-4-(1-aminoethyl)-1-methyl-1H-pyrazole-5-carbonitrile Dihydrochloride A mixture of the product of Step A3D (200 mg, 0.786 mmol) in 10% hydrochloric acid ethanol solution (3 mL) was stirred at room temperature for 3 hours. The reaction mixture was evaporated and dried in vacuo to furnish the crude title compound as white solid (284 mg). This crude product was used for the next step without further purification. $^1$H NMR (270 MHz, DMSO-d$_6$) δ 1.09 (9H, s), 1.57 (3H, d, J=7.3 Hz), 4.01 (3H, s), 4.28-5.00 (3H, m), 7.96 (1H, s), 8.77 (2H, br s). MS (ESI): m/z 134 (M+H—NH$_2$)$^+$.

Amine 4: (R)-(4-(1-aminoethyl)-1-methyl-1H-pyrazol-5-yl)methanol Dihydrochloride

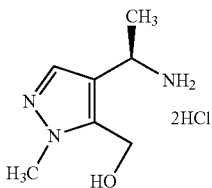

Step A4A: 1-(5-(bromomethyl)-1-methyl-1H-pyrazol-4-yl)methanone

To a stirred solution of 1-(1,5-dimethyl-1H-pyrazol-4-yl)ethanone (471 mg, 3.42 mmol) in THF (13 ml) was added N-bromosuccinimide (637 mg, 3.58 mmol) and benzoyl peroxide (41 mg, 0.17 mmol) at room temperature under nitrogen, then the resulting mixture was refluxed for 20 h. After cooling, the reaction mixture was evaporated to remove the solvents. The residue was chromatographed on a column of silica gel eluting with ethyl acetate-hexane (1:1) gave the title compound as white solid (574 mg, 78% yield). $^1$H NMR (270 MHz, CDCl$_3$) δ 2.47 (3H, s), 3.91 (3H, s), 4.87 (2H, s), 7.83 (1H, s). MS (ESI) m/z: 217 (M+H)$^+$.

Step A4B:
(4-acetyl-1-methyl-1H-pyrazol-5-yl)methyl acetate

A mixture of the product of Step A4A (574 mg, 2.64 mmol), potassium acetate (519 mg, 5.29 mmol), 18-crown-6 (140 mg, 0.529 mmol) and acetonitrile (11 ml) was stirred at room temperature for 20 hours. After solvent was removed in vacuo, the residue was diluted with brine (50 ml) and extracted with ethyl acetate (50 ml, 3 times). The combined organic extracts were dried over sodium sulfate and concentrated. The residue was chromatographed on a column of silica gel eluting with ethyl acetate-hexane (1:1) gave the title compound as white solid (536 mg, 100% yield). $^1$H NMR (270 MHz, CDCl$_3$) δ 2.09 (3H, s), 2.47 (3H, s), 3.92 (3H, s), 5.48 (2H, s), 7.86 (1H, s). MS (ESI) m/z 197 (M+H)$^+$.

Step A4C: (R)-N-((R)-1-(5-(hydroxymethyl)-1-methyl-1H-pyrazol-4-yl)ethyl)-2-methyl propane-2-sulfinamide The title compound was prepared by the same procedure as Amine 1 to give the title compound as white solid (259 mg, 45% yield). $^1$H NMR (270 MHz, CDCl$_3$) δ 1.19 (9H, s), 1.54 (3H, d, J=7.3 Hz), 3.66 (1H, m), 3.99 (3H, s), 4.42-4.62 (2H, m), 4.83 (1H, br d, J=13.8 Hz), 5.41 (1H, dd, J=4.6 Hz, 9.2 Hz), 7.65 (1H, s). MS (ESI) m/z: not observed M$^+$ peak.

Step A4D: (R)-(4-(1-aminoethyl)-1-methyl-1H-pyrazol-5-yl)methanol Dihydrochloride The title amine was prepared by the same procedure of Amine 1 to give the title compound as white solid (133 mg, 88% yield). $^1$H NMR (300 MHz, DMSO-d$_6$) δ ppm 1.48

(3H, d, J=6.6 Hz), 3.79 (3H, s), 4.07-4.95 (6H, m), 7.53 (1H, s), 8.29 (2H, br d). MS (ESI) m/z: not observed M⁺ peak.

Amine 5:
1-(1,5-dimethyl-1H-pyrazol-4-yl)propan-1-amine
Dihydrochloride

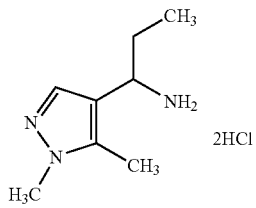

Step A5A (E)-N-((1,5-dimethyl-1H-pyrazol-4-yl)methylene)-2-methylpropane-2-sulfinamide A mixture of 1,5-dimethyl-1H-pyrazole-4-carbaldehyde (*Zhurnal Obshchei Khimii* 1980, 50, 2370-5, 2.0 g, 16.1 mmol), tert-butylsulfinamide (2.05 g, 16.9 mmol), and Ti(OEt)$_4$ (6.76 ml, 32.2 mmol) in THF (32 ml) was heated under reflux for 18 h under nitrogen. After being cooled to rt, the mixture was poured into brine (32 ml) with stirring. The resulting suspension was filtered through a plug of Celite, and the filter cake was washed with EtOAc. The filtrate was transferred to a separation funnel, and organic layer was washed with brine. Then the aqueous layer was washed with EtOAc and the combined organic extracts were dried over Na$_2$SO$_4$, and concentrated in vacuo. The crude material was purified by silica gel chromatography (CH$_2$Cl$_2$:MeOH=50:1-30:1) to give the desired product as a white solid (3.55 g, 97% yield). $^1$H NMR (300 MHz, CDCl$_3$) δ 1.23 (9H, s), 2.52 (3H, s), 3.83 (3H, s), 7.81 (1H, s), 8.49 (1H, s). MS (ESI) m/z 228 (M+H)⁺

Step A5B: N-(1-(1,5-dimethyl-1H-pyrazol-4-yl)propyl)-2-methylpropane-2-sulfinamide To a solution of (E)-N-((1,5-dimethyl-1H-pyrazol-4-yl)methylene)-2-methylpropane-2-sulfinamide (Step A5A) (600 mg, 2.64 mmol) in CH$_2$Cl$_2$ (15 ml) was added a 3.0 M solution of EtMgBr in ether (1.76 ml, 5.28 mmol) at −48° C. under nitrogen. After being stirred for 120 min, the reaction mixture was allowed to warm to rt slowly over 2 h and further stirred for 15 h at rt. The reaction was quenched by addition of sat. NH$_4$Cl aq., diluted with water, and the aqueous layer was extracted with CH$_2$Cl$_2$ 3 times. The combined organic extracts were dried over Na$_2$SO$_4$ and concentrated in vacuo. The crude product was purified by silica gel column chromatography (CH$_2$Cl$_2$: MeOH=50:1 to 20:1) to give the desired product as a pale yellow oil (650 mg, >96% yield). $^1$H NMR (270 MHz, CDCl$_3$) δ 0.87 (3H, t, J=5.4 Hz), 1.17 (9H, s), 1.77-1.85 (2H, m), 2.25 (3H, s), 3.78 (3H, s), 3.31 (1H, brs), 4.16-4.22 (1H, m), 7.31 (1H, s).

Step A5C:
1-(1,5-dimethyl-1H-pyrazol-4-yl)propan-1-amine
Dihydrochloride

N-(1-(1,5-dimethyl-1H-pyrazol-4-yl)propyl)-2-methylpropane-2-sulfinamide (Step A5B) (650 mg, 1.8 mmol) was dissolved in 10% HCl in MeOH (5 ml) and the resulting mixture was stirred for 15 h. The mixture was concentrated to give a pale yellow solid, which was recrystallized (MeOH-Ether) to give the title product as a white solid (460 mg, >99% yield). $^1$H NMR (300 MHz, DMSO-d$_6$) δ 0.76 (3H, t, J=6.0 Hz), 1.70-1.84 (1H, m), 1.89-2.03 (1H, m), 2.23 (3H, s), 3.72 (3H, s), 3.96-4.03 (1H, m), 7.54 (1H, s), 8.35 (3H, brs).

Amine 6: 1-(5-Methyl-1-(2,2,2-trifluoroethyl)-1H-pyrazol-4-yl)ethanamine Dihydrochloride

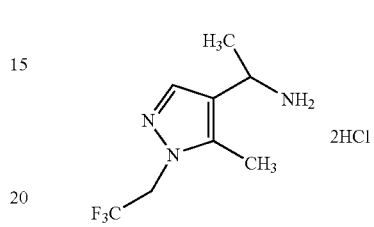

Step A6A: 1-(5-Methyl-1-(2,2,2-trifluoroethyl)-1H-pyrazol-4-yl)ethanone

To a solution of 3-(ethoxymethylene)pentane-2,4-dione (*Perkin* 1. 2000, 1455-1460, 1.95 g, 12.5 mmol) in MeOH (33 ml) was added a solution of 2,2,2-trifluoroethylhydrazine (1.54 g, 13.5 mmol) and conc.HCl (2.6 ml) in MeOH (10 ml) (pre-cooled at 0° C.) dropwise at −15° C. The resulting mixture was then stirred for 24 h at rt. After removal of the solvent at rt, the residue was basified with 2N NaOH aq, and the aqueous layer was extracted several times with EtOAc. The combined organic extracts were dried over Na$_2$SO$_4$, and concentrated in vacuo to give the crude product as a single regioisomer (1.41 g, 51% yield). $^1$H NMR (300 MHz, CDCl$_3$) δ 2.46 (3H, s), 2.62 (3H, s), 4.66 (1H, d, J=6.0 Hz), 4.72 (1H, d, J=9.0 Hz), 7.92 (1H, s). MS (ESI) m/z 207 (M+H)⁺

Step A6B: 1-(5-Methyl-1-(2,2,2-trifluoroethyl)-1H-pyrazol-4-yl)ethanamine Dihydrochloride The title compound was prepared in >99% yield by the same process as described for (R)-1-(1,5-dimethyl-1H-pyrazol-4-yl)ethanamine dihydrochloride (Amine 2) using 1-(5-methyl-1-(2,2,2-trifluoroethyl)-1H-pyrazol-4-yl)ethanone (Step A6A) as a starting material. $^1$H NMR (300 MHz, DMSO-d$_6$) δ 1.49 (3H, d, J=6.0 Hz), 2.32 (3H, s), 4.29-4.33 (1H, m), 5.07 (1H, d, J=9.0 Hz), 5.13 (1H, d, J=9.0 Hz), 7.72 (1H, s), 8.34 (3H, brs).

Amine 7: (1R)-1 (5-Methyl-1-(2,2,2-trifluoroethyl)-1H-pyrazol-4-yl)ethanamine Dihydrochloride

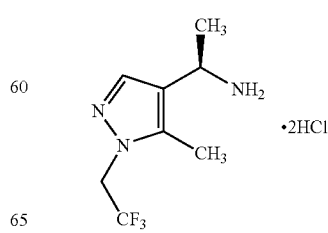

Step A7A: (1R)-1-[5-methyl-1-(2,2,2-trifluoroethyl)-1H-pyrazol-4-yl]-N-[(1R)-1-phenyl ethyl]ethanamine To a stirred solution of 1-[5-methyl-1-(2,2,2-trifluoroethyl)-1H-pyrazol-4-yl]ethanone (10.5 g, 50.7 mmol) in $CH_2Cl_2$ (150 ml) were added (R)-1-phenylethylamine (7.4 ml, 58 mmol), titanium tetrachloride (3.9 ml, 36 mmol) and $Et_3N$ (27 ml, 190 mmol) at room temperature. The reaction mixture was stirred at room temperature for 18 hours to give a solution of desired imine in $CH_2Cl_2$. Then, to this solution was added MeOH (80 ml) and the mixture was cooled to 0° C., then sodium borohydride (5.75 g, 152 mmol) was added. The reaction mixture was stirred at 0° C. for 2 hours and then quenched with saturated aqueous $NaHCO_3$ at 0° C. The mixture was extracted with AcOEt and the combined organic layers were dried over $Na_2SO_4$ and concentrated in vacuo. The residue was purified by column chromatography on silica gel (eluted with ethyl acetate/n-Hexane 2/1 to 1/1) to give the title compound (1,5-substituted product, 1.26 g, 8.0%) as a yellowish oil. The chemical structure (1,5-substitution on the pyrazole ring) was ascertained by NMR analysis (1H, $^{13}$C-1D, DEPT, COSY, HMBC, HMQC, NOESY). $^1$H NMR (300 MHz, DMSO-$d_6$) δ 1.16 (3H, d, J=6.6 Hz), 1.17 (3H, d, J=6.6 Hz), 1.88 (3H, s), 3.24-3.42 (2H, m), 4.95 (1H, d, J=8.8 Hz), 5.01 (1H, d, J=8.8 Hz), 7.16-7.24 (3H, m), 7.25-7.34 (2H, m), 7.46 (1H, s).

Step A7B: (1R)-1-(5-Methyl-1-(2,2,2-trifluoroethyl)-1H-pyrazol-4-yl)methanamine Dihydrochloride A stirred suspension of the product of Example A7A (1.46 g, 4.05 mmol) in EtOH (50 ml) was added Pd/C (100 mg) and the resulting mixture was stirred at 80° C. under $H_2$. After 5 hours, the catalyst was removed by filtration through a celite pad, washed with MeOH and the combined filtrate and washings were concentrated in vacuo. The residue was dissolved in MeOH and 10% MeOH—HCl. And then the mixture was stirred for 30 min. After further removal of Pd catalyst by filtration, the filtrate and washings were concentrated in vacuo to give the title compound (1.10 g, 97%) as a yellowish solid. $^1$H NMR (300 MHz, DMSO-$d_6$) δ 1.48 (3H, d, J=6.6 Hz), 2.31 (3H, s), 4.24-4.41 (1H, m), 5.07 (1H, d, J=9.5 Hz), 5.13 (1H, d, J=9.5 Hz), 7.70 (1H, s), 8.19-8.87 (2H, brs).

Amine 8: Methyl 2-(4-(1-aminoethyl)-5-methyl-1H-pyrazol-1-yl)acetate Dihydrochloride

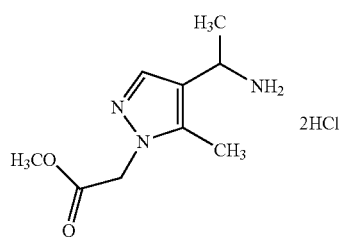

Step A8A: Methyl 2-(4-acetyl-5-methyl-1H-pyrazol-1-yl)acetate

To a solution of 3-(ethoxymethylene)pentane-2,4-dione (Perkin 1. 2000, 1455-1460, 1.95 g, 12.5 mmol) in MeOH (33 mL) was added a solution of ethyl hydrazinoacetate hydrochloride (2.09 g, 13.5 mmol) and conc.HCl (2.6 ml) in MeOH (10 ml) (pre-cooled to 0° C.) dropwise at −15° C. The resulting mixture was then stirred for 24 hours at room temperature. After removal of the solvent at room temperature, the residue was basified with 2N NaOH aq, and the aqueous layer was extracted several times with EtOAc. The combined organic extracts were dried over $Na_2SO_4$, and concentrated in vacuo. The aqueous layer was acidified to pH 1 with 2N HCl aq. and extracted with EtOAc 6 times. The combined organic extracts were dried over $Na_2SO_4$, and concentrated in vacuo to give the crude 2-(4-acetyl-5-methyl-1H-pyrazol-1-yl)acetic acid as a mixture of regioisomers (1.17 g, <51% yield). $^1$H NMR (300 MHz, DMSO-$d_6$) δ 2.37 (3H, s), 2.43 (3H, s), 4.99 (2H, s), 7.81 (1H, s), 13.2 (1H, brs).

To a solution of 2-(4-acetyl-5-methyl-1H-pyrazol-1-yl) acetic acid (1.17 g, 6.42 mmol, as a mixture of regioisomers from the previous step) in MeOH (8.8 ml)-Toluene (30.6 ml) was added a 2 M solution of (trimethylsilyl)diazomethane in ether (4.8 ml, 9.6 mmol) dropwise at 0° C. The resulting solution was allowed to warm to rt and stirred for 120 min. The reaction was quenched by addition of AcOH (3 ml) and the solvent was concentrated in vacuo. The crude product was purified by silica gel column chromatography ($CH_2Cl_2$:MeOH=30:1) to give the desired product along with a mixture of regioisomers (>99% yield). $^1$H NMR (270 MHz, CDCl$_3$) δ 2.45 (3H, s), 2.53 (3H, s), 3.79 (3H, s), 4.90 (2H, s), 7.88 (1H, s).

Step A8B: Methyl 2-(4-(1-aminoethyl)-5-methyl-1H-pyrazol-1-yl)acetate Dihydrochloride The title compound was prepared in 6.6% yield by the process as described for (R)-1-(1,5-dimethyl-1H-pyrazol-4-yl)ethanamine dihydrochloride (Amine 2) using methyl 2-(4-acetyl-5-methyl-1H-pyrazol-1-yl)acetate (Step A8A) as a starting material. $^1$H NMR (300 MHz, DMSO-$d_5$) δ 1.48 (3H, d, J=6.0 Hz), 2.22 (3H, s), 3.69 (3H, s), 4.29-4.33 (1H, m), 5.05 (2H, s), 7.59 (1H, s), 8.26 (3H, brs).

Amine 9: 1-(5-Methyl-1H-pyrazol-4-yl)ethanamine Dihydrochloride

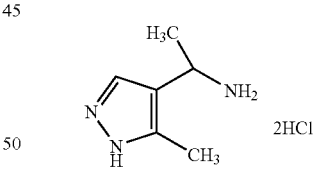

Step A9A: 5-Methyl-1H-pyrazole-4-carbaldehyde

POCl$_3$ (8.9 ml, 95.5 mmol) was added slowly to DMF (14.8 ml) under nitrogen at 0° C., and the resulting mixture was stirred for 15 min at this temperature. To this mixture was added acetone semicarbazone (5 g, 43.4 mmol) portionwise, and the reaction mixture was heated at 70° C. for 4 h. The reaction mixture was poured into ice and neutralized with 2N NaOH aq. and heated at 50-60° C. for 5 min, cooled, and acidified to pH 6 with 2N HCl aq. The solution was extracted with AcOEt 3 times and the combined organic extracts were dried over $Na_2SO_4$ and concentrated. The crude product was purified by silica gel column chromatography (Hexane:AcOEt=1:2) to give the desired product as a white solid (2.49 g, 52.1% yield). ¹H NMR (300 MHz, CDCl₃) δ 2.61 (3H, s), 8.03 (1H, s), 9.97 (1H, s). MS (ESI) m/z 109 (M−H)⁻, 111 (M+H)⁺.

Step A9B: (E)-2-methyl-N-((5-methyl-1H-pyrazol-4-yl)methylene)propane-2-sulfinamide The title compound was prepared in 85% yield by a similar method to the preparation of (E)-N-((1,5-dimethyl-1H-pyrazol-4-yl)methylene)-2-methylpropane-2-sulfinamide (Step A5A) as described above. ¹H NMR (300 MHz, CDCl₃) δ 1.24 (9H, s), 2.56 (3H, s), 7.93 (1H, s), 8.57 (1H, s).

Step A9C: 2-Methyl-N-(1-(5-methyl-1H-pyrazol-4-yl)ethyl)propane-2-sulfinamide

To a solution of (E)-2-methyl-N-((5-methyl-1H-pyrazol-4-yl)methylene)propane-2-sulfinamide (Step A9B) (2.1 g, 9.29 mmol) in THF (45 ml) was added a 1M solution of MeMgBr in THF (27.9 ml, 27.9 mmol) at −48° C. under nitrogen. After being stirred for 60 min, the reaction mixture was allowed to warm to rt and then heated at 90° C. for 4 hours.

The reaction was quenched by addition of saturated NH₄Cl aqueous solution, diluted with water, and the aqueous layer was extracted with AcOEt three times. The combined organic extracts were dried over MgSO₄ and concentrated in vacuo to give the crude material (1.43 g, 67% yield), which was used in the next reaction without any further purification. ¹H NMR (300 MHz, CDCl₃) δ 1.19 (9H, s), 1.56 (3H, d, J=9.0 Hz), 2.31 (3H, s), 3.35 (1H, brd, J=3.0 Hz), 4.50-4.54 (1H, m), 7.45 (1H, s).

Step A9D: 1-(5-Methyl-1H-pyrazol-4-yl)methanamine Dihydrochloride

The title compound was prepared in 88% yield by a similar method to the preparation of 1-(1,5-dimethyl-1H-pyrazol-4-yl)propan-1-amine dihydrochloride (Amine 5) as described above. ¹H NMR (300 MHz, DMSO-d₆) δ 1.48 (3H, d, J=6.0 Hz), 2.24 (3H, s), 4.24-4.31 (1H, m), 7.68 (1H, s), 8.23 (3H, s).

Amine 10: (S)-1-(5-chloro-1-methyl-1H-pyrazol-4-yl)ethanamine Dihydrochloride and Amine 10a: (R)-1-(5-chloro-1-methyl-1H-pyrazol-4-yl)ethanamine Dihydrochloride

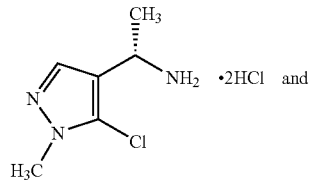 and

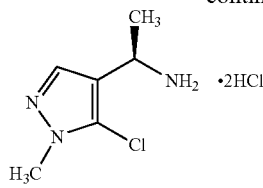

Step A10A: 1-methyl-1H-pyrazol-5-ol

3-Methoxyacrylic acid methyl ester (4 g, 34.45 mmol) was dissolved in methanol (50 ml) and cooled to 0° C. Methyl hydrazine (1.75 g, 37.9 mmol) in methanol (20 ml) was added dropwise over 30 minutes. The reaction was stirred at room temperature for 10 minutes then heated to reflux for 4 hours. The reaction was then concentrated and purified by silica gel column chromatography eluted with ethyl acetate/methanol=100/0 to 80/20 to recover the title product as a white solid (2.5 g, 73% yield). ¹H NMR (400 MHz, DMSO-d₆) δ 3.46-3.47 (3H s) 5.28-5.29 (1H d) 7.06-7.08 (1H d) 10.75-10.81 (1H bs)

Step A10B: 5-chloro-1-methyl-1H-pyrazole-4-carbaldehyde

N,N-Dimethyl formamide (2980 mg, 40.8 mmol) was added to 1-methyl-1H-pyrazol-5-ol (1000 mg, 10.19 mmol). Phosphorus oxychloride (7.46 ml, 81.5 mmol) was then added dropwise over 10 minutes. The reaction was then heated to 80° C. for 6 hours. The reaction was concentrated in vacuo and crude material neutralised with saturated aqueous NaHCO₃ solution. The product was then extracted with ethyl acetate (2×25 ml), the combined organics were washed with brine (20 ml) dried over Na₂SO₄, filtered and concentrated in vacuo to give the title product as a brown oil which formed a crystalline solid upon standing (1130 mg, 77% yield). ¹H NMR (400 MHz, CD₃OD) δ 3.84-3.87 (3H s) 7.95-7.97 (1H d) 9.76-9.78 (1H d).

Step A10C (R,E)-N-((5-chloro-1-methyl-1H-pyrazol-4-yl)methylene)-2-methylpropane-2-sulfinamide 5-chloro-1-methyl-1H-pyrazole-4-carbaldehyde (1130 mg, 7.82 mmol) was suspended in THF (20 ml), Ti(OEt)₄ (4.29 ml, 16.4 mmol) was added followed by (R)-(+)-2-methyl-2-propanesulfinamide and the reaction heated to reflux for 18 hours. The reaction was then cooled to room temperature, poured onto EtOAc:Brine (20 ml: 20 ml) filtered through celite and washed through with EtOAc (2×20 ml). The organic layer was then separated, washed with brine (20 ml), dried over Na₂SO₄, filtered and concentrated to give the title compound as a brown viscous oil (1690 mg, 87.3% yield). ¹H NMR (400 MHz, CDCl₃) δ 1.22-1.23 (9H s) 3.88 (3H s) 7.92 (1H s) 8.43 (1H br. s) MS (ESI/APCI) m/z 248 (M+H)⁺

Step A10D (R)-N-((S)-1-(5-chloro-1-methyl-1H-pyrazol-4-yl)ethyl)-2-methylpropane-2-sulfinamide (R,E)-N-((5-chloro-1-methyl-1H-pyrazol-4-yl)methylene)-2-methylpropane-2-sulfinamide (100 mg, 0.404 mmol) was dissolved in dichloromethane (10 ml) placed under nitrogen and cooled to −78° C. 1.4M methyl magnesium bromide solution (toluene:THF 3:1, 1.04 ml, 1.45 mmol) was added dropwise and reaction stirred overnight while warming to room temperature. Saturated aqueous ammonium chloride solution (20 ml) was added to the reaction and stirred for 5 minutes. The product was extracted with EtOAc (2×15 ml), combined organics were washed with brine (15 ml), dried over $Na_2SO_4$, filtered and concentrated and purified by silica gel column chromatography eluted with heptane/ethyl acetate=100/0 to 0/100 to furnish the title product as a clear gum (57 mg, 53% yield). $^1$H NMR (400 MHz, $CD_3OD$) δ 1.18-1.19 (9H s) 1.54-1.56 (3H d) 3.81-3.82 (3H s) 4.41-4.47 (1H q) 7.50-7.51 (1H s) MS (ESI) m/z 264 (M+H)$^+$

Step A10E: (S)-1-(5-chloro-1-methyl-1H-pyrazol-4-yl)ethanamine Dihydrochloride (R)-N-((S)-1-(5-chloro-1-methyl-1H-pyrazol-4-yl)ethyl)-2-methylpropane-2-sulfinamideamide (48 mg, 0.18 mmol) was dissolved in dichloromethane (5 ml), 4M HCl in dioxane (0.91 ml, 3.64 mmol) was then added and the reaction stirred at room temperature overnight. The reaction was then concentrated to give the hydrochloride salt of the title compound as a white gum (38 mg, 90% yield). NMR (400 MHz, $CD_3OD$) δ 1.60-1.63 (3H d) 3.85-3.86 (3H s) 4.39-4.45 (1H q) 7.68 (1H s) MS (ESI/APCI) m/z 160 (M+H)$^+$

Step A10F (S,E)-N-((5-chloro-1-methyl-1H-pyrazol-4-yl)methylene)-2-methylpropane-2-sulfinamide 5-chloro-1-methyl-1H-pyrazole-4-carbaldehyde (500 mg, 3.46 mmol) was suspended in THF (20 ml), $Ti(OEt)_4$ (1.51 ml, 7.26 mmol) was added followed by (S)-(+)-2-methyl-2-propanesulfinamide (440 mg, 3.63 mmol) and the reaction heated to reflux for 6 hours. The reaction was then cooled to room temperature, poured onto EtOAc:Brine (20 ml: 20 ml) filtered through celite and washed through with EtOAc (2×20 ml). The organic layer was then separated, washed with brine (20 ml), dried over $Na_2SO_4$, filtered and concentrated to give the title compound as a brown viscous oil (760 mg, 88.7% yield). $^1$H NMR (400 MHz, $CDCl_3$) δ 1.22-1.23 (9H s) 3.88 (3H s) 7.92 (1H s) 8.43 (1H br. s) MS (ESI/APCI) m/z 248 (M+H)$^+$

Step A10G (S)-N-((R)-1-(5-chloro-1-methyl-1H-pyrazol-4-yl)ethyl)-2-methylpropane-2-sulfinamide (S,E)-N-((5-chloro-1-methyl-1H-pyrazol-4-yl)methylene)-2-methylpropane-2-sulfinamide(750 mg, 3.03 mmol) was dissolved in THF (25 ml) placed under nitrogen and cooled to −78° C. 1.4M methyl magnesium bromide solution (toluene:THF 3:1, 8.65 ml, 12.1 mmol) was added dropwise and reaction stirred overnight while warming to room temperature. Saturated aqueous ammonium chloride solution (20 ml) was added to the reaction and stirred for 5 minutes. The product was extracted with EtOAc (2×15 ml), combined organics were washed with brine (15 ml), dried over $Na_2SO_4$, filtered and concentrated to furnish the title product as a brown gum (690 mg, 86.4% yield). $^1$H NMR (400 MHz, $CDCl_3$) δ 1.18-1.19 (9H s) 1.55-1.57 (3H d) 1.62-1.64 (3H s) 3.20-3.22 (1H d) 4.41-4.47 (1H q) 7.42 (1H s) MS (ESI) m/z 264 (M+H)$^+$

Step A10H: (R)-1-(5-chloro-1-methyl-1H-pyrazol-4-yl)ethanamine Dihydrochloride (S)-N-((R)-1-(5-chloro-1-methyl-1H-pyrazol-4-yl)ethyl)-2-methylpropane-2-sulfinamideamide (690 mg, 2.62 mmol) was dissolved in dichloromethane (5 ml), 4M HCl in dioxane (6.54 ml, 26.2 mmol) was then added and the reaction stirred at room temperature overnight. The reaction was then concentrated to give the hydrochloride salt of the title compound as a pale brown solid (600 mg, 98.6% yield). NMR (400 MHz, $CD_3OD$) δ 1.60-1.63 (3H d) 3.85-3.86 (3H s) 4.39-4.45 (1H q) 7.68 (1H s) MS (ESI/APCI) m/z 160 (M+H)$^+$

Amine 11: (S)-1-(1-Methyl-5-(trifluoromethyl)-1H-pyrazol-4-yl)ethanamine Dihydrochloride and

Amine 11a: (R)-1-(1-Methyl-5-(trifluoromethyl)-1H-pyrazol-4-yl)ethanamine, Dihydrochloride

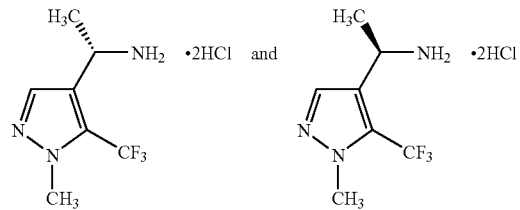

Step A11A: ethyl 1-methyl-5-(trifluoromethyl)-1H-pyrazole-4-carboxylate

Ethyl 2-(ethoxymethylene)-4,4,4-trifluoro-3-oxobutanoate (10 g, 0.042 mole) was dissolved in ethanol (120 ml) and cooled to 0° C. Methyl hydrazine (2.11 g, 0.046 mole) (pre-stirred in concentrated HCl (4 ml)-EtOH (4 ml), 0° C., 30 min) in EtOH (20 ml) was added at 0° C., and the resulting solution was stirred at room temperature for 18 h. The yellow solution was evaporated and the residue suspended in water and basified with sodium carbonate solution (saturated) and extracted with ethyl acetate (3×30 ml). The organic layer was separated and back-washed with brine (2×30 ml). The organic layer was separated, dried ($Na_2SO_4$), filtered and evaporated to give an oil. Yield 7 g. $^1$H NMR (300 MHz, $CDCl_3$) shows 6:1 for desired regioisomer. The oil was dissolved in dichloromethane and purified using an ISCO Companion (70 g silica col., heptane to ethyl acetate:heptane 1:1). The appropriate fractions were combined and evaporated to give a colourless oil, 5.71 g, Yield 62%. $^1$H NMR (400 MHz, $CDCl_3$) δ 7.91 (s, 1H) 4.36, 4.34, 4.32, 4.30 (q, 2H) 4.08 (s, 3H) 1.38, 1.36, 1.34 (t, 3H). MS (ESI): m/z 223 (M+H)$^+$. LC-MS ELSD 100% m/z 223 (M+H)$^+$. TLC Ethyl acetate: heptane 1:1 0.7 UV+ve

Step A11B: (1-methyl-5-(trifluoromethyl)-1H-pyrazol-4-yl)methanol $LiBH_4$ in THF (2M, 15 ml, 0.03 mole) was added dropwise to a stirred solution of ethyl 1-methyl-5-(trifluoromethyl)-1H-pyrazole-4-carboxylate (3.32 g, 0.015 mole) in THF (40 ml) at room temperature under nitrogen. The solution was then stirred under reflux for 18 hrs. After cooling, the cloudy solution was evaporated at room temperature to give an oil. Water was added (heavy ppt. of white solid) and the mixture chilled and treated cautiously with hydrochloric acid (2M) to pH 2 (no solid remaining, to give an oil). The mixture was neutralised with sodium carbonate and the mixture extracted with diethyl ether (3×20 ml). The organic layer was separated and back-washed with brine (3×30 ml). The organic layer was separated, dried ($Na_2SO_4$), filtered and evaporated to give an oil. Yield 3 g. An aliquot (150 mg) was dissolved in dichloromethane and purified using an ISCO Companion (4 g silica col. $CH_2Cl_2$ to $CH_2Cl_2$:ethyl acetate 9:1). The appropriate fractions were combined and evaporated to give an oil, 72 mg. $^1$H NMR (400 MHz, $CDCl_3$) δ 7.54 (s, 1H) 4.69, 4.48 (d, 2H) 4.00 (s, 3H) 1.70, 1.68, 1.67 (t, 1H). MS (ESI) m/z 181 (M+H)$^+$. LC-MS m/z 181 (M+H) GC-MS FID 100% Cl+ 181 (M+H)$^+$. TLC $CH_2Cl_2$:ethyl acetate 9:1 0.25 UV−ve DNPH+ve.

Step A11C: 1-methyl-5-(trifluoromethyl)-1H-pyrazole-4-carbaldehyde

The crude alcohol (1-methyl-5-(trifluoromethyl)-1H-pyrazol-4-yl)methanol (2.57 g, 0.014 mol) was dissolved in dichloromethane (30 ml) and added to a stirred suspension of 1,1,1-Triacetoxy-1,1-dihydro-1,2-benziodoxol-3(1H)-one (Dess-Martin Periodinane, 7.26 g, 0.017 mole) in dichloromethane (80 ml). (exotherm noted—controlled by cooling with ice-bath). The mixture was stirred while warming to room temperature overnight and the dichloromethane reduced to ~40 ml under vacuo at room temperature. Diethyl ether (200 ml) was added and the mixture poured into stirred sodium hydroxide solution. (1.3M, 150 ml) and the mixture swirled until cloudiness disappears. The organic layer was separated and back-washed with sodium hydroxide solution. (1.3M, 100 ml) and brine (2×100 ml). The organic layer was separated, dried ($Na_2SO_4$), filtered and evaporated to give a solid. Yield 2.0 g. The solid was dissolved in dichloromethane and purified using an ISCO Companion (40 g silica col. hexane to $CH_2Cl_2$). The appropriate fractions were combined and evaporated at room temperature to give a solid. Yield 1.45 g, 57%. $^1$H NMR (400 MHz, $CDCl_3$) δ 10.05 (s, 1H) 8.02 (s, 1H) 4.08 (s, 3H). TLC $CH_2Cl_2$ 0.6 UV+ve. GC-MS FID purity 100% Cl+. m/z 177, 179, 196 observed.

Step A11D: (R,E)-2-methyl-N-((1-methyl-5-(trifluoromethyl)-1H-pyrazol-4-yl)methylene) propane-2-sulfinamide 1-Methyl-5-(trifluoromethyl)-1H-pyrazole-4-carbaldehyde (1.0 g, 0.0056 mole) was dissolved in THF (20 ml) and Ti(OEt)$_4$ (2.56 g, 0.011 mole) in THF (5 ml) added and the solution stirred under nitrogen. (R)-(+)-2-methyl-2-propanesulfinamide (680 mg, 0.0056 mole) was added in a single portion and the reaction stirred under reflux and nitrogen for 6 hours. The solution was cooled to 0-5° C. and added to a cooled mix of brine and ethyl acetate (1:1, 120 ml) with rapid stirring. The mixture was filtered through Celite and the solids washed with more ethyl acetate. The organic layer was separated and back-washed with brine (2×60 ml). The organic layer was separated, dried ($Na_2SO_4$), filtered and evaporated to give a cloudy oil. Yield 1.7 g. The oil was dissolved in dichloromethane and purified using an ISCO Companion (40 g silica col., hexane to hexane:ethyl acetate 1:1). The appropriate fractions were combined and evaporated to give an oil, which solidified on standing. Yield 1.43 g, 90%. $^1$H NMR (400 MHz, $CDCl_3$) δ 8.63 (s, 1H) 8.02 (s, 1H) 4.07 (s, 3H) 1.25 (s, 9H). MS (ESI) m/z 282 (M+H)$^+$. LC-MS ESLD 100% m/z 282 (M+H)$^+$. TLC ethyl acetate:heptane 1:1 0.8 UV +ve. GC-MS Cl+ m/z 282 (M+H)$^+$.

Step A11E: (R)-N-((S)-1-(1-methyl-5-(trifluoromethyl)-1H-pyrazol-4-yl)ethyl)-2-methyl propane-2-sulfinamide Methyl magnesium chloride (3M in diethyl ether, 3.56 ml, 0.0107 moles) was added dropwise to a stirred solution of (R,E)-2-methyl-N-((1-methyl-5-(trifluoromethyl)-1H-pyrazol-4-yl)methylene)propane-2-sulfinamide (1.0 g, 0.035 moles) in dichloromethane (30 ml) at −70° C. under nitrogen. The mixture was allowed to warm to RT to give a cloudy solution and the solution was stirred overnight at RT under nitrogen. Ammonium chloride solution (saturated) was added slowly dropwise to quench the reaction. The mixture was diluted with water and extracted with ethyl acetate (3×20 ml). The organic layer was separated and back-washed with brine (2×30 ml). The organic layer was separated, dried ($Na_2SO_4$), filtered and evaporated to give an oil. Yield 1.1 g. $^1$H NMR (300 MHz $CDCl_3$) ratio 4.5:1 of diastereoisomers. The diastereoisomers were separated by silica gel chromatography using IPA/Heptane 20:80. The top diastereoisomer (100% de) was isolated. Yield 660 mg, 62%. $^1$H NMR (400 MHz $CD_3OD$) δ 7.48 (s, 1H) 4.79, 4.78, 4.76, 4.75, 4.73 (quin, 1H) 3.23, 3.21 (d, 1H) 1.58, 1.57 (d, 3H) 1.21 (s, 9H). MS (ESI) m/z 298 (M+H)$^+$. GC-MS Cl+298 (M+H)$^+$. TLC $CH_2Cl_2$:MeOH:$NH_4OH$ 95:5:0.5 0.3 UV−ve I$_2$+ve. [α]$_D$=−13.94° (c 1.65, $CH_3OH$).

Step A11F: (R)-N-{(1R)-1-[1-methyl-5-(trifluoromethyl)-1H-pyrazol-4-yl]ethyl}-2-methyl propane-2-sulfinamide The bottom diastereoisomer (100% de) was isolated. Yield 130 mg, 12%. $^1$H NMR (400 MHz $CD_3OD$) δ 7.53 (s, 1H) 4.77, 4.76, 4.75, 4.74, 4.73 (quin, 1H) 3.38, 3.39 (d, 1H) 1.53, 1.52 (d, 3H) 1.22 (s, 9H). MS (ESI) m/z 298 (M+H)$^+$. GC-MS Cl+ 298 (M+H)$^+$. TLC $CH_2Cl_2$:MeOH:$NH_4OH$ 95:5:0.5 0.28 UV−ve I$_2$+ve.

Step A11G: (S)-1-(1-methyl-5-(trifluoromethyl)-1H-pyrazol-4-yl)ethanamine Dihydrochloride (R)-N-((S)-1-(1-methyl-5-(trifluoromethyl)-1H-pyrazol-4-yl)ethyl)-2-methylpropane-2-sulfinamide (0.66 g, 0.0022 mole) was dissolved in HCl in dioxane (4M, 12 ml) and the solution stirred at RT overnight under nitrogen. The solution was evaporated and the residue suspended in ether and the white solid filtered off under a blanket of nitrogen. Yield 420 mg, 71% (hygroscopic). $^1$H NMR (400 MHz $CD_3OD$) δ 7.73 (s, 1H) 4.67, 4.65, 4.63, 4.62 (q, 1H) 4.02 (s, 3H) 1.62, 1.60 (d, 3H). MS (ESI) m/z 194 (M+H)$^+$ 177 (M+H—$NH_3$)$^+$. TLC $CH_2Cl_2$:MeOH:$NH_4OH$ 95:5:0.5 0.2 UV−ve KMnO4+ve. The free base was isolated using a SCX column eluting with methanol and then methanolic ammonia (1M) to release the amine. [α]$_D$=−11.43° (c 5.25, $CH_3OH$).

Step A11H: (R)-1-(1-methyl-5-(trifluoromethyl)-1H-pyrazol-4-yl)ethanamine, Dihydrochloride (R)-N-((R)-1-(1-methyl-5-(trifluoromethyl)-1H-pyrazol-4-yl)ethyl)-2-methylpropane-2-sulfinamide (0.135 g, 0.00045 mole) was dissolved in HCl in dioxane (4M, 8 ml) and the solution stirred at room temperature overnight under nitrogen. The solution was evaporated and the residue suspended in ether and the white solid filtered off under a blanket of nitrogen. Yield 120 mg 99% (hygroscopic). $^1$H NMR (400 MHz $CD_3OD$) 7.74 (s, 1H) 4.67, 4.66, 4.64, 4.62 (q, 1H) 4.02 (s, 3H) 1.63, 1.61 (d, 3H) MS (ESI) m/z 194 (M+H)$^+$177

(M+H—NH₃)⁺TLC CH₂Cl₂:MeOH:NH₄OH 95:5:0.5 0.2 UV-ve KMnO4+ve [α]_D=+2.87° (c=2.003, CH₃OH)

Carboxylic Acid 1: 2-(2,2,2-Trifluoro-1,1-dimethyl-ethyl)quinoline-6-carboxylic Acid

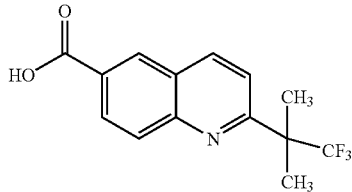

Step CA1A:
6-bromo-N-methoxy-N-methylquinoline-2-carboxamide

To a DMF (1 ml) solution of 6-bromoquinoline-2-carboxylic acid (4000 mg, 15.9 mmol, US2005165049A1), triethylamine (6.64 ml, 47.6 mmol), N,O-dimethylhydroxyamine hydrochloride (1860 mg, 19.0 mmol) and HBTU (6620 mg, 17.5 mmol) were added and the mixture was stirred for 24 hours at room temperature. The reaction was quenched with saturated NaHCO₃ aqueous solution and water, and the product was extracted with EtOAc 3 times. The combined organic extracts were dried over Na₂SO₄, and concentrated in vacuo. The crude residue was applied to a silica gel column chromatography and eluted with hexane/ethyl acetate (4:1) to furnish the title compound (4.29 g, 92% yield) as an orange solid. ¹H NMR (300 MHz, CDCl₃) δ 3.47 (3H, s), 3.80 (3H, s), 7.68-7.80 (1H, brs), 7.81-7.85 (1H, m), 8.00-8.06 (2H, m), 8.17 (1H, d, J=8.1 Hz). MS (ESI): m/z 295, 297 (M+H)⁺.

Step CA1B: 1-(6-Bromoquinolin-2-yl)ethanone

To a solution of the product of step 1A (4.29 g, 14.5 mmol) in THF (100 ml) was added methyl magnesiumbromide (18.2 ml, 17.4 mmol, 0.96M in THF solution) at 0° C. dropwise and the mixture was stirred at 0° C. for 1 hour. Then, the mixture was quenched with saturated ammonium chloride aqueous solution (50 ml) and water (200 ml). After stirring for 30 min, the product was extracted with ethyl acetate and dried over sodium sulfate. Filtration, evaporation, and purification through silica gel column chromatography, eluting with hexane/ethyl acetate (4:1) afforded the title compound (3.47 g, 96% yield) as a white solid. ¹H NMR (300 MHz, CDCl₃) δ 2.66 (3H, s), 7.83-7.88 (1H, m), 8.02-8.20 (4H, m). MS (ESI): m/z 250, 252 (M+H)⁺.

Step CA1C: 2-(6-Bromoquinolin-2-yl)-1,1,1-trifluoropropan-2-ol

A DMF (5 ml) solution of the product of Step CA1B (129 mg, 0.52 mmol), (trifluoromethyl)trimethylsilane (220 mg, 1.55 mmol) and tetrabutylammonium fluoride (13.5 mg, 0.052 mmol) was stirred at 100° C. for 2 hours. Then the mixture was cooled to room temperature and 1N-hydrochloric acid (2 ml) was added. After 4 hours, the mixture was quenched with saturated sodium bicarbonate aqueous solution, and the product was extracted with ethyl acetate which was dried over sodium sulfate. Filtration, evaporation and purification through silica gel column chromatography, eluting with hexane/ethyl acetate (4:1) to furnish the title compound (175 mg, quant.) as a white solid. H NMR (300 MHz, CDCl₃) δ 1.81 (3H, s), 6.51 (1H, s), 7.64 (1H, d, J=8.1 Hz), 7.66-7.89 (1H, m), 8.00-8.12 (2H, m), 8.21 (1H, d, J=8.8 Hz). MS (ESI): m/z 320, 322 (M+H)⁺.

Step CA1D: 1-(6-Bromoquinolin-2-yl)-2,2,2-trifluoro-1-methylethyl methanesulfonate To a solution of the product of Step CA1C (1.93 g, 6.03 mmol) in THF (20 ml) was added sodium hydride (241 mg, 7.23 mmol) portionwise at 0° C. and the mixture was stirred at room temperature for 1 hour. A solution of methanesulfonyl chloride (829 mg, 7.23 mmol) in THF (2 ml) was added at 0°. Then the reaction mixture was stirred at room temperature for 16 hours. The mixture was quenched with saturated sodium bicarbonate aqueous solution, and the product was extracted with ethyl acetate and dried over sodium sulfate. Filtration, evaporation, and purification through silica gel column chromatography, eluting with hexane/ethyl acetate (15:1 to 5:1) afforded the title compound (1.11 g, 46% yield) as a white solid. ¹H NMR (300 MHz, CDCl₃) δ 2.45 (3H, s), 3.24 (3H, s), 7.81-7.86 (2H, m), 7.96-8.05 (2H, m), 8.17 (1H, d, J=8.8 Hz). MS (ESI): m/z 397, 399 (M+H)⁺.

Step CA1E: 6-Bromo-2-(2,2,2-trifluoro-1,1-dimethylethyl)quinoline

To a suspension of the product of Step CA1D (1.40 g, 3.52 mmol) in cyclohexane (14 ml) was added trimethylaluminum (14 ml, 14 mmol, 1.03M in hexane solution) at room temperature, and the mixture was stirred at room temperature for 16 hours. The reaction was carefully quenched with saturated sodium bicarbonate aqueous solution (10 ml), brine (10 ml) and diluted with ethyl acetate (100 ml). After the mixture was stirred for 30 minutes, the formed precipitate was removed by filtration through celite and washed with ethyl acetate. The filtrate was concentrated and purified through silica gel column chromatography eluting with hexane only to furnish the title compound (951 mg, 85% yield) as colorless oil. ¹H NMR (300 MHz, CDCl₃) δ 1.72 (6H, s), 7.66 (1H, d, J=8.8 Hz), 7.75-7.80 (1H, m), 7.96-8.00 (2H, m), 8.06 (1H, d, J=8.8 Hz). MS (ESI): m/z 318, 320 (M+H)⁺.

Step CA1F: Methyl 2-(2,2,2-trifluoro-1,1-dimethylethyl)quinoline-6-carboxylate

A mixture of the product of step CA1E (950 mg, 3.0 mmol), triethylamine (1.25 ml, 9.0 mmol), 1,3-bis(diphenylphosphino)propane (123 mg, 0.3 mmol), palladium acetate (67 mg, 0.3 mmol) and methanol (4.8 ml) in DMF (10 ml) was stirred at reflux under carbon monoxide (1 atm) for 16 hours. Then the reaction was quenched with saturated sodium bicarbonate aqueous solution and the product was extracted with ethyl acetate which was dried over sodium sulfate. Filtration, evaporation and purification through silica gel column chromatography eluting with hexane/ethyl acetate (25:1) to furnish the title compound (777 mg, 88% yield) as a white solid. ¹H NMR (300 MHz, CDCl₃) δ 1.74 (6H, s), 4.00 (3H, s), 7.71 (1H, d, J=8.8 Hz), 8.14 (1H, d, J=8.8 Hz), 8.25 (1H, d, J=8.8 Hz), 8.28-8.32 (1H, m), 8.58-8.59 (1H, m). MS (ESI): m/z 298 (M+H)⁺.

Step CA1G: 2-(2,2,2-trifluoro-1,1-dimethylethyl)quinoline-6-carboxylic Acid

A methanol (6 ml) and THF (6 ml) solution of the product of Step CA1F (777 mg, 2.6 mmol) and 2M-sodium hydroxide aqueous solution (2.6 ml, 5.2 mmol) was heated at 60° C. for 3 hours. After cooling to ambient temperature, the solvent was evaporated in vacuo and the residue was acidified to pH 2 with 2M hydrochloric acid. The aqueous layer was extracted with ethyl acetate and the combined solution was washed with brine, dried over sodium sulfate and evaporated in vacuo to give the crude product which was recrystallized from ethyl acetate and hexane to furnish the title compound (735 mg, 99% yield) as a white solid. $^1$H NMR (300 MHz, CDCl$_3$) δ 1.75 (6H, s), 7.74 (1H, d, J=8.8 Hz), 8.19 (1H, d, J=8.8 Hz), 8.29 (1H, d, J=8.8 Hz), 8.35-8.40 (1H, m), 8.69-8.70 (1H, m). MS (ESI): m/z 284 (M+H)$^+$.

Carboxylic Acid 2: 6-tert-Butyl-2-naphthoic Acid

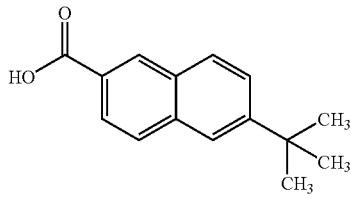

Step CA2A: Methyl 6-tert-butyl-2-naphthoate

A mixture of 2-bromo-6-tert-butylnaphthalene (980 mg, 3.72 mmol), palladium acetate (84 mg, 0.37 mmol), 1,3-bis(diphenylphosphino)propane (153 mg, 0.37 mmol) and triethylamine (1.56 ml, 11.2 mmol) in methanol (6 ml) and DMF (10 ml) was heated at 80° C. under carbon monoxide gas pressure (balloon) for 15 hours. After cooling to ambient temperature, the mixture was diluted with ethyl acetate-toluene (8:1)(160 ml) and filtered through a pad of celite. The filtrate and washings were washed with water, brine, dried over sodium sulfate and evaporated in vacuo to give the crude product which was purified through silica gel column chromatography, eluting with hexane/EtOAc (10:1), to furnish the title compound as colorless oil (843 mg, 94%). $^1$H NMR (300 MHz, CDCl$_3$): δ 1.43 (9H, s), 3.97 (3H, s), 7.61-7.67 (1H, m), 7.79-7.93 (3H, m), 8.01-8.07 (1H, m), 8.57 (1H, br, s).

Step CA2B: 6-tert-Butyl-2-naphthoic Acid

A mixture of methyl 6-tert-butyl-2-naphthoate (Step CA2A)(843 mg, 3.48 mmol) and 2M sodium hydroxide solution (6.96 mmol, 3.48 mmol) in methanol (30 ml) was treated according to the procedure described in step CA1G to furnish the title compound as a white solid (614 mg, 77%). $^1$H NMR (270 MHz, DMSO-d$_6$): δ 1.39 (9H, s), 7.70-7.76 (1H, m), 7.90-8.08 (4H, m), 8.55 (1H, br, s), 13.00 (1H, br, s).

Carboxylic Acid 3:
6-tert-butylquinoline-2-carboxylic Acid

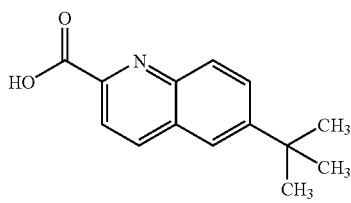

Step CA3A: 6-tert-butylquinoline 1-oxide

A mixture of 6-tert-butylquinoline (400 mg, 2.16 mmol, Journal of the Indian Chemical Society, 1998, 823) and mCPBA (639 mg, 2.59 mmol) in chloroform (10 ml) was stirred for 2 hours at room temperature. The mixture was concentrated and the crude residue was applied to a silica gel (NH silica) column chromatography and eluted with dichloromethane/methanol (20:1) to furnish the title compound (433 mg, quant.) as pale orange oil. $^1$H NMR (300 MHz, CDCl$_3$) δ 1.43 (9H, s) 7.26-7.30 (1H, m), 7.73 (1H, d, J=8.1 Hz), 7.78 (1H, s), 7.85 (1H, dd, J=1.5, 8.8 Hz), 8.49 (1H, d, J=5.9 Hz), 8.67 (1H, d, J=8.8 Hz). MS (ESI): m/z 202 (M+H)+.

Step CA3B: 6-tert-butylquinoline-2-carbonitrile

A mixture of the product of Step CA3A (310 mg, 1.54 mmol), trimethylsilylcyanide (458 mg, 4.62 mmol), trimethylamine (312 mg, 3.08 mmol) in acetonitrile (3 ml) was stirred for 15 minutes at 120° C. under microwave irradiation. The mixture was applied to a silica gel column chromatography and eluted with hexane/ethyl acetate (20:1) to furnish the title compound (295 mg, 91% yield) as a white solid. $^1$H NMR (300 MHz, CDCl$_3$) δ 1.44 (9H, s), 7.68 (1H, d, J=8.8 Hz), 7.79 (1H, d, J=2.2 Hz), 7.94 (1H, d, J=2.2, 8.8 Hz), 8.11 (1H, d, J=8.8 Hz), 8.26 (1H, d, J=8.8 Hz). MS (ESI): m/z 211 (M+H)+.

Step CA3C: 6-tert-butylquinoline-2-carboxylic Acid

A solution of the product of Step CA3B (295 mg, 1.40 mmol) and 2M-aqueous sodium hydroxide (3 ml) in ethanol (4.5 ml) was stirred for 4 hours at reflux. The mixture was diluted with water (10 ml), neutralized by 2M-aqueous hydrochloride and extracted with ethyl acetate (30 ml). The organic layer was dried over sodium sulfate, filtrated, and concentrated in vacuo to furnish the title compound (313 mg, quant.) as a white solid. $^1$H NMR (300 MHz, DMSO-d6) δ1.40 (9H, s), 7.93-7.97 (2H, m), 8.01-8.11 (2H, m), 8.41 (1H, d, J=8.1 Hz). MS (ESI): m/z 230 (M+H)+.

Carboxylic Acid 4

2-(2,2,2-trifluoro-1-hydroxy-1-methylethyl)quinoline-6-carboxylic Acid

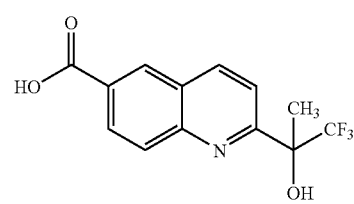

Step CA4A: Methyl 2-(2,2,2-trifluoro-1-hydroxy-1-methylethyl)quinoline-6-carboxylate The title compound was prepared from intermediate CA1C using the method of CA1F $^1$H NMR (300 MHz, CDCl$_3$) δ 1.82 (3H, s), 4.02 (3H, s), 6.55 (1H, s), 7.69 (1H, d, J=8.1 Hz), 8.18 (1H, d, J=8.8 Hz), 8.37-8.41 (2H, m), 8.66-8.68 (1H, m). MS (ESI): m/z 300 (M+H)+.

Step CA4B: 2-(2,2,2-trifluoro-1-hydroxy-1-methyl-ethyl)quinoline-6-carboxylic Acid The title compound was prepared from intermediate CA4A using the method of CA1G $^1$H NMR (300 MHz, CDCl$_3$) δ 1.84 (3H, s), 7.72 (1H, d, J=8.1 Hz), 8.23 (1H, d, J=8.8 Hz), 8.42-8.47 (2H, m), 8.77-8.78 (1H, m). MS (ESI): m/z 286 (M+H)+.

Carboxylic Acid 5: 2-(1-methylcyclopropyl)quinoline-6-carboxylic Acid

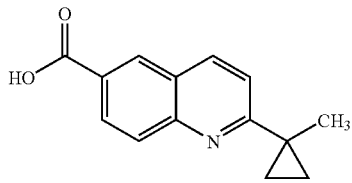

Step CA5A: 6-bromo-2-isopropenylquinoline

To a stirred suspension of (methyl)triphenylphosphonium bromide (2000 mg, 5.60 mmol) in dry THF (15 ml) was added a solution of potassium tert-butoxide (628 mg, 5.60 mmol) in dry THF (10 ml) with ice cooling. The mixture was then allowed to warm to room temperature. After 2 hours at room temperature, to this was added a solution of 1-(6-bromoquinolin-2-yl)ethanone (Step CA1B) (700 mg, 2.80 mmol) in dry THF (15 ml) with ice-cooling then the mixture was allowed to warm to room temperature. After 3 hours at ambient temperature, the mixture was quenched with water and extracted with ethyl acetate (×2). The combined solution was washed with brine, dried over sodium sulfate and concentrated in vacuo to give crude product, which was purified by column chromatography on silica gel (250 g) with hexane-ethyl acetate (10:1) to furnish the title compound (661 mg, 95%) as a tan solid. $^1$H NMR (270 MHz, CDCl$_3$) δ 2.34 (3H, s), 5.50 (1H, s), 5.93 (1H, s), 7.65-7.78 (2H, m), 7.88-8.03 (3H, m). MS (ESI): m/z 248.11, 250.14 [M+H]$^+$.

Step CA5B: methyl 2-isopropenylquinoline-6-carboxylate

A mixture of 6-bromo-2-isopropenylquinoline (200 mg, 1.45 mmol), palladium acetate (18.1 mg, 0.081 mmol), 1,3-bis(diphenylphosphino)propane (33 mg, 0.081 mmol), triethylamine (245 mg, 2.42 mmol. 0.337 ml) and methanol (1.03 g, 1.31 ml 32.2 mmol) in dry DMF (2.5 ml) was heated at 80° C. under carbon monoxide gas (balloon) overnight (15 hours). The mixture was diluted with ethyl acetate-toluene (8:1) (159 ml) and the precipitate was filtered through a pad of celite. The organic layer was washed with water (×2), brine, dried over sodium sulfate and concentrated in vacuo to give the crude product. The crude product was purified by column chromatography on silica gel (150 g) with hexane-ethyl acetate (15:1) to furnish the title compound (150 mg, 82%) as dark yellow solid. $^1$H NMR (270 MHz, CDCl$_3$) δ 2.36 (3H, s), 3.99 (3H, s), 5.53-5.57 (1H, m), 5.98 (1H, s), 7.73-7.78 (1H, m), 8.08-8.31 (3H, m), 8.54-8.56 (1H, m). MS (ESI): m/z 228.21 [M+H]$^+$.

Step CA 5C: methyl 2-(1-methylcyclopropyl)quinoline-6-carboxylate

To a stirred suspension of trimethylsulfoxonium iodide (435 mg, 2.06 mmol) in dimethylsulfoxide (3 ml) and THF (2 ml) was added potassium tert-butoxide (231 mg, 2.06 mmol) in one portion at ambient temperature. After 30 min. at the same temperature, to this (colorless solution) was added a solution of methyl 2-isopropenylquinoline-6-carboxylate (312 mg, 1.37 mmol) in THF (3 ml) at room temperature. The mixture was stirred at room temperature for 40 min then 1 hour at 60° C. The mixture was quenched with water and diluted with ethyl acetate-toluene (8:1) (90 ml). The organic solution was separated and washed with water (×2), brine, dried over sodium sulfate and concentrated in vacuo to crude product. The crude product was purified by column chromatography on silica gel (250 g) with hexane-ethyl acetate (10:1) to furnish the title compound (225 mg, 68%) as a white solid. $^1$H NMR (270 MHz, CDCl$_3$) δ 0.91-0.98 (2H, m), 1.38-1.45 (2H, m), 1.64 (3H, s), 3.98 (3H, s), 7.42-7.48 (1H, m), 7.97-8.27 (3H, m), 8.50-8.55 (1H, m). MS (ESI): m/z 242.15 [M+H]$^+$.

Step CA5D: 2-(1-methylcyclopropyl)quinoline-6-carboxylic Acid

A solution of Methyl-2-(1-methylcyclopropyl)quinoline-6-carboxylate (225 mg, 0.93 mmol) and 2M sodium hydroxide solution (2 ml. 4 mmol) in methanol (10 ml) was heated at 60° C. for 2 hours. After the solvent was evaporated in vacuo, the residue was dissolved in water. The aqueous solution was neutralized with 2M hydrochloric acid solution (2 ml) and the precipitated white solid was extracted with ethyl acetate (×3). The combined solution was washed with brine, dried over sodium sulfate and concentrated in vacuo to give crude white solid, which was recrystallized from ethyl acetate and hexane to furnish the title compound (177 mg, 84%) as a white solid. MS (ESI): m/z 228.15 [M+H]$^+$, 226.13 [M–H]$^-$.

Carboxylic Acid 6: 6-(1-methylcyclopropyl)-2-naphthoic Acid

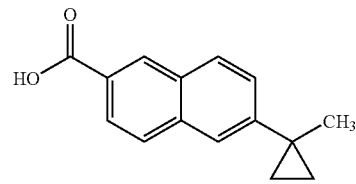

Step CA6A: Methyl 6-(prop-1-en-2-yl)-2-naphthoate

A suspension of methyl triphenylphosphonium bromide (2.41 g, 6.74 mmol) in THF (20 ml) was added dropwise potassium tert-butoxide (756 mg, 6.74 mmol) in THF (20 ml) at 0° C., and the mixture was stirred at room temperature for 1.5 hours. Then, methyl 6-acetyl-2-naphthoate (*J. Org. Chem.*, 1990, 55, 319-324, 769 mg, 3.37 mmol) in THF (5 ml) was added at room temperature, and the resulting mixture was stirred at room temperature for 2 hours. The reaction was quenched with water (100 ml) and extracted with ethyl acetate-hexane (1:2). The organic layer was dried over sodium sulfate and concentrated in vacuo. The crude material was purified by silica gel column chromatography, eluting with ethyl acetate-hexane (0:100 to 1:20) to give 0.67 g (88% yield) of the title compound as white solid. $^1$H NMR (270 MHz, CDCl$_3$) δ 2.28 (3H, s), 3.99 (3H, s), 5.26 (1H, s), 5.58 (1H, s), 7.74 (1H, d, J=8.6 Hz), 7.82-7.97 (3H, m), 8.05 (1H, d, J=8.6 Hz), 8.58 (1H, s).

Step CA6B: methyl 6-(1-methylcyclopropyl)-2-naphthoate

Diethylzinc (1.0 M solution in hexane, 6.30 ml, 6.30 mmol) was added to a solution of the product of Step CA6A (0.57 g, 2.5 mmol) in 1,2-dichloroethane (25 ml) at 0° C. Diiodomethane (1.01 ml, 12.6 mmol was then added dropwise to the solution and the resultant mixture was stirred at 60° C. for 20 hours. The reaction mixture was cooled to room temperature, diluted with saturated aqueous ammonium chloride solution (30 ml), and the mixture was extracted with dichloromethane (30 ml×3 times). The combined organic layer was washed with saturated aqueous sodium bicarbonate (50 mL) and brine (50 mL), and the organic layer was dried over sodium sulfate. Removal of the solvent gave a residue, which was chromatographed on a column of silica gel, eluting with ethyl acetate-hexane (1:20), to give 0.91 g of the title compound as white solid. This crude product as used for the next step without further purification.

$^1$H NMR (270 MHz, CDCl$_3$) δ 0.75-0.95 (2H, m), 0.95-1.13 (2H, m), 1.52 (3H, s), 3.97 (3H, s), 7.41 (1H, d, J=9.9 Hz), 7.74 (1H, s), 7.82 (1H, d, J=7.8 Hz), 7.86 (1H, d, J=8.6 Hz), 8.04 (1H, d, J=8.6 Hz), 8.56 (1H, s).

Step CA6C: 6-(1-methylcyclopropyl)-2-naphthoic Acid

A mixture of the product of Step CA6B (crude 0.91 g, 2.5 mmol) and 2M sodium hydroxide solution (3.8 ml) in methanol (7.6 ml) was heated at 60° C. for 2 hours. After cooling to room temperature, the mixture was washed with diethyl ether (100 ml). The aqueous layer was acidified to pH<3 with 2M hydrochloric acid solution and the mixture was extracted with dichloromethane-methanol (10:1, 150 ml×3 times). The combined organic layer was dried over sodium sulfate and concentrated in vacuo to give 0.444 g (78% yield in 2 steps) of the title compound as white solid. $^1$H NMR (300 MHz, DMSO-d$_6$) δ 0.77-0.92 (2H, m), 0.95-1.11 (2H, m), 1.49 (3H, s), 7.42 (1H, d, J=8.8 Hz), 7.84 (1H, s), 7.90-7.97 (2H, m), 8.01 (1H, d, J=8.8 Hz), 8.54 (1H, s). MS (ESI): m/z 225 (M−H)$^−$.

Carboxylic Acid 7: 6-(2,2,2-trifluoro-1-hydroxy-1-methylethyl)-2-naphthoic Acid

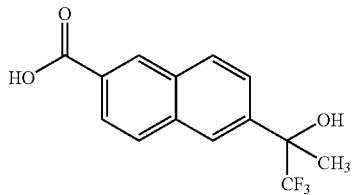

Step CA7A: 2-(6-bromo-2-naphthyl)-1,1,1-trifluoropropan-2-ol

To a DMF (25 ml) solution of 1-(6-bromo-2-naphthyl) ethanone (2.5 g, 10.0 mmol, Tetrahedron Letters (2001), 42(2), 265-266), trifluoromethyltrimethylsilane (2.14 g, 15.1 mmol) and lithium acetate (33.1 mg, 0.5 mmol) were added and the mixture was stirred for 12 hrs at room temperature. Then, the reaction was partitioned with sodium acetate aqueous solution and ethylacetate. The organic layer was dried over sodium sulfate and filtered. Then, evaporation gave the crude residue which was treated with hydrogen chloride and methanol with stirring for 5 hrs. Then, evaporation gave the crude residue which was purified through silica gel column chromatography, eluting with hexane:ethyl acetate (5:1), to give the title compound as colorless oil in 83% yield. $^1$H NMR (300 MHz, CDCl$_3$) δ 2.50 (1H, s), 7.58 (1H, d, J=8.8 Hz), 771-7.81 (3H, m), 8.04 (2H, d, J=8.9 Hz).

Step CA7B; methyl 6-(2,2,2-trifluoro-1-hydroxy-1-methylethyl)-2-naphthoate

To a DMA (25 ml) and methanol (1 ml) solution of the product of Step CA7A (1.0 g, 3.1 mmol), palladium acetate (70.0 mg, 0.31 mmol), diphenylphosphino propane (129 mg, 0.31 mmol) and triethylamine (951 mg, 9.4 mmol) were added and the mixture was stirred for 12 hrs at 100° C. under CO gas condition (balloon pressure). Then, the reaction was partitioned with water and ethyl acetate. The organic layer was dried over sodium sulfate and filtered. Then, evaporation gave the crude residue which was purified through silica gel column chromatography, eluting with hexane:ethyl acetate (5:1), to give the title compound as a colorless oil in 50% yield. $^1$H NMR (300 MHz, DMSO-d$_6$) δ 1.81 (3H, s), 3.93 (3H, s), 6.85 (1H, s), 7.81-8.00 (1H, m), 8.11-8.26 (4H, m), 8.66 (1H, s).

Step CA7C: 6-(2,2,2-trifluoro-1-hydroxy-1-methylethyl)-2-naphthoic Acid

To an ethanol (30 ml) solution of the product of Step CA7B (1.16 g, 3.1 mmol), sodium hydroxide aqueous solution (2M) (15 ml) was added and the mixture was stirred for 5 hrs at room temperature. Then, the reaction was acidified with dilute hydrochloric acid (20 ml) and the product was extracted with ethyl acetate and dried over sodium sulfate. Then filtration and evaporation gave the title compound as a white solid in 90% yield. $^1$H NMR (300 MHz, DMSO-d$_6$) δ 1.81 (3H, s), 6.85 (1H, s), 7.82 (1H, d, J=9.2 Hz), 7.99-8.25 (4H, m), 8.62 (1H, s), 12.9 (1H, brs).

Carboxylic Acid 8: 6-(2,2,2-trifluoro-1-methoxy-1-methylethyl)-2-naphthoic Acid

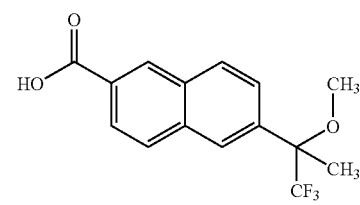

Step CA8A: methyl 6(2,2,2-trifluoro-1-methoxy-1-methylethyl)-2-naphthoate

To a THF solution of the product of Step CA7B (0.45 g, 1.5 mmol), sodium hydride (80 mg, 2.2 mmol) was added and the mixture was stirred for 30 minutes at 0° C. Then, methyl iodide (642 mg, 4.5 mmo) was added to the mixture and additional stirring was allowed for 3 hrs. Then, the product was extracted with ethyl acetate and dried over sodium sulfate. Then filtration, evaporation, and purification through silica gel column chromatography, eluting with hexane:ethyl acetate=4:1, gave the title compound as a white solid in 58% yield. $^1$H NMR (270 MHz, DMSO-$d_6$) δ 1.91 (3H, s), 3.22 (3H, s), 3.93 (3H, s) 7.72-7.75 (1H, m), 8.02-8.05 (1H, m), 8.13-8.24 (3H, m), 8.68 (1H, s).

Step CA8B: 6(2,2,2-trifluoro-1-methoxy-1-methyl-ethyl)-2-naphthoic Acid

The title compound was prepared by the same procedure as Step CA7C using the product of Step CA8A instead of the product of Step CA7B to give the title compound in 98% yield as a white solid.
$^1$H NMR (300 MHz, DMSO-$d_6$) δ 1.91 (3H, s), 3.22 (3H, s) 7.71-7.74 (1H, m), 8.01-8.21 (4H, m), 8.64 (1H, s), 13.2 (1H, brs).

Carboxylic Acid 9:
2-tert-butylquinoline-6-carboxylic Acid

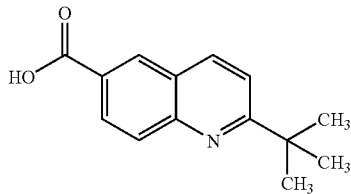

6-Quinolinecarboxylic acid (500 mg, 2.89 mmol) was dissolved in tetrahydrofuran (10 ml) under nitrogen and cooled to 0° C. 1.8M $^t$Butyl lithium in pentane (3.53 ml, 6.35 mmol) was added dropwise to the reaction over 30 minutes. The reaction was allowed to warm to room temperature over 1 h then stirred at room temperature for 4 hours. Saturated aqueous ammonium chloride solution (20 ml) was added and then extracted with ethyl acetate (2×20 ml). The combined organic fractions were washed with brine (20 ml) dried over Na$_2$SO$_4$, filtered and concentrated. The intermediate 2-tert-Butyl-1,2-dihydro-quinoline-6-carboxylic acid was purified by silica gel column chromatography, eluted with heptane/ethyl acetate=100/0 to 0/100. The product containing fractions were combined; manganese dioxide (2510 mg, 28.9 mmol) was added directly to this solution and stirred together for 1 h. The reaction was then filtered through celite to give the title product as a cream solid. (300 mg, 45% yield). NMR (400 MHz, DMSO-$d_6$) δ 1.38-1.40 (9H s) 7.59-7.62 (1H d) 7.77-7.80 (1H d) 8.16-8.20 (1H dd) 8.25-8.29 (1H d) 8.32-8.35 (1H d). MS (ESI/APCI) m/z 230 (M+H)$^+$ m/z 415 (M−H)$^−$.

Carboxylic Acid 10:
2-(trifluoromethyl)quinoline-6-carboxylic Acid

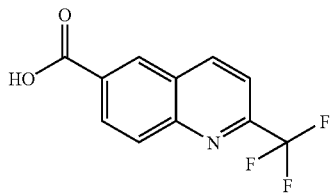

Step CA10A: tert-butyl quinoline-6-carboxylate

To a suspension of 6-quinolinecarboxylic acid (12 g, 69 mmol) in DMF (100 mL) was added 1,1'-Carbonyldiimidazole (11.2 g, 69.3 mmol) and the mixture stirred at 40° C. for 1 hour. tert-Butanol (13 mL, 139 mmol) and 1,8-Diazabicyclo [5.4.0]undec-7-ene (10.4 mL, 69.3 mmol) were added and the mixture was stirred at 80° C. for 4 h. After cooling to room temperature the reaction mixture was quenched with water (400 mL) and extracted with ethyl acetate/heptane (1:3, 2×400 mL). The organic layer was dried over MgSO$_4$ and concentrated to give quinoline-6-carboxylic acid t-butyl ester (14.54 g, 92%). $^1$H NMR (400 MHz, CDCl$_3$) δ 1.63 (9H, s), 7.42-7.46 (1H, m), 8.10 (1H, d), 8.23 (1H, d), 8.26 (1H, d), 8.50 (1H, d), 8.96-8.98 (1H, m). LCMS: Retention time: 1.42 min. MS (ESI) m/z 230 (M+H)$^+$ Step CA10B: tert-butyl 1-oxyquinoline-6-carboxylate To a solution of tert-butyl quinoline-6-carboxylate (14.54 g, 63 mmol) in dichloromethane (100 mL) was added meta-chloroperbenzoic acid (16.4 g, 95.1 mmol) and the mixture stirred at room temperature for 16 hours. The reaction mixture was diluted with more dichloromethane (250 mL) and washed with sat. aq. NaHCO$_3$ (200 mL). The organic layer was dried over magnesium sulfate, filtered and solvent removed under reduced pressure to give a crude residue which was purified by silica gel column chromatography (EtOAc:Heptane=7:3; 17:3; 19:1 then CH$_2$Cl$_2$:MeOH=190:1) to give 1-Oxyquinoline-6-carboxylic acid tert-butyl ester (10.69 g, 69%). $^1$H NMR (400 MHz, CDCl$_3$) δ 1.65 (9H, s), 7.33-7.38 (1H, m), 7.83 (1H, d), 8.26-8.30 (1H, m), 8.54 (1H, d), 8.57-8.59 (1H, m), 8.78 (1H, d). LCMS: Retention time: 1.31 min. MS (ESI) m/z 246 (M+H)$^+$.

Step CA10C: tert-butyl 2-(trifluoromethyl)quinoline-6-carboxylate

To a solution of tert-butyl 1-oxyquinoline-6-carboxylate (6 g, 20 mmol) and (trifluoromethyl)trimethylsilane (6.15 mL, 41.6 mmol) in THF (100 mL) at 0° C. was added cesium fluoride (400 mg, 2.6 mmol) and the reaction mixture warmed to room temperature and allowed to stir for 16 h. The reaction mixture was cooled to 0° C. and additional (trifluoromethyl)trimethylsilane (4.70 mL, 31.8 mmol) and cesium fluoride (400 mg, 2.6 mmol) were added. The THF was removed under reduced pressure to give a crude residue which was dissolved in EtOAc (150 mL) and washed with sat. aq. NaHCO$_3$ (2×50 mL) and then brine (2×30 mL). The organic layer was dried over magnesium sulfate, filtered and solvent removed under reduced pressure to give a crude residue which was purified by silica gel column chromatography (EtOAc:Heptane=7:3) to give 2-trifluoromethylquinoline-6-carboxylic acid tert-butyl ester (3.53 g, 50%). $^1$H NMR (400 MHz, CDCl$_3$) δ 1.66 (9H, s), 7.80 (1H, d), 8.25 (1H, d), 8.36 (1H, dd), 8.47 (1H, d), 8.59 (1H, d). LCMS: Retention time: 1.75 min. MS (ESI) m/z 298 (M+H)$^+$.

Step CA10D:
2-(trifluoromethyl)quinoline-6-carboxylic Acid

To a solution of tert-butyl 2-trifluoromethylquinoline-6-carboxylate (2 g, 7 mmol) in dichloromethane (50 mL), cooled to 0° C., was added trifluoroacetic acid (5.18 mL, 67.2 mmol) and the reaction mixture allowed to warm to room temperature and stirred for 36 h. The reaction mixture was concentrated under reduced pressure and the crude product obtained triturated with heptane (4×10 mL) to give 2-trifluoromethylquinoline-6-carboxylic acid (1.58 g, 98%). $^1$H NMR (400 MHz, CD$_3$OD) δ 7.93 (1H, d), 8.24 (1H, d), 8.42 (1H, dd), 8.73 (1H, d), 8.78 (1H, d). LCMS: Retention time: 1.38 min. MS (ESI) m/z 242 (M+H)$^+$.

Carboxylic Acid 11: 2-(pentafluoroethyl)quinoline-6-carboxylic Acid

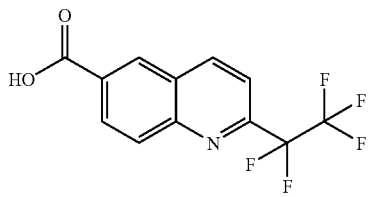

Step CA11A: tert-butyl 2-(pentafluoroethyl)quinoline-6-carboxylate

To a solution of tert-butyl 1-oxyquinoline-6-carboxylate (0.20 g, 0.815 mmol) and (pentafluoroethyl)trimethylsilane (300 mg, 1.56 mmol) in THF (5 mL) at 0° C. was added cesium fluoride (15 mg, 0.1 mmol) and the reaction mixture warmed to room temperature and allowed to stir for 3 h. Additional (pentafluoroethyl)trimethylsilane (0.175 mL, 0.90 mmol) was added and the mixture stirred at RT for 16 hours. The mixture was dissolved in EtOAc (60 mL) and washed with sat. aq. NaHCO$_3$ (30 mL). The organic layer was dried over sodium sulfate, filtered and solvent removed under reduced pressure to give a crude residue which was purified by silica gel column chromatography (EtOAc:Heptane=85:15) to give 2-pentafluoroethylquinoline-6-carboxylic acid t-butyl ester (165 mg, 58%). $^1$H NMR (400 MHz, CDCl$_3$) δ 1.66 (9H, s), 7.80 (1H, d), 8.25 (1H, d), 8.36 (1H, dd), 8.47 (1H, d), 8.60 (1H, d). LCMS: Retention time: 1.84 min. MS (ESI) m/z 348 (M+H)$^+$.

Step CA11B: 2-(pentafluoroethyl)quinoline-6-carboxylic Acid

To a solution of tert-butyl 2-pentafluoroethylquinoline-6-carboxylate (165 mg, 0.475 mmol) in dichloromethane (5 mL), cooled to 0° C., was added trifluoroacetic acid (2 mL, 26 mmol) and the reaction mixture allowed to warm to room temperature and stirred for 16 h. The reaction mixture was concentrated under reduced pressure to give the crude product, 2-pentafluoroethylquinoline-6-carboxylic acid (140 mg, 100%). $^1$H NMR (400 MHz, CDCl$_3$+2drops CD$_3$OD) δ 7.79 (1H, d), 8.26 (1H, d), 8.39 (1H, dd), 8.47 (1H, d), 8.67 (1H, d). LCMS: Retention time: 1.49 min. MS (ESI) m/z 292 (M+H)$^+$.

EXAMPLES

Example 1

N-[(1R)-(1,5-dimethyl-1H-pyrazol-4-yl)ethyl)]-2-(2,2,2-trifluoro-1,1-dimethylethyl)quinoline-6-carboxamide

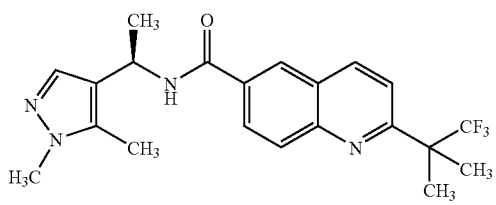

To a DMF (3.8 ml) solution of (1R)-1-(1,5-dimethyl-1H-pyrazol-4-yl)ethanamine dihydrochloride (80 mg, 0.38 mmol), 6-tert-butyl-2-naphthoic acid (107 mg, 0.38 mmol), HBTU (150 mg, 0.396 mmol) and N,N-diisopropylethylamine (0.197 ml, 1.13 mmol) were added and the mixture was stirred for 24 hours at room temperature. The reaction was quenched with sat. NaHCO$_3$ aq and water, and the product was extracted with EtOAc 3 times. The combined organic extracts were dried over Na$_2$SO$_4$, and concentrated in vacuo. The crude material was purified by HPLC (column: MS C 30×50 mm, acetonitrile: 0.01% NH$_3$ aq=96:4 to 4:96 as eluent, retention time=3.90 min) to give the title product (140 mg, 92%) as a white solid. $^1$H NMR (300 MHz, CDCl$_3$) δ 1.65 (3H, d, J=6.0 Hz), 1.73 (6H, s), 2.30 (3H, s), 3.79 (3H, s), 5.28-5.37 (1H, m), 6.30 (1H, brd, J=9.0 Hz), 7.49 (1H, s), 7.70 (1H, d, J=9.0 Hz), 8.01 (1H, d, J=9.0 Hz), 8.14 (1H, d, J=9.0 Hz), 8.21 (1H, d, J=9.0 Hz), 8.25 (1H, s). MS (ESI) m/z 403 (M–H)$^-$, 405 (M+H)$^+$.

The following compounds were prepared by a method analogous to that described in Example 1 and Scheme 1, using the starting materials as detailed below.

Example 2

N-[(1,5-dimethyl-1H-pyrazol-4-yl)methyl]-2-(2,2,2-trifluoro-1,1-dimethylethyl)quinoline-6-carboxamide

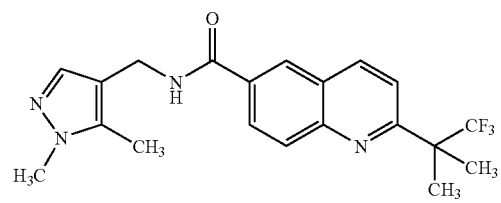

Prepared using 1-(1,5-dimethyl-1H-pyrazol-4-yl)methanamine and Carboxylic Acid 1. $^1$H NMR (300 MHz, CDCl$_3$) δ 1.74 (6H, s), 2.33 (3H, s), 3.82 (3H, s), 4.53 (2H, d, J=5.2 Hz), 6.25 (1H, s), 7.48 (1H, s), 7.73-8.28 (5H, m). MS (ESI) m/z 391 (M+H)$^+$.

Example 3

(R)-N-(1-(5-cyano-1-methyl-1H-pyrazol-4-yl)ethyl)-2-(2,2,2-trifluoro-1,1-dimethylethyl)quinoline-6-carboxamide

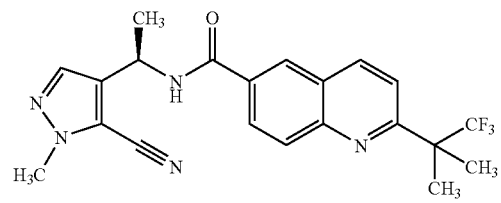

Prepared using Amine 3 and Carboxylic Acid 1. $^1$H NMR (270 MHz, DMSO-d$_6$) δ 1.57 (3H, d, J=7.3 Hz), 1.71 (6H, s), 3.98 (3H, s), 5.30 (1H, m), 7.11 (1H, d, J=11.9 Hz), 7.74 (1H, s), 7.88 (1H, d, J=8.6 Hz), 8.09 (1H, d, J=9.2 Hz), 8.23 (1H, dd, J=2.0 Hz, 8.6 Hz), 8.49-8.60 (2H, m), 9.16 (1H, d, J=7.9 Hz). MS (ESI): m/z 416 (M+H)$^+$, 414 (M–H)$^-$.

Example 4

(R)-N-(1-(5-(hydroxymethyl)-1-methyl-1H-pyrazol-4-yl)ethyl)-2-(2,2,2-trifluoro-1,1-dimethylethyl)quinoline-6-carboxamide

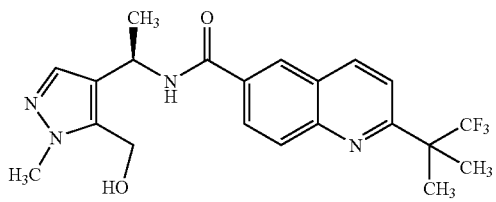

Prepared using Amine 4 and Carboxylic Acid 1. $^1$H NMR (270 MHz, DMSO-$d_6$) δ 1.51 (3H, d, J=7.3 Hz), 1.71 (6H, s), 3.79 (3H, s), 4.52 (1H, dd, J=5.3 Hz, 13.2 Hz), 4.61 (1H, dd, J=5.3 Hz, 13.2 Hz), 5.16 (1H, t, J=5.3 Hz), 5.25 (1H, m), 7.45 (1H, s), 7.87 (1H, d, J=9.2 Hz), 8.06 (1H, d, J=9.2 Hz), 8.19 (1H, d, J=8.6 Hz), 8.46-8.56 (2H, m), 8.89 (1H, d, J=8.9 Hz). MS (ESI): m/z 421 (M+H)$^+$, 419 (M−H)$^-$.

Example 5

N-(1-(5-methyl-1-(2,2,2-trifluoroethyl)-1H-pyrazol-4-yl)ethyl)-2-(2,2,2-trifluoro-1,1-dimethylethyl)quinoline-6-carboxamide

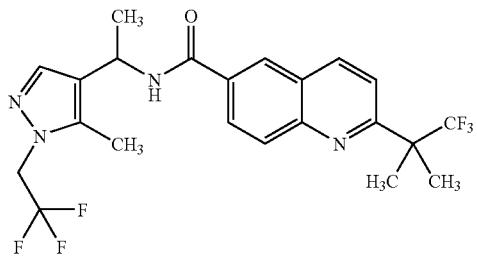

Prepared using Amine 6 and Carboxylic Acid 1. $^1$H NMR (300 MHz, DMSO-$d_6$) δ 1.51 (3H, d, J=6.0 Hz), 1.71 (6H, s), 2.31 (3H, s), 5.02 (1H, d, J=9.0 Hz), 5.08 (1H, d, J=9.0 Hz), 5.16-5.25 (1H, m), 7.60 (1H, s), 7.88 (1H, d, J=9.0 Hz), 8.08 (1H, d, J=9.0 Hz), 8.19-8.23 (1H, m), 8.51-8.54 (2H, m), 8.93 (1H, brd, J=9.0 Hz). MS (ESI) m/z 471 (M−H)$^-$, 473 (M+H)$^+$. The chemical structure (1,5-substitution on the pyrazole ring) of the title compound was ascertained by NMR analysis ($^1$H-1D, COSY, pNOESY and pROESY).

Example 6

N-((1R)-1-(5-methyl-1-(2,2,2-trifluoroethyl)-1H-pyrazol-4-yl)ethyl)-2-(2,2,2-trifluoro-1,1-dimethylethyl)quinoline-6-carboxamide

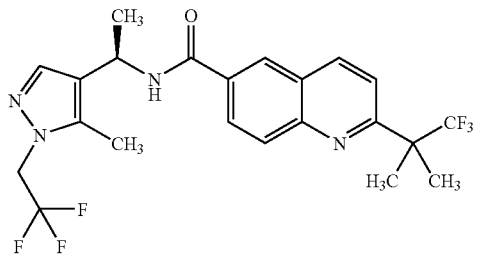

Prepared using Amine 7 and Carboxylic Acid 1. $^1$H NMR data of Example 6 is same with that of Example 5. The optical purity (>99% e.e.) of Example 6 was detected by chiral-HPLC; DAICEL Chiralpak AD-H 4.6×250 mm, n-Hexane/2-Propanol/Diethylamine=85/15/0.1 (v/v/v) as eluent, retention time: 10.0 mim; Retention time of the corresponding racemic compound: 10.1, 13.0 min.

Example 7

N-[1-(1,5-dimethyl-1H-pyrazol-4-yl)propyl]-2-(2,2,2-trifluoro-1,1-dimethylethyl)quinoline-6-carboxamide

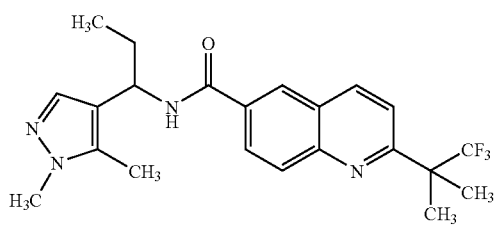

Prepared using Amine 5 and Carboxylic Acid 1. $^1$H NMR (300 MHz, DMSO-$d_6$) δ 0.89 (3H, t, J=6.6 Hz), 1.71 (6H, s), 1.75-1.98 (2H, m), 2.24 (3H, s), 3.68 (3H, s), 4.91-4.96 (1H, m), 7.38 (1H, s), 7.86 (1H, d, J=8.1 Hz), 8.06 (1H, d, J=8.8 Hz), 8.19 (1H, d, J=8.8 Hz), 8.50-8.53 (2H, m), 8.77 (1H, d, J=8.1 Hz). MS (ESI): m/z 419 (M+H)$^+$.

Example 8

N-[(1R)-1-(1,5-dimethyl-1H-pyrazol-4-yl)propyl]-2-(2,2,2-trifluoro-1,1-dimethylethyl)quinoline-6-carboxamide

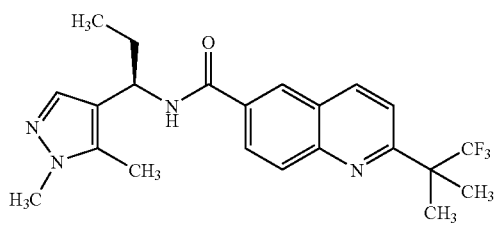

The racemic compound of Example 7 was separated by DAICEL CHIRALPAK AD-H (250 mm×20 mm, column temp: 40° C.). Mobile phase is n-Hexane/Isopropanol/Diethylamine=85/15/0.1 and flow rate is 18.9 ml/min. The 1$^{st}$ peak, retention time 9.1 mm, was the undesired enantiomer of title compound and the 2$^{nd}$ peak, retention time 13.1 mm, was the title compound. $^1$H NMR (300 MHz, DMSO-$d_6$) δ 0.89 (3H, t, J=6.6 Hz), 1.71 (6H, s), 1.75-1.98 (2H, m), 2.24 (3H, s), 3.68 (3H, s), 4.91-4.96 (1H, m), 7.38 (1H, s), 7.86 (1H, d, J=8.1 Hz), 8.06 (1H, d, J=8.8 Hz), 8.19 (1H, d, J=8.8 Hz), 8.50-8.53 (2H, m), 8.77 (1H, d, J=8.1 Hz). MS (ESI): m/z 419 (M+H)$^+$.

Example 9

N-[1-(5-methyl-1H-pyrazol-4-yl)ethyl]-2-(2,2,2-trifluoro-1,1-dimethyl ethyl)quinoline-6-carboxamide

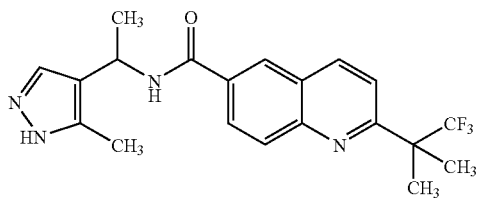

Prepared using Amine 9 and Carboxylic Acid 1. ¹H NMR (270 MHz, DMSO-d6) δ 1.50 (3H, d, J=6.5 Hz), 1.71 (6H, s), 2.19 (3H, br.s), 5.14-5.28 (1H, m), 7.40-7.70 (1H, br.s), 7.87 (1H, d, J=8.4 Hz), 8.07 (1H, d, J=9.2 Hz), 8.18-8.25 (1H, m), 8.48-8.56 (2H, m), 8.81 (1H, br.s), 12.20-12.50 (1H, br.s).

Example 10

2-(5-Methyl-4-(1-(2-(2,2,2-trifluoro-1,1-dimethylethyl)quinoline-6-carboxamido)ethyl)-1H-pyrazol-1-yl)acetate

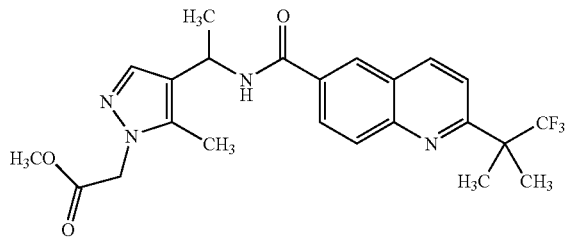

Prepared using Amine 8 and Carboxylic Acid 1 (10% yield). ¹H NMR (300 MHz, DMSO-$d_6$) δ 1.51 (3H, d, J=6.0 Hz), 1.71 (6H, s), 2.21 (3H, s), 3.68 (3H, s), 5.00 (2H, s), 5.17-5.27 (1H, m), 7.50 (1H, s), 7.88 (1H, d, J=9.0 Hz), 8.08 (1H, d, J=9.0 Hz), 8.20-8.23 (1H, m), 8.51-8.54 (2H, m), 8.91 (1H, brd, J=6.0 Hz). MS (ESI) m/z 461 (M−H)⁻, 463 (M+H)⁺. The chemical structure (1,5-substitution on the pyrazole ring) of the title compound was ascertained by NMR analysis (1H-1D, COSY, pNOESY and pROESY).

Example 11

N-(1-(1-(2-hydroxyethyl)-5-methyl-1H-pyrazol-4-yl)ethyl)-2-(2,2,2-trifluoro-1,1-dimethylethyl)quinoline-6-carboxamide

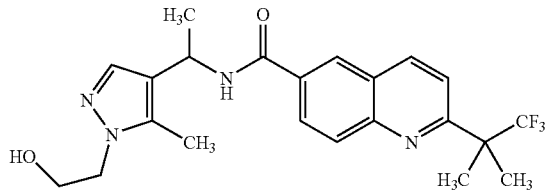

To a solution of Example 10 (23 mg, 0.05 mmol) in THF (3 ml) was added LiBH₄ powder (3.25 mg, 0.15 mmol) at rt, and the resulting mixture was heated at 65° C., then MeOH (3 drops) was added and the resulting mixture was heated at the same temperature for 60 min. After being cooled to rt, the reaction mixture was quenched by addition of sat. NH₄Cl aq. and the aqueous layer was extracted with AcOEt 3 times. The combined organic extracts were washed with water and brine successively, dried over Na₂SO₄ and concentrated in vacuo. The crude material was purified by HPLC (column: MS C 30×50 mm, acetonitrile: 0.01% NH₃ aq=96:4 to 4:96 as eluent) to give the title compound as a white solid (16.6 mg, 77% yield). ¹H NMR (300 MHz, DMSO-$d_6$) δ 1.50 (3H, d, J=6.0 Hz), 1.71 (6H, s), 2.26 (3H, s), 3.67 (2H, dd, J=6.0, 12.0 Hz), 4.03 (2H, t, J=6.0 Hz), 4.84 (1H, t, J=6.0 Hz), 5.14-5.24 (1H, m), 7.46 (1H, s), 7.87 (1H, d, J=9.0 Hz), 8.07 (1H, d, J=9.0 Hz), 8.19-8.23 (1H, m), 8.50-8.53 (2H, m), 8.85 (1H, brd, J=6.0 Hz). MS (ESI) m/z 433 (M−H)⁻, 435 (M+H)⁺.

Example 12

N-(1-(1-(2-hydroxy-2-methylpropyl)-5-methyl-1H-pyrazol-4-yl)ethyl)-2-(2,2,2-trifluoro-1,1-dimethylethyl)quinoline-6-carboxamide

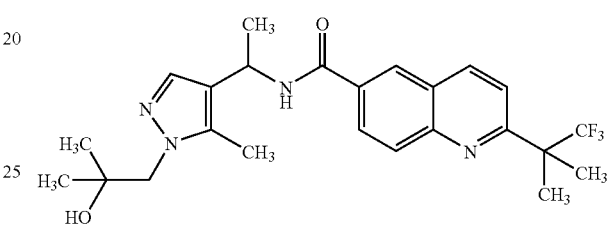

To a suspension of sodium hydride (30.7 mg, 0.768 mmol, 60% in oil, hexane wash for 3 times) in DMF (2 ml) was added Example 9 (100 mg, 0.256 mmol) at 0° C. under nitrogen, and the mixture was stirred at room temperature for 1 hour. Then, 1,1-dimethyloxirane (22.2 mg, 0.307 mmol) was added to the mixture, and stirred for further 20 hours at 60° C. After cooling, the reaction mixture was quenched with water, poured onto saturated aqueous sodium bicarbonate (30 ml), and extracted with dichloromethane (50 ml, 3 times). The combined organic layer was dried over sodium sulfate, filtered and evaporated. The crude material was purified by TLC-plate (1 mm thick plate, MeOH-DCM=1:10) to give the title compound as white solid (20.1 mg, 17% yield). ¹H NMR (270 MHz, DMSO-$d_6$) δ 1.08, 1.09 (each 3H, s), 1.50 (3H, d, J=6.6 Hz), 1.71 (6H, s), 2.27 (3H, s), 3.91 (2H, s), 4.65 (1H, s), 5.21 (1H, m), 7.48 (1H, s), 7.87 (1H, d, J=9.2 Hz), 8.07 (1H, d, J=8.6 Hz), 8.22 (1H, d, J=7.3 Hz), 8.46-8.59 (2H, m), 8.85 (1H, d, J=7.9 Hz). MS (ESI) m/z: 463 (M+H)⁺, 461 (M−H)⁻.

Example 13

N-[(1R)-1-(1,5-dimethyl-1H-pyrazol-4-yl)ethyl]-2-(1-methylcyclopropyl) quinoline-6-carboxamide

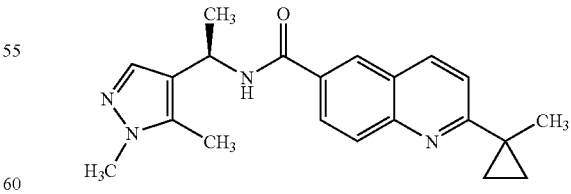

Prepared using Amine 2 and Carboxylic Acid 5. ¹H NMR (300 MHz, DMSO-$d_6$) δ 0.91-0.97 (2H, m), 1.29-1.34 (2H, m), 1.48 (3H, d, J=7.3 Hz), 1.59 (3H, s), 2.23 (3H, s), 3.68 (3H, s), 5.10-5.22 (1H, m), 7.39 (1H, s), 7.53 (1H, d, J=8.8 Hz), 7.89 (1H, d, J=8.8 Hz), 8.10 (1H, dd, J=2.2, 8.8 Hz), 8.33 (1H, d, J=8.8 Hz), 8.42 (1H, d, J=2.2 Hz), 8.76 (1H, d, J=8.1 Hz). MS (ESI) m/z 347 (M−H)⁻, 349 (M+H)⁺.

Example 14

N-[(1R)-1-(1,5-dimethyl-1H-pyrazol-4-yl)methyl]-2-(2,2,2-trifluoro-1-hydroxy-1-methylethyl)quinoline-6-carboxamide

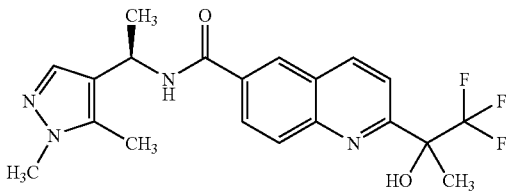

Prepared using Amine 2 and Carboxylic Acid 4. $^1$H NMR (300 MHz, DMSO-d$_6$) δ 1.49 (3H, d, J=7.3 Hz), 1.84 (3H, s), 2.24 (3H, s), 3.69 (3H, s), 5.13-5.23 (1H, m), 6.99 (1H, s), 7.37-7.43 (1H, m), 7.98 (1H, d, J=9.2 Hz), 8.08 (1H, d, J=8.5 Hz), 8.20-8.23 (1H, m), 8.54-8.57 (2H, m), 8.84 (1H, d, J=8.5 Hz). MS (ESI): m/z 407 (M+H)$^+$. Diastereomer mixture (1:1)

Example 15

N-[(1-ethyl-5-methyl-1H-pyrazol-4-yl)methyl]-2-(2,2,2-trifluoro-1,1-dimethylethyl)quinoline-6-carboxamide

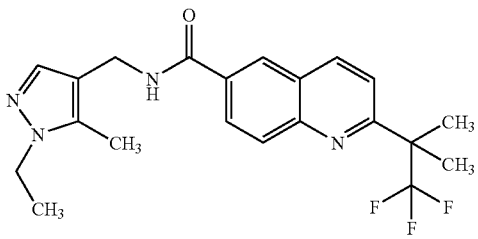

Prepared Using Commercially Available
1-(1-ethyl-5-methyl-1H-pyrazol-4-yl)methanamine and Carboxylic Acid 1. $^1$H NMR (300 MHz, DMSO-d$_6$) δ 1.27 (3H, t, J=7.3 Hz), 1.71 (6H, s), 2.28 (3H, s), 4.02 (2H, q, J=7.3 Hz), 4.31 (2H, d, J=5.1 Hz), 7.35 (1H, s), 7.86 (1H, d, J=8.8 Hz), 8.07 (1H, d, J=8.8 Hz), 8.19 (1H, d, J=8.8 Hz), 8.51 (1H, d, J=8.8 Hz), 8.52 (1H, s), 8.89 (1H, t, J=5.1 Hz). MS (ESI): m/z 405 (M+H)$^+$

Example 16

N-[1-(1-ethyl-5-methyl-1H-pyrazol-4-yl)ethyl]-2-(2,2,2-trifluoro-1,1-dimethylethyl)quinoline-6-carboxamide

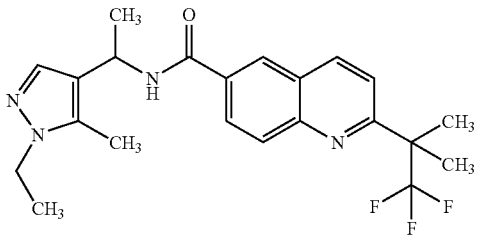

Prepared using commercially available 1-(1-ethyl-5-methyl-1H-pyrazol-4-yl)ethanamine and Carboxylic Acid 1. $^1$H NMR (300 MHz, DMSO-d$_6$) δ 1.27 (3H, t, J=7.3 Hz), 1.49 (3H, d, J=6.6 Hz), 1.71 (6H, s), 2.25 (3H, s), 4.01 (2H, q, J=7.3 Hz), 5.15-5.26 (1H, m), 7.44 (1H, s), 7.87 (1H, d, J=8.8 Hz), 8.06 (1H, d, J=8.8 Hz), 8.20 (1H, d, J=8.8 Hz), 8.51 (1H, d, J=8.8 Hz), 8.53 (1H, s), 8.85 (1H, d, J=8.1 Hz). MS (ESI): m/z 419 (M+H)$^+$.

Example 17

N-(1-cyclobutyl-5-methyl-1H-pyrazol-4-yl)ethyl)-2-(2,2,2-trifluoro-1,1-dimethylpropan-2-yl)quinoline-6-carboxamide

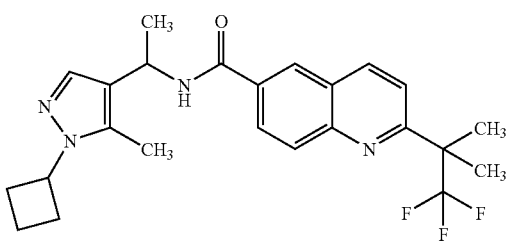

To a stirred suspension of Example 9 (50.2 mg, 0.129 mmol) in toluene (10 mL) were added cyclobutanol (20 μl, 0.3 mmol) and cyanomethylenetri-N-butylphosphorane (40.0 mg, 0.166 mmol) at room temperature for 18 hours. Then the mixture was heated to 100° C. and stirred for 3 hours. The reaction mixture was concentrated in vacuo and the residue was purified by TLC-plate (1 mm thick plate, AcOEt-DCM=1:2) followed by preparative-HPLC(Apparatus: Waters MS-trigger AutoPurification™ system, Column: Waters XTerra C18, 19×50 mm, 5 um particle, Eluent: MeOH/0.01% aq. NH$_4$OH) to give the title compound as colorless oil (15.2 mg, 27% yield). $^1$H NMR (300 MHz, DMSO-d$_6$) δ 1.49 (3H, d, J=6.6 Hz), 1.71 (6H, s), 1.71-1.82 (2H, m), 2.22 (3H, s), 2.23-2.35 (2H, m), 2.41-2.58 (2H, m), 4.76 (1H, tt, J=8.1 Hz), 5.11-5.24 (1H, m), 7.50 (1H, s), 7.87 (1H, d, J=8.8 Hz), 8.06 (1H, d, J=8.8 Hz), 8.20 (1H, dd, J=1.5, 8.8 Hz), 8.49-8.54 (1H, m), 8.52 (1H, d, J=1.5 Hz), 8.86 (1H, d, J=8.1 Hz). MS (ESI) m/z: 445 (M+H)$^+$.

Example 18

(S)-N-(1-(5-chloro-1-methyl-1H-pyrazol-4-yl)methyl)-2-(2,2,2-trifluoro-1,1-dimethylethyl)quinoline-6-carboxamide and

Example 18a (R)-N-(1-(5-chloro-1-methyl-1H-pyrazol-4-yl)ethyl)-2-(2,2,2-trifluoro-1,1-dimethylethyl)quinoline-6-carboxamide

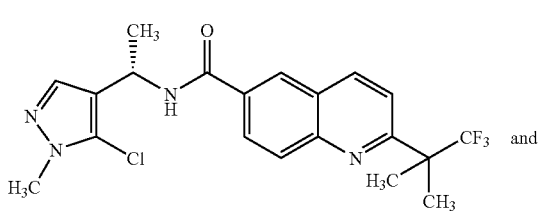

-continued

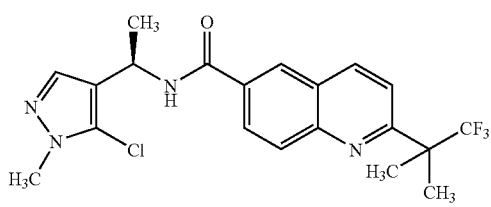

Example 18

(S)-1-(5-Chloro-1-methyl-1H-pyrazol-4-yl)ethanamine Dihydrochloride (Amine 10, 45 mg, 0.19 mmol), 2-(2,2,2-trifluoro-1,1-dimethyl-ethyl)-quinoline-6-carboxylic acid (55 mg, 0.194 mmol) and 2-(7-aza-1H-benzotriazole-1-yl)-1,1,3,3-tetramethyluronium hexafluorophosphate (HATU) (73.8 mg, 0.194 mmol) were suspended in dichloromethane (5 ml). N,N-diisopropylethylamine (0.102 ml, 0.58 mmol) was added and the reaction stirred for 18 hours. The reaction was diluted with dichloromethane (10 ml), and washed with water (15 ml) then brine (15 ml), dried over $Na_2SO_4$, filtered and concentrated. The product was then purified by silica gel column chromatography, eluted with heptane/ethyl acetate=100/0 to 0/100, to recover the title product as a white solid (55 mg, 67% yield). NMR (400 MHz, $CDCl_3$) δ 1.62-1.65 (3H, d) 1.71-1.73 (6H, s) 3.83 (3H, s) 5.30-5.38 (1H, dq) 6.43-6.47 (1H, br. d) 7.53-7.54 (1H, s) 7.66-7.70 (1H, d) 8.00-8.03 (1H, dd) 8.10-8.13 (1H, d) 8.17-8.20 (1H, d) 8.25-8.26 (1H, d). MS (ESI/APCI) m/z 425 (M+H)$^+$. $[\alpha]_D$=+80.48° (c 1.05, $CH_3OH$).

Example 18a (R)-1-(5-Chloro-1-methyl-1H-pyrazol-4-yl)ethanamine dihydrochloride (Amine 10a, 50 mg, 0.215 mmol), 2-(2,2,2-trifluoro-1,1-dimethyl-ethyl)-quinoline-6-carboxylic acid (88.7 mg, 0.313 mmol) and 2-(7-aza-1H-benzotriazole-1-yl)-1,1,3,3-tetramethyluronium hexafluorophosphate (HATU) (137 mg, 0.360 mmol) were suspended in dichloromethane (5 ml). N,N-diisopropylethylamine (0.218 ml, 1.25 mmol) was added and the reaction stirred for 18 hours. The reaction was diluted with dichloromethane (10 ml), and washed with water (15 ml) then brine (15 ml), dried over $Na_2SO_4$, filtered and concentrated. The product was then purified by silica gel column chromatography, eluted with heptane/ethyl acetate=100/0 to 0/100, to recover the title product as a clear gum (80 mg, 51% yield). NMR (400 MHz, $CDCl_3$) δ 1.62-1.65 (3H, d) 1.71-1.73 (6H, s) 3.83 (3H, s) 5.30-5.38 (1H, dq) 6.43-6.47 (1H, br. d) 7.53-7.54 (1H, s) 7.66-7.70 (1H, d) 8.00-8.03 (1H, dd) 8.10-8.13 (1H, d) 8.17-8.20 (1H, d) 8.25-8.26 (1H, d). MS (ESI/APCI) m/z 425 (M+H)$^+$. $[\alpha]_D$=−42.38° (c 1.05, $CH_3OH$).

Example 19

(S)-N-(1-(5-chloro-1-methyl-1H-pyrazol-4-yl)ethyl)-2-(trifluoromethyl)quinoline-6-carboxamide and

Example 19a (R)-N-(1-(5-chloro-1-methyl-1H-pyrazol-4-yl) ethyl)-2-(trifluoromethyl) quinoline-6-carboxamide

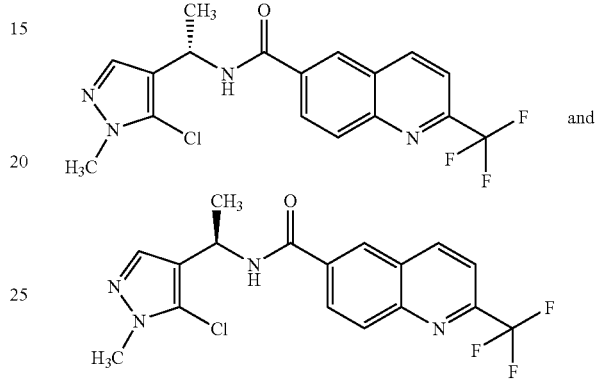

Example 19

The free base of (S)-1-(5-chloro-1-methyl-1H-pyrazol-4-yl)-ethanamine was formed by partitioning 150 mg of the hydrochloride salt (Amine 10) between saturated aqueous $NaHCO_3$ solution (20 ml) and ethyl acetate (20 ml), the organic phase was separated, washed with brine (10 ml) dried over $Na_2SO_4$, filtered and concentrated in vacuo. The free base (60 mg, 0.38 mmol), 2-trifluoromethylquinoline-6-carboxylic acid (90.7 mg, 0.376 mmol) and 2-(7-aza-1H-benzotriazole-1-yl)-1,1,3,3-tetramethyluronium hexafluorophosphate (HATU) (143 mg, 0.376 mmol) were suspended in dichloromethane (5 ml). N,N-Diisopropylethylamine (0.196 ml, 1.13 mmol) was added and the reaction stirred for 18 hours. The reaction was diluted with dichloromethane (10 ml), and washed with water (15 ml) then brine (15 ml), dried over $Na_2SO_4$, filtered and concentrated. The product was then purified by silica gel column chromatography, eluted with heptane/ethyl acetate=100/0 to 0/100, and recrystallised from tert-butyl methyl ether to recover the title product as a white solid (100 mg, 70% yield). $^1$H NMR (400 MHz, $CDCl_3$) δ 1.60-1.63 (3H, d) 3.79-3.80 (3H, s) 5.28-5.36 (1H, dq) 6.75-6.80 (1H, bd) 7.51 (1H, s) 7.73-7.76 (1H, d) 8.09-8.12 (1H, dd) 8.18-8.21 (1H, d) 8.34-8.35 (1H, d) 8.35-8.38 (1H, d). MS (ESI) m/z 383 (M+H)$^+$.

Example 19a (R)-N-(1-(5-Chloro-1-methyl-1H-pyrazol-4-ylethyl)-2-(trifluoromethyl) quinoline-6-carboxamide may be prepared by the method of Example 19, using (R)-1-(5-chloro-1-methyl-1H-pyrazol-4-yl)-ethanamine in place of the (S)-enantiomer.

Example 20

N-(1-(1-ethyl-5-methyl-1H-pyrazol-4-yl)methyl)-2-(2,2,2-trifluoro-1,1-dimethylethyl)quinoline-6-carboxamide

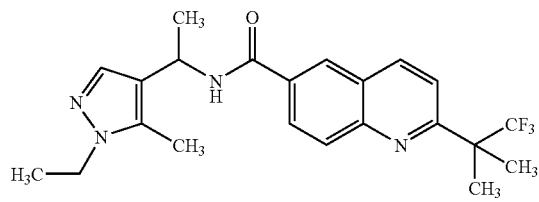

To a DMF (3 ml) solution of 1-(1-ethyl-5-methyl-1H-pyrazol-4-yl)ethanamine (95 mg, 0.62 mmol), (2,2,2-trifluoro-1,1-dimethylethyl)quinoline-6-carboxylic acid (176 mg, 0.62 mmol), HBTU (284 mg, 0.748 mmol) and triethylamine (0.434 ml, 3.12 mmol) were added and the mixture was stirred for 3 hours at room temperature. The reaction was quenched with sat. NaHCO$_3$ aq and water, and the product was extracted with EtOAc/hexane (4:1) (3×20 ml). The combined organic extracts were dried over Na$_2$SO$_4$, and concentrated in vacuo. The crude material was purified by silica gel chromatography, using EtOAc/hexane (2:1) to give the title product (31 mg, 12%) as a white solid. $^1$H NMR (300 MHz, DMSO-d$_6$) δ 1.27 (3H, t) 1.49 (3H, d), 1.71 (6H, s), 2.25 (3H, s), 4.01 (1H, q), 5.19 (1H, m), 7.44 (1H, s), 7.86 (1H, d), 8.06 (1H, d), 8.20 (1H, d), 8.51 (1H, d), 8.53 (1H, bs) 8.86 (1H, d). LCMS (ESI) RT=3.11 mins, m/z 417 (M–H)$^-$, 419 (M+H)$^+$.

Example 21

(S)-N-(1-(1-methyl-5-(trifluoromethyl)-1H-pyrazol-4-yl)ethyl)-2-(trifluoromethyl)quinoline-6-carboxamide and

Example 21a (R)-N-(1-(1-methyl-5-(trifluoromethyl)-1H-pyrazol-4-yl)ethyl)-2-(trifluoromethyl)quinoline-6-carboxamide

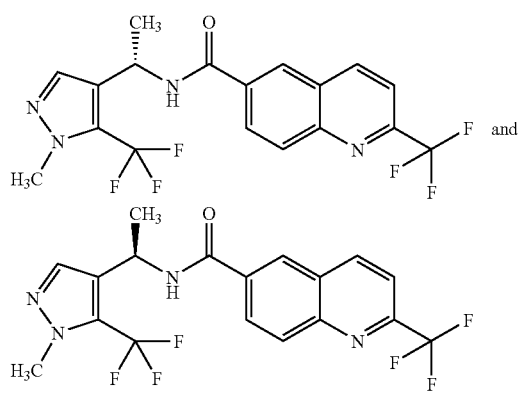

Example 21

N,N-Diisopropylethylamine (109 mg, 0.00084 mole) was added to 2-(trifluoromethyl)quinoline-6-carboxylic acid (81 mg, 0.00034 mole) in dichloromethane (4 ml) at room temperature under nitrogen. O-(7-Azabenzotriazol-1-yl) N,N,N',N'-tetramethyluronium hexafluorophosphate (106 mg, 0.00028 mole) was added and the solution stirred at RT for 5 minutes. (1S)-1-[1-methyl-5-(trifluoromethyl)-1H-pyrazol-4-yl]ethanamine dihydrochloride (75 mg, 0.00028 mole) was dissolved in dichloromethane (2 ml) and added to the reaction mixture and the solution stirred at room temperature overnight. The solution was evaporated and the residue dissolved in ethyl acetate and extracted with sodium carbonate solution (1×20 ml) and brine (2×20 ml). The organic layer was separated, dried (Na$_2$SO$_4$), filtered and evaporated to give a semi-solid. The gum was dissolved in diethylether (3×10 ml) and evaporated to give a solid. Yield 150 mg. The solid was dissolved in dichloromethane and purified using an ISCO Companion (4 g silica col. heptane to ethyl acetate:heptane 2:3). The appropriate fractions were combined and evaporated to give a white paper-like solid. The solid was suspended in diethylether (3×10 ml) and evaporated to give a white solid. Yield 90 mg, 77%. $^1$H NMR (400 MHz CD$_3$OD) δ 8.70, 8.68 (d, 1H) 8.51 (s, 1H) 8.24 (s, 2H) 5.50, 5.49, 5.47, 5.45 (q, 1H) 4.00 (s, 3H) 1.62, 1.61 (d, 3H). MS (ESI) m/z 417 (M+H)$^+$. LC-MS ESLD 100% m/z 417 (M+1). TLC Ethyl acetate:heptane 1:1 0.6 UV+ve. Mpt 182-184° C. [α]$_D$=+67.20° (c 1.25, CH$_3$OH).

Example 21a (R)-N-(1-(1-Methyl-5-(trifluoromethyl)-1H-pyrazol-4-yl)ethyl)-2-(trifluoromethyl)quinoline-6-carboxamide may be prepared by the method of Example 21, using (1R)-1-[1-methyl-5-(trifluoromethyl)-1H-pyrazol-4-yl]ethanamine dihydrochloride in place of the corresponding (S)-enantiomer.

Example 22

(S)-N-(1-(1-methyl-5-(trifluoromethyl)-1H-pyrazol-4-yl)ethyl)-2-(1,1,1-trifluoro-2-methylpropan-2-yl)quinoline-6-carboxamide and

Example 22a (R)-N-(1-(1-methyl-5-(trifluoromethyl)-1H-pyrazol-4-yl)ethyl)-2-(1,1,1-trifluoro-2-methylpropan-2-yl)quinoline-6-carboxamide

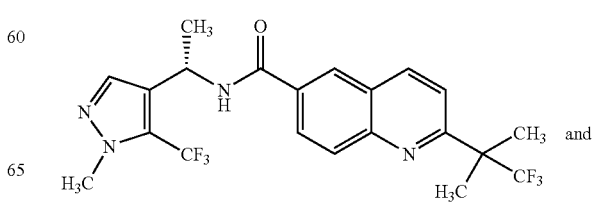

-continued

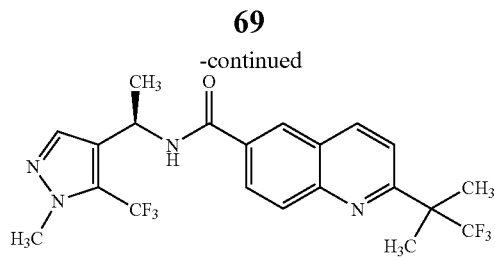

Example 22

N,N-Diisopropylethylamine (146 mg, 0.0013 mole) was added to 2-(2,2,2-trifluoro-1,1-dimethylethyl)quinoline-6-carboxylic acid (106 mg, 0.00038 mole) in dichloromethane (4 ml) at room temperature under nitrogen. O-(7-Azabenzotriazol-1-yl) N,N,N',N'-tetramethyluronium hexafluorophosphate (143 mg, 0.00038 mole) was added and the solution stirred for 5 mins.

(1S)-1-[1-Methyl-5-(trifluoromethyl)-1H-pyrazol-4-yl] ethanamine dihydrochloride (100 mg, 0.00038 mole) was added to the reaction mixture and the solution stirred at room temperature overnight. The solution was evaporated and the residue dissolved in ethyl acetate and washed with 10% sodium carbonate solution (2×20 ml) and brine (3×20 ml). The organic layer was separated, dried (Na$_2$SO$_4$), filtered and evaporated to give a colourless gum. Yield 170 mgs. The gum was dissolved in dichloromethane and purified using an ISCO Companion (12 g silica col. heptane to ethyl acetate:heptane 2:3). The appropriate fractions were combined and evaporated to give a colourless foam. Yield 150 mg, 87%. $^1$H NMR (400 MHz CD$_3$OD) δ 8.41-8.39 (m, 2H) 8.13 (s, 2H) 7.83, 7.81 (d, 1H) 7.67 (s, 1H) 5.51, 5.49, 5.47, 5.45 (q, 1H) 4.00 (s, 3H) 1.75 (s, 6H) 1.62, 1.60 (d, 3H). MS (ESI) m/z 459 (M+H)$^+$. LC-MS 100% ESLD m/z 459 (M+H)$^+$. TLC Ethyl acetate:heptane 1:1 0.6 UV+ve. [α]$_D$=+73.91° (c 2.07, CH$_3$OH).

Example 22a

N,N-Diisopropylethylamine (110 mg, 0.00085 mole) was added to 2-(2,2,2-trifluoro-1,1-dimethylethyl)quinoline-6-carboxylic acid (80.2 mg, 0.00028 mole) in dichloromethane (4 ml) at room temperature under nitrogen. O-(7-Azabenzotriazol-1-yl) N,N,N',N'-tetramethyluronium hexafluorophosphate (108 mg, 0.00028 mole) was added and the solution stirred for 5 mins. (1R)-1-[1-Methyl-5-(trifluoromethyl)-1H-pyrazol-4-yl]ethanamine dihydrochloride (75.2 mg, 0.00028 mole) was added to the reaction mixture and the solution stirred at room temperature overnight. The solution was evaporated and the residue dissolved in ethyl acetate and washed with 10% sodium carbonate solution (2×20 ml) and brine (3×20 ml). The organic layer was separated, dried (Na$_2$SO$_4$), filtered and evaporated to give a colourless gum. The gum was dissolved in dichloromethane and purified using an ISCO Companion (4 g silica column, heptane to ethyl acetate:heptane 1:1). The appropriate fractions were combined and evaporated to give a colourless foam. Yield 60 mg 46% $^1$H NMR (400 MHz CD$_3$OD) 8.41-8.39 (m, 2H) 8.13 (s, 2H) 7.83, 7.81 (d, 1H) 7.66 (s, 1H) 5.50, 5.48, 5.47, 5.45 (q, 1H) 4.00 (s, 3H) 1.75 (s, 6H) 1.62, 1.60 (d, 3H). MS (ESI) m/z 459 (M+H)$^+$ LC-MS 100% ESLD m/z 459 (M+H)$^+$ TLC Ethyl acetate:heptane 1:1 0.6 UV+ve [α]$_D$=−71.25° (c 1.0, CH$_3$OH)

Example 23

(R)-N-(1-(1,5-dimethyl-1H-pyrazol-4-yl)ethyl)-2-(trifluoromethyl) quinoline-6-carboxamide

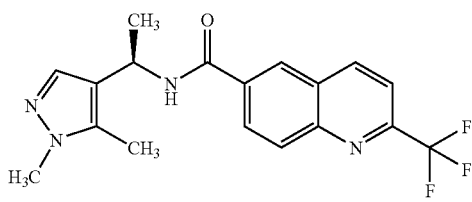

2-Trifluoromethylquinoline-6-carboxylic acid (100 mg, 0.415 mmol) was dissolved in DCM (10 mL) and N,N-di-isopropylethylamine (Hunig's base, 268 µl, 1.54 mmol) was added. HATU (158 mg, 0.415 mmol) was added followed by (1R)-1-[1,5-dimethyl-1H-pyrazol-4-yl]ethanamine dihydrochloride (88 mg, 0.415 mmol) and the solution was stirred at RT overnight. The reaction mixture was concentrated and the residue was dissolved in EtOAc (65 mL) then partitioned with sat. aq. NaHCO$_3$ (2×20 mL) and then brine (30 mL). The organic layer dried over MgSO$_4$, filtered and solvent removed under reduced pressure to give a golden oil/gum. The product was purified using an ISCO (12 g column), eluting with EtOAc:Heptane (5:95 increasing to 100:0). Fractions containing pure product concentrated under reduced pressure to give a white foamy solid, 150 mg, yield=41%. $^1$H NMR (400 MHz, CD$_3$OD) δ 8.68 (1H, d), 8.47-8.49 (1H, m), 8.20-8.23 (2H, m), 7.92 (1H, d), 7.48 (1H, s), 5.29 (1H, q) 3.76 (3H, s), 2.33 (3H, s) and 1.61 (3H, d). LCMS (2 min run): UV (1.37 min, 82%); ELSD (1.37 min, 100%). Mass ion: 363=MH$^+$

Example 24

6-tert-butyl-N-[1-(1,5-dimethyl-1H-pyrazol-4-yl)ethyl]-2-naphthamide

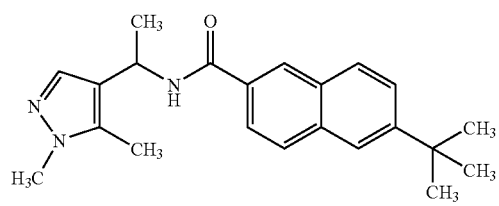

Prepared by the method of Example 1 using Amine 1 and Carboxylic Acid 2. $^1$H NMR (300 MHz, DMSO-d$_6$) δ 1.39 (9H, s), 1.49 (3H, d, J=8.1 Hz), 2.24 (3H, s), 3.69 (3H, s), 5.14-5.20 (1H, m), 7.40 (1H, s), 7.70 (3H, d, J=10.8 Hz), 7.87-7.96 (4H, m), 8.39 (1H, s), 8.69 (1H, d, J=8.1 Hz). MS (ESI) m/z 348 (M−H)$^-$, 350 (M+H)$^+$.

Example 25

6-tert-butyl-N-[(3,5-dimethyl-1H-pyrazol-4-yl)methyl]-2-naphthamide

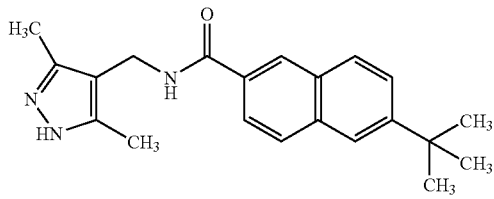

Prepared by the method of Example 1 using (3,5-dimethyl-1H-pyrazol-4-yl)methanamine and Carboxylic Acid 2. $^1$H-NMR (300 MHz, CDCl$_3$) δ 1.42 (9H, s), 2.32 (3H, s), 4.49 (2H, d, J=6.0 Hz), 6.13 (1H, brs), 7.61-7.65 (1H, m), 7.76-7.87 (4H, m), 8.22 (1H, s). MS (ESI) m/z 334 (M−H)$^−$, 336 (M+H)$^+$.

Example 26

6-tert-butyl-N-[(1,3-dimethyl-1H-pyrazol-4-yl)methyl]-2-naphthamide

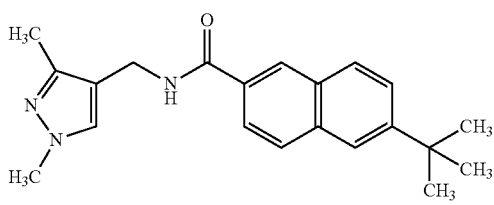

Prepared by the method of Example 1 using (1,3-dimethyl-1H-pyrazol-4-yl)methanamine and Carboxylic Acid 2. $^1$H-NMR (300 MHz, CDCl$_3$) δ 1.42 (9H, s), 2.30 (3H, s), 3.83 (3H, s), 4.50 (2H, d, J=6.0 Hz), 6.26 (1H, br. s), 7.36 (1H, s), 7.62-7.66 (1H, m), 7.76-7.87 (4H, m), 8.22 (1H, s). MS (ESI) m/z 334 (M−H)$^−$, 336 (M+H)$^+$.

Example 27

6-tert-butyl-N-[(1,5-dimethyl-1H-pyrazol-4-yl)methyl]-2-naphthamide

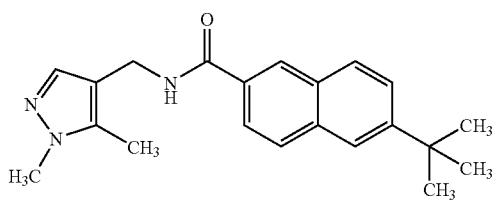

Prepared by the method of Example 1 using 1-(1,5-dimethyl-1H-pyrazol-4-yl)methanamine and Carboxylic Acid 2. $^1$H NMR (300 MHz, DMSO-d$_6$) δ 1.38 (9H, s), 2.27 (3H, s), 3.69 (3H, s), 4.29 (2H, d, J=5.9 Hz), 7.32 (1H, s), 7.69 (1H, dd, J=8.8, 2.2 Hz), 7.85-7.98 (4H, m), 8.39 (1H, s), 8.85 (1H, t, J=5.5 Hz). Prep-HPLC (basic 32-68, RT=3.52 min).

Example 28

6-tert-butyl-N-(1-(1,5-dimethyl-1H-pyrazol-4-yl)propyl)-2-naphthamide

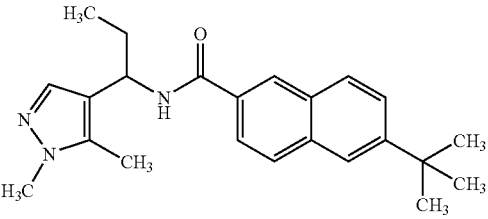

Prepared by the method of Example 1 using Amine 5 and Carboxylic Acid 2. $^1$H NMR (300 MHz, CDCl$_3$) δ 1.01 (3H, t, J=6.0 Hz), 1.42 (9H, s), 1.90-2.09 (2H, m), 2.31 (3H, s), 3.79 (3H, s), 5.06-5.14 (1H, m), 6.22 (1H, brd, J=6.0 Hz), 7.44 (1H, s), 7.61-7.64 (1H, m), 7.75-7.86 (4H, m), 8.20 (1H, s). MS (ESI) m/z 362 (M−H)$^−$, 364 (M+H)$^+$.

Example 29

N-(1-(1,5-dimethyl-1H-pyrazol-4-yl)ethyl)-6-(trifluoromethyl)-2-naphthamide

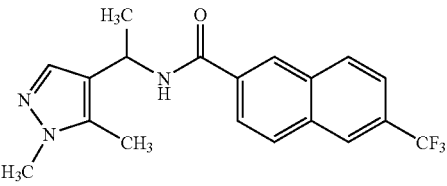

Prepared by the method of Example 1 using Amine 1 and 6-(trifluoromethyl)-2-naphthoic acid. $^1$H NMR (300 MHz, DMSO-d$_6$) δ 1.49 (3H, d, J=6.0 Hz), 2.24 (3H, s), 3.69 (3H, s), 5.13-5.22 (1H, m), 7.41 (1H, s), 7.80-7.84 (1H, m), 8.04-8.08 (1H, m), 8.19-8.27 (2H, m), 8.48 (1H, s), 8.55 (1H, s), 8.83 (1H, brd, J=9.0 Hz). MS (ESI) m/z 360 (M−H)$^−$, 362 (M+H)$^+$.

Example 30

N-[(1R)-1-(1,5-dimethyl-1H-pyrazol-4-yl)ethyl]-6-(1-methylcyclopropyl)-2-naphthamide

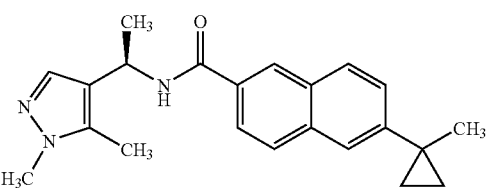

Prepared by the method of Example 1 using Amine 2 and Carboxylic acid 6. $^1$H NMR (270 MHz, DMSO-d$_6$) δ 0.79-0.92 (2H, m), 0.92-1.04 (2H, m), 1.42-1.55 (6H, m, including 3H, s, 1.49 ppm), 2.23 (3H, s), 3.68 (3H, s), 5.16 (1H, m), 7.33-7.44 (2H, m), 7.80 (1H, s), 7.84-7.95 (3H, m), 8.37 (1H, s), 8.68 (1H, d, J=8.6 Hz). MS (ESI): m/z 348 (M+H)+.

Example 31

N-[(1R)-1-(1,5-dimethyl-1H-pyrazol-4-yl)ethyl]-6-(2,2,2-trifluoro-1-hydroxy-1-methylethyl)-2-naphthamide and Example 32

N-[(1R)-1-(1,5-dimethyl-1H-pyrazol-4-yl)ethyl]-6-[(1R)-2,2,2-trifluoro-hydroxy-1-methylethyl]-2-naphthamide

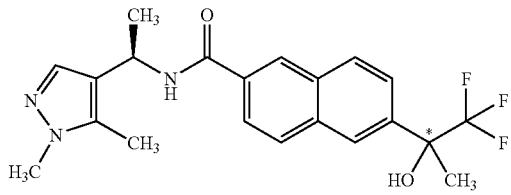

To a DMF (1.0 ml) solution of (1R)-1-(1,5-dimethyl-1H-pyrazol-4-yl)ethanamine hydrochloride (Amine 2) (75 mg, 0.352 mmol), (R,S)-6-(2,2,2-trifluoro-1-hydroxy-1-methylethyl)-2-naphthoic acid (Carboxylic Acid 7) (100 mg, 0.352 mmol), HBTU (160 mg, 0.422 mmol) and triethylamine (0.245 ml, 1.76 mmol) were added and the mixture was stirred for 2 hours at room temperature. The reaction was quenched with sat. NaHCO3 aq and water, and the product was extracted with EtOAc. The organic extract was dried over Na2SO4, and concentrated in vacuo. The mixture was applied to a silica gel column chromatography and eluted with hexane/ethyl acetate (1:2) to furnish the mixture of diastereoisomers (Example 31, 77 mg, 54% yield) as a white solid. The product was purified by HPLC (column: DAICEL CHIRAL-PAK AD-H 250 mm×20 mm, n-Hexane/Ethanol/Diethylamine=80/20/0.1 as eluent) to give the title product (Example 32, 5.7 mg, 2nd peak, retention time: 17.9 min) as a white solid as a single diastereoisomer. 1H NMR (300 MHz, CDCl3) δ 1.64 (3H, d, J=6.6 Hz), 1.89 (3H, s), 2.32 (3H, s), 3.80 (3H, s), 5.31-5.39 (1H, m), 6.34-6.38 (1H, m), 7.54 (1H, s), 7.70-8.09 (5H, m), 8.24 (1H, s). MS (ESI): m/z 406 (M+H)+.

Example 32a

N-[(1R)-1-(1,5-dimethyl-1H-pyrazol-4-yl)ethyl]-6-[(1S)-2,2,2-trifluoro-1-hydroxy-1-methylethyl]-2-naphthamide

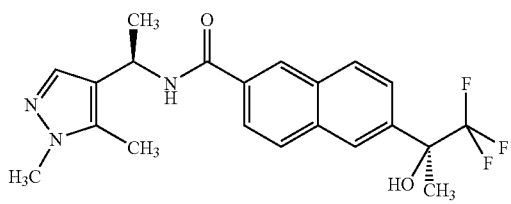

To a DMF (4 ml) solution of Amine 2 ((1R)-1-(1,5-dimethyl-1H-pyrazol-4-yl)ethanamine dihydrochloride, 74.6 mg, 0.352 mmol), Carboxylic Acid 7 (6-(2,2,2-trifluoro-1-hydroxy-1-methylethyl)-2-naphthoic acid, 100 mg, 0.352 mmol), HBTU (160 mg, 0.422 mmol) and triethylamine (0.245 ml, 1.76 mmol) were added and the mixture was stirred for 24 hours at room temperature. The reaction was quenched with sat. NaHCO3 aq and water, and the product extracted with EtOAc 3 times. The combined organic extracts were dried over Na2SO4, and concentrated in vacuo. The crude material was purified by silica gel column chromatography (Ethylacetate:Hexane=2:1) to give the product as a mix of diastereomers. These were purified by chiral HPLC to give the title product as a white amorphous solid (18.3 mg, 12.8% yield). 1H NMR (300 MHz, CDCl3) δ 1.64-1.66 (3H, d), 1.88-1.89 (3H, s) 2.30-2.33 (3H, s) 3.79-3.81 (3H s) 5.31-5.36 (1H, m) 6.33-6.38 (1H, bd) 7.54 (1H, s) 7.72-7.76 (1H, dd) 7.87-7.90 (1H, d) 7.91-7.94 (2H, dt) 8.08-8.09 (1H, s) 8.23-8.24 (1H, s) MS (ESI) m/z 406 (M+H)+.

Example 33

N-[1-(1,5-dimethyl-1H-pyrazol-4-yl)ethyl]-6-(2,2,2-trifluoro-1-methoxy-1-methylethyl)-2-naphthamide

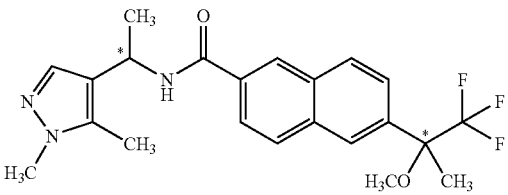

Prepared by the method of Example 1 from Amine 2 and Carboxylic Acid 8. 1H NMR (300 MHz, CDCl3) δ 1.65 (3H, d, J=5.8 Hz), 1.90 (3H, s), 2.31 (3H, s), 3.28 (3H, s), 3.80 (3H, s), 5.31-5.36 (1H, m), 6.27-6.29 (1H, m), 7.51 (1H, s), 7.71-7.98 (5H, m), 8.26 (1H, s). MS (ESI): m/z 420 (M+H)+.

Example 34

6-tert-butyl-N-[(1,5-dimethyl-1H-pyrazol-4-yl)methyl]quinoline-2-carboxamide

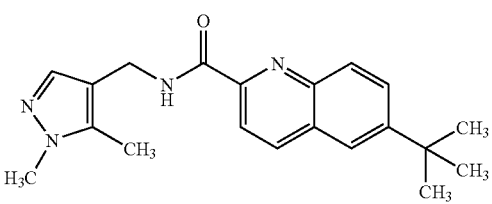

Prepared by the method of Example 1 using 1-(1,5-dimethyl-1H-pyrazol-4-yl)methanamine and Carboxylic Acid 3. 1H NMR (300 MHz, DMSO-d6) δ 1.39 (9H, s), 2.28 (3H, s), 3.68 (3H, s), 4.33 (2H, d, J=6.6 Hz), 7.34 (1H,$), 7.93-8.15

(4H, m), 8.51 (1H, d, 8.8 Hz), 9.04 (1H, t, J=6.24 Hz). Prep-HPLC (basic 32-68, RT=3.72 min) MS (ESI) m/z 337 (M+H)⁺.

Example 35

6-tert-butyl-N-((1,3,5-trimethyl-1H-pyrazol-4-yl)methyl)-2-naphthamide

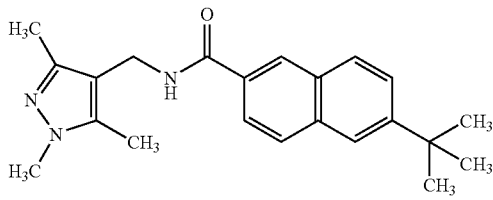

Prepared by the method of Example 1 using (1,3,5-trimethyl-1H-pyrazol-4-yl)methanamine and Carboxylic Acid 2. ¹H NMR (300 MHz, CDCl₃) δ 1.42 (9H, s), 2.27 (6H, s), 3.74 (3H, s), 4.46 (2H, d, J=6.0 Hz), 6.10 (1H, brs), 7.61-7.65 (1H, m), 7.75-7.86 (4H, m), 8.21 (1H, s). MS (ESI) m/z 348 (M−H)⁻, 350 (M+H)⁺

Example 36

6-tert-butyl-N-[(1H-pyrazol-4-yl)methyl]-2-naphthamide

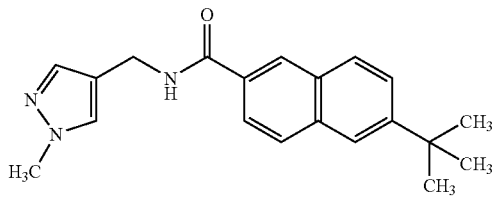

Prepared by the method of Example 1 using (1-methyl-1H-pyrazol-4-yl)methanamine and Carboxylic acid 2. ¹H-NMR (300 MHz, CDCl₃) δ 1.42 (9H, s), 3.89 (3H, s), 4.55 (2H, d, J=6.0 Hz), 6.43 (1H, brs), 7.45 (1H, s), 7.52 (1H, s), 7.61-7.65 (1H, m), 7.79-7.86 (4H, m), 8.23 (1H, s). MS (ESI) m/z 320 (M−H)⁻, 322 (M+H)⁺

Example 37

N-[1-(1,5-dimethyl-1H-pyrazol-4-yl)ethyl]-6-(1-hydroxy-1-methylethyl)-2-naphthamide

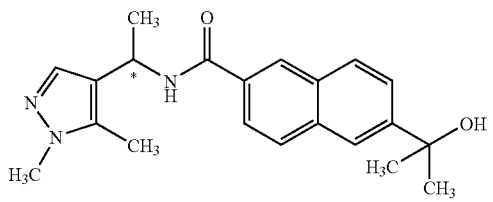

To a DMF (3 ml) solution of 6-(1-Hydroxy-1-methylethyl)-naphthalene-2-carboxylic acid (U.S. Pat. No. 4,638,087, published 20 Jan. 1987, 95 mg, 0.413 mmol), Amine 9 (1-(5-Methyl-1H-pyrazol-4-yl)ethanamine dihydrochloride, 95 mg, 0.352 mmol), HBTU (188 mg, 0.495 mmol) and triethylamine (0.173 ml, 1.24 mmol) were added and the mixture was stirred for 24 hours at room temperature. The reaction was quenched with sat. NaHCO₃ aq and water, and the product extracted with EtOAc 3 times. The combined organic extracts were dried over Na₂SO₄, and concentrated in vacuo. The crude material was purified by silica gel column chromatography (Ethylacetate:Hexane=2:1) to give the title product as a white solid (84.4 mg, 58.2% yield). ¹H NMR (300 MHz, DMSO-d₆) δ 1.46-1.49 (3H, d), 1.50-1.53 (6H, s) 2.22-2.24 (3H, s) 3.67-3.68 (3H s) 5.13-5.20 (2H, m) 7.38-7.39 (1H, s), 7.69-7.72 (1H, d) 7.81-8.00 (4H, m) 8.39-8.40 (1H, s) 8.68-8.72 (1H, d). MS (ESI) m/z 352 (M+H)⁺.

Example 38

N-((1S)-1-(5-chloro-1-methyl-1H-pyrazol-4-yl)methyl)-2-(pentafluoroethyl)quinoline-6-carboxamide

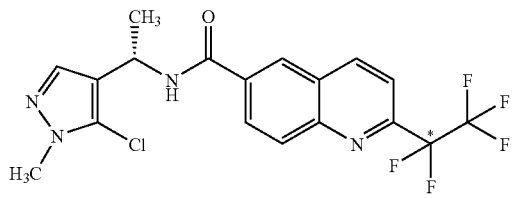

(S)-1-(5-Chloro-1-methyl-1H-pyrazol-4-yl)-ethanamine dihydrochloride (36 mg, 0.155 mmol), 2-pentafluoroethylquinoline-6-carboxylic acid (45 mg, 0.16 mmol) and 2-(7-aza-1H-benzotriazole-1-yl)-1,1,3,3-tetramethyluronium hexafluorophosphate (HATU) (65 mg, 0.171 mmol) were suspended in dichloromethane (5 ml). N,N-Diisopropylethylamine (0.108 ml, 0.62 mmol) was added and the reaction stirred for 18 hours. The reaction was diluted with dichloromethane (15 ml), and washed with water (15 ml), the organics were concentrated to give the crude product. The product was then purified by ISCO Biotage column using 0-100% EtOAc in Heptane to give the title product as a clear gum (55 mg, 70% yield). NMR (400 MHz, CD₃OD) δ 1.60-1.63 (3H, d) 3.81 (3H, s) 5.28 (1H, dq) 7.61 (1H, s) 7.92 (1H, d) 8.23 (2H, dd) 8.50 (1H, s) 8.67 (1H, d) 8.97 (1H bd). LCMS: Retention time: 1.55 mins, MS (ESI)m/z 433 (M+H⁺).

Method for Assessing Biological Activities
Human VR1 Antagonist Assay

VR1 antagonistic activity can be determined by the Ca²⁺ imaging assay using human VR1 highly expressing cells. The cells that highly express human VR1 receptors are obtainable from several different conventional methods. The one standard method is cloning from human Dorsal Root Ganglion (DRG) or kidney according to the methods such as described in the journal article; Nature, 389, pp 816-824, 1997. Alternatively VR1 receptors highly expressing human keratinocytes are also known and published in the journal article (Biochemical and Biophysical Research Communications, 291, pp 124-129, 2002). In this article, human keratinocytes demonstrated VR1 mediated intracellular Ca²⁺ increase by addition of capsaicin. Furthermore, the method to up regulate human VR1 gene, which is usually a silent gene or don't produce detectable level of VR1 receptors, is also available to obtain propriety cells. Such genetic modification method was described in detail; Nat. Biotechnol., 19, pp 440-445, 2001.

The cells that express human VR1 receptors were maintained in culture flask at 37° C. in an environment containing 5% $CO_2$ until use in the assay. The intracellular $Ca^{2+}$ imaging assay to determine VR1 antagonistic activities were done by following procedures.

The culture medium was removed from the flask and fura-2/AM fluorescent calcium indicator was added to the flask at a concentration of 5 µM in the medium. The flask was placed in $CO_2$ incubator and incubated for 1 hour. Then the cells expressing the human VR1 receptors were detached from the flask follow by washing with phosphate buffer saline, PBS(−) and re-suspended in assay buffer. The 80 µl of aliquot of cell suspension ($3.75 \times 10^5$ cells/ml) was added to the assay plate and the cells were spun down by centrifuge (950 rpm, 20° C., 3 minutes).

Compounds of the examples were tested in the Human VR1 antagonist assay described above. The inhibition concentration 50% ($IC_{50}$) values are presented in the following table.

TABLE 1

| Example No. | $IC_{50}$ (nM) |
|---|---|
| 1 | 25.2 |
| 2 | 261 |
| 3 | 322 |
| 4 | 607 |
| 5 | 44.1 |
| 6 | 26.6 |
| 7 | 145 |
| 8 | 66.0 |
| 9 | 323 |
| 11 | 16.4 |
| 12 | 79.9 |
| 13 | 313 |
| 14 | 63.7 |
| 15 | 71.7 |
| 16 | 28.9 |
| 17 | 124 |
| 18 | 17.97 |
| 18a | 3 |
| 23 | 121 |
| 24 | 23 |
| 25 | 118 |
| 26 | 443 |
| 27 | 73 |
| 28 | 57.4 |
| 29 | 189 |
| 30 | 20.1 |
| 31 | 177 |
| 32 | 52.7 |
| 32a | 3190 |
| 33 | 139 |
| 34 | 254 |
| 35 | 1870 |
| 36 | 3480 |
| 37 | 1000 |
| capsazepin | 237-455 |

Capsaicin Stimulation Assay

The capsaicin-induced changes in the intracellular calcium concentration were monitored using FDSS 6000 (Hamamatsu Photonics, Japan), a fluorometric imaging system. The cell suspension in Krebs-Ringer HEPES (KRH) buffer (115 mM NaCl, 5.4 mM KCl, 1 mM $MgSO_4$, 1.8 mM $CaCl_2$, 11 mM D-Glucose, 25 mM HEPES, 0.96 mM $Na_2HPO_4$, pH 7.3) were pre-incubated with varying concentrations of the test compounds or KRH buffer (buffer control) for 15 minutes at room temperature under the dark condition. Then capsaicin solution, which gives 300 nM in assay mixture, was automatically added to the assay plate by the FDSS 6000.

Acid Stimulation Assay

The Acid-induced changes in the intracellular calcium concentration were monitored using FDSS 6000 (Hamamatsu Photonics, Japan), a fluorometric imaging system. The cell suspension in resting buffer (HBSS supplemented with 10 mM HEPES, pH 7.4) were pre-incubated with varying concentrations of the test compounds or resting buffer (buffer control) for 15 minutes at room temperature under the dark condition. The cells were automatically added the stimulating solution (HBSS supplemented with MES, final assay buffer pH5.8) by the FDSS 6000. The $IC_{50}$ values of VR1 antagonists were determined from the half of the increase demonstrated by buffer control samples after acidic stimulation.

Determination of Antagonist Activity

The monitoring of the changes in the fluorescence signals ($\lambda ex=340$ nm/380 nm, $\lambda em=510$-520 nm) was initiated at 1 minute prior to the addition of capsaicin solution or acidic buffer and continued for 5 minute. The $IC_{50}$ values of VR1 antagonists were determined from the half of the increase demonstrated by buffer control samples after agonist stimulation.

Human VR1 Agonist Assay

The cells that express human VR1 receptors were maintained in culture flask at 37° C. in an environment containing 5% $CO_2$ until use in the assay. The intracellular $Ca^{2+}$ imaging assay to determine VR1 agonistic activities were done by following procedures. The culture medium was removed from the flask and fura-2/AM fluorescent calcium indicator was added to the flask at a concentration of 5 µM in the medium. The flask was placed in $CO_2$ incubator and incubated for 1 hour. Then the cells expressing the human VR1 receptors were detached from the flask follow by washing with phosphate buffer saline, PBS(−) and re-suspended in Krebs-Ringer HEPES buffer (KRH): 115 mM NaCl, 5.4 mM KCl, 1 mM $MgSO_4$, 1.8 mM $CaCl_2$, 11 mM D-Glucose, 25 mM HEPES, 0.96 mM $Na_2HPO_4$, pH 7.3.

96-Well Format Assay

The test compound-induced changes in the intracellular calcium concentration were monitored using FDSS 6000 (Hamamatsu Photonics, Japan), a fluorometric imaging system. The 80 µL of aliquot of cell suspension ($3.75 \times 10^5$ cells/mL) in KRH buffer was distributed into the 96-well plate, and then this assay plate was placed on the FDSS6000. Finally 20 µL of varying concentrations of the test compounds or KRH buffer (buffer control) or 1 µM capsaicin (maximum response control) were automatically added to the assay plate by the FDSS 6000.

384-well format assay

The 30 µL of aliquot of cell suspension ($8 \times 10^5$ cells/mL) in KRH buffer was distributed into the 384-well plate, and then this assay plate was placed on the FDSS6000. Finally 15 µL of varying concentrations of the test compounds or KRH buffer (buffer control) or 2 µM capsaicin (maximum response control) were automatically added to the assay plate by the FDSS 6000.

Determination of Agonist Activity

The monitoring of the changes in the fluorescence signals ($\lambda ex=340$ nm/380 nm, $\lambda em=510$-520 nm) was initiated 1 min (96-well format) or 15 seconds (384-well format) prior to the addition of test compounds and continued for 5 minute. The $EC_{50}$ values of compounds were determined from the maximum response of test compounds. The $E_{max}$ values were determined as a percentage of 1 µM (96-well format) or 2 µM (384-well format) capsaicin-induced response.

Chronic Constriction Injury Model (CCI Model)

Male Sprague-Dawley rats (270-300 g; B.W., Charles River, Tsukuba, Japan) were used. The chronic constriction injury (CCI) operation was performed according to the method described by Bennett and Xie (Bennett, G. J. and Xie, Y. K. Pain, 33:87-107, 1988). Briefly, animals were anesthetized with sodium pentobarbital (64.8 mg/kg, i.p.) and the left common sciatic nerve was exposed at the level of the middle of the thigh by blunt dissection through biceps femoris. Proximal to the sciatic's trifurcation was freed of adhering tissue and 4 ligatures (4-0 silk) were tided loosely around it with about 1 mm space. Sham operation was performed as same as CCI surgery except for sciatic nerve ligation. Two weeks after surgery, mechanical allodynia was evaluated by application of von Frey hairs (VFHs) to the plantar surface of the hind paw. The lowest amount of force of VFH required to elicit a response was recorded as paw withdrawal threshold (PWT). VFH test was performed at 0.5, 1 and 2 hr post-dosing. Experimental data were analyzed using Kruskal-Wallis test followed by Dunn's test for multiple comparisons or Mann-Whitney U-test for paired comparison.

Mono-Iodoacetate (MIA)-Induced OA Model

Male 6-weeks-old Sprague-Dawley (SD, Japan SLC or Charles River Japan) rats were anesthetized with pentobarbital. Injection site (knee) of MIA was shaved and cleaned with 70% EtOH. Twenty-five µl of MIA solution or saline was injected in the right knee joint using a 29G needle. The effect of joint damage on the weight distribution through the right (damaged) and left (untreated) knee was assessed using an incapacitance tester (Linton Instrumentation, Norfolk, UK). The force exerted by each hind limb was measured in grams. The weight-bearing (WB) deficit was determined by a difference of weight loaded on each paw. Rats were trained to measure the WB once a week until 20 days post MIA-injection. Analgesic effects of compounds were measured at 21 days after the MIA injection. Before the compound administration, the "pre value" of WB deficit was measured. After the administration of compounds, attenuation of WB deficits was determined as analgesic effects.

Complete Freund's Adjuvant (CFA) Induced Thermal and Mechanical Hyperalgesia in Rats Thermal Hyperalgesia Male 6-week-old SD rats were used. Complete Freund's adjuvant (CFA, 300 µg of *Mycobacterium Tuberculosis* H37RA (Difco, MI) in 100 µL of liquid paraffin (Wako, Osaka, Japan)) was injected into the plantar surface of hind paw of the rats. Two days after CFA-injection, thermal hyperalgesia was determined by method described previously (Hargreaves et al., 1988) using the plantar test apparatus (Ugo-Basil, Varese, Italy). Rats were adapted to the testing environment for at least 15 min prior to any stimulation. Radiant heat was applied to the plantar surface of hind paw and paw withdrawal latencies (PWL, seconds) were determined. The intensity of radiant heat was adjusted to produce the stable PWL of 10 to 15 seconds. The test compound was administered in a volume of 0.5 mL per 100 g body weight. PWL were measured after 1, 3 or 5 hours after drug administration.

Mechanical Hyperalgesia

Male 4-week-old SD rats were used. CFA (300 µg of *Mycobacterium Tuberculosis* H37RA (Difco, MI) in 100 µL of liquid paraffin (Wako, Osaka, Japan)) was injected into the plantar surface of hind paw of the rats. Two days after CFA-injection, mechanical hyperalgesia was tested by measuring paw withdrawal threshold (PWT, grams) to pressure using the analgesy-Meter (Ugo-Basil, Varese, Italy). The animals were gently restrained, and steadily increasing pressure was applied to the dorsal surface of a hind paw via a plastic tip. The pressure required to elicit paw withdrawal was determined. The test compound was administered in a volume of 0.5 mL per 100 g body weight. PWT were measured after 1, 3 or 5 hours after drug administration.

Parallel Artificial Membrane Permeation Assay (PAMPA)

Experiments were performed in 96-well acceptor and donor plates. Such 96-well system was described in *Journal of Medicinal Chemistry*, 1998, vol. 41, No. 7, 1007-1010. 4% phosphatidylcholine and 1% stearic acid in dodecane were used as artificial membrane material. The acceptor plate (96 well hydrophobic filter plate (MAIP N45, Millipore)) was prepared by adding 5 µL of artificial membrane material on the top of the filter and the plate was filled with 250 µL of 2-(N-morpholino)ethanesulfonic acid (MES) buffered Hank's balanced salt solution (HBSS) (pH 6.5). The donor plate (Transport Receiver plate (MATRNPS50, Millipore)) was filled with 300 µL of MES buffered HBSS (pH 6.5) containing 10 µM of the test compounds. The acceptor plate was placed onto the donor plate to form a "sandwich" and was incubated at 30° C. for 2.5 hours. After the incubation period, acceptor, donor and initial donor solution (reference) were analyzed via LC-MS/MS. Data were reported as the effective permeability value in $cm \times 10^6$/sec and the membrane retention value.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit and ARVO SX plate reader (Wallac). All the manipulation, stock solution and equipment were kept on ice at all time. For saturation assays, experiments were conducted in a total volume of 200 µl. Saturation was determined by incubating 20 µl of [$^3$H]-dofetilide and 160 µl of membrane homogenates (20-30 µg protein per well) for 60 min at room temperature in the absence or presence of 10 µM dofetilide at final concentrations (20 µl) for total or nonspecific binding, respectively. All incubations were terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM $MgCl_2$, 10 mM KCl so that the final DMSO concentration became equal to 1%. Compounds were dispensed in triplicate in assay plates (4 µl). Total binding and nonspecific binding wells were set up in 6 wells as vehicle and 10 µM dofetilide at final concentration, respectively. The radioligand was prepared at 5.6× final concentration and this solution was added to each well (36 µl). The assay was initiated by addition of YSi poly-L-lysine Scintillation Proximity Assay (SPA) beads (50 µl, 1 mg/well) and membranes (110 µl, 20 µg/well). Incubation was continued for 60 min at room temperature.

Plates were incubated for a further 3 hours at room temperature for beads to settle. Receptor-bound radioactivity was quantified by counting Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical Journal, 74, pp 230-241). Before the day of experimentation, the cells were harvested from culture flasks and plated onto glass coverslips in a standard Minimum Essential Medium (MEM) medium with 10% Fetal Calf Serum (FCS). The plated cells were stored in an incubator at 37° C. maintained in an atmosphere of 95% $O_2$/5% $CO_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15M$\Omega$ and seal resistances>1G$\Omega$ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 1000 ms. This was followed by a descending voltage ramp (rate 0.5 mV msec$^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There was a subsequent wash period of a 10-20 min to assess reversibility. Finally, the cells were exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under vehicle control conditions and in the presence of drug. Percent decrease of $I_N$ in each experiment was obtained by the normalized current value using the following formula: $I_N=(1-I_D/I_C)\times100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Single Point Drug-Drug Interaction Cocktail of Substrates Assay (cDDI)

Test compounds (3 μM) were pre-incubated in 0.1 mg/mL human liver microsomes with 1 mM $MgCl_2$, 1 mM NADP+, 5 mM isocitric acid, and 1 U/mL isocitric dehydrogenase in 100 mM potassium phosphate buffer (pH 7.4) at 37° C. on a number of 96-well plates. After 5 minutes pre-incubation, reaction was initiated by addition of substrate cocktail including all substrates shown in the following Table. After 8 minutes of incubation, a plate was removed from the incubator and the reaction was terminated with one incubation volume of acetonitrile. The metabolites concentrations in supernatant were measured by LC/MS/MS system. The percent inhibition for each CYPs was calculated using the following equation:

% Inhibition=(1−(the amount of the metabolite with the test compound)/(Average amount of the metabolite without the test compound))×100

TABLE 2

Conditions for drug-drug interaction assay

| CYP | Substrate | Substrate Conc. (μM) | Metabolite |
| --- | --- | --- | --- |
| 1A2 | Tacrine | 2 | 1'-Hydroxytacrine |
| 2C9 | Diclofenac | 5 | 4'-Hydroxydiclofenac |
| 2C19 | S-Mephenytoin | 40 | 4'-Hydroxymephenytoin |
| 2D6 | Dextromethorphan | 5 | Dextrorphan |
| 3A | Midazolam | 2 | 1'-Hydroxymidazolam |

Intrinsic Clearance

Test compounds (1 μM) were incubated with 1 mM $MgCl_2$, 1 mM NADP+, 5 mM isocitric acid, 1 U/mL isocitric dehydrogenase and 0.8 mg/mL HLM (human liver microsomes) in 100 mM potassium phosphate buffer (pH 7.4) at 37° C. on a number of 384-well plates. At several time points, a plate was removed from the incubator and the reaction was terminated with two incubation volumes of acetonitrile. The compound concentration in supernatant was measured by LC/MS/MS system. The intrinsic clearance value ($Cl_{int}$) was calculated using following equations:

$Cl_{int}$(μl/min/mg protein)=($k$×incubation volume)/Protein concentration $k$(min$^{-1}$)=−slope of ln(concentration vs. time)

Determination of $pA_2$ Values Against Capsaicin Stimulation $pA_2$ values of antagonists against the capsaicin agonist dose-response were determined using a $Ca^{2+}$ imaging assay with cells expressing high levels of human VR1 (for explanation of theory behind $pA_2$ determinations, see *A Pharmacological Primer: Theory, Applications, and Methods* 2$^{nd}$ edition by Terry P. Kenakin, pp. 102-108, Academic Press, New York, 2006). Cells that express high levels of VR1 were obtained by generation of a cell line from human keratinocytes with heterologous expression of VR1 under control of an inducible promoter. Specifically, cells expressing human VR1 under the control of the human cytomegalovirus immediate-early (CMV) promoter and two tetracycline operator 2 (TetO2) sites were made using the T-REx System (Invitrogen, Carlsbad, Calif., USA). Details and methods concerning this system are published (Hum. Gene Ther. 9, pp. 1939-1950, 1998; Annu. Rev. Microbiol. 48, pp. 345-369, 1994; Mol. Biol. 169, pp. 707-721, 1983). VR1 was subcloned into the T-REx System pcDNA5/TO vector (Invitrogen Cat# V1033-20) which was transfected into the T-REx System human keratinocyte cell line (Invitrogen Cat# R710-07) from which a stable cell line was established which express VR1 after induction by exposure to tetracycline or doxycycline (Hum. Gene Ther. 9, pp. 1939-1950, 1998; instructions that come with purchase of products noted above). Cells were maintained in a $CO_2$ incubator (5% $CO_2$) at 37° C. in culture medium containing DMEM with phenol red (Mediatech Cat #: 15-017-CV) supplemented with 10% heat-inactivated Fetal Bovine Serum, 5% Penicillin-streptomycin (Mediatech Cat #: 30-002-CI), 5% Glutamax® (L-Alanyl-L-Glutamine, Mediateach Cat #: 25-015-CI), 200 µg/ml hygromycin (Mediatech #:30-240-CR), 0.5 µg/ml blasticidin (Invitrogen #46-1120)).

For assay preparation, cells expressing human VR1 as described above were plated in 96-well plates (Becton Dickinson [BD] poly-D-lysine coated 96-well plates, cat#356692) at 55,000 cells per well in culture media (described above) that also contains 1 ug/ml doxycycline. Plated cells were then placed in an incubator (5% $CO_2$) and incubated for 20-26 hours at 37° C. Media was then aspirated from cells and 50 uL of dye-containing buffer (from Molecular Devices FLIPR Calcuim 4 Assay kit, cat#R8141) was added to each well. Cells were then left in the dark at room temperature for 1.5-2 hours. Cell plates were then placed in the FLIPR TETRA (Molecular Devices, CA, USA). Antagonists and capsaicin were added to each well using the liquid handling capability of the FLIPR TETRA. Antagonists in saline (130 mM NaCl, 17 g/L sucrose, 1.8 g/L glucose, 8.8 mM HEPES, 3 mM KCl, 0.60 mM MgCl, 1.0mM CaCl; adjust to pH 7.4 using 10N or 1N NaOH; 0.03% BSA added on the day of the experiment), or vehicle control in saline, were pre-inucbated at the desired final concentrations in the dark at room temperature for 2 or 30 minutes (please see Table 2 for preincubation time used) with cells already containing the above mentioned dye buffer. Then capsaicin plus the appropriate concentration of antagonist in saline was added at varying concentrations to achieve final concentrations covering the range of 17 pM-3 uM final capsaicin and the same final concentration of antagonist, or vehicle control, that was already in the well from the antagonist pre-incubation step described above. Changes in the fluorescence signal ($\lambda$ex=470-495 nm, $\lambda$em=515-575 nm) were monitored throughout the experiment before agonist addition and for at least 2 min after agonist addition (enough time for the fluorescence response to reach and then decline from the absolute maximum, agonist-induced signal attained). For each well, final relative fluorescence units (RFUs) were calculated as the difference between the maximum fluorescence signal obtained in the experiment after agonist addition and the signal level seen at baseline before agonist, but after antagonist, addition (the absolute minimum level of fluorescence signal observed in the 10 seconds prior to agonist addition). These final RFU values were plotted against the corresponding capsaicin concentrations to obtain dose response curves across the capsaicin dose range tested; one dose response curve for each concentration of antagonist tested and one for the capsaicin dose-response without any antagonist (vehicle control). Data was fit to an ideal curve utilizing the 4-parameter sigmoid curve-fit function in GraphPad Prism software (version 4, GraphPad Software, Inc., San Diego, Calif., USA) from which an $EC_{50}$ value was obtained. The dose ratio (DR) was then calculated for each concentration of antagonist tested as the ratio of the $EC_{50}$ value of the dose-response curve of capsaicin in the presence of a given concentration of antagonist divided by the $EC_{50}$ value of the dose-response curve of capsaicin without antagonist (vehicle control). For each antagonist, at least three concentrations were tested. Dose Ratio values were then used to make a standard Schild plot—log [antagonist concentration] plotted against log [DR-1], see Kenakin reference above for theoretical background and method. A linear regression curve-fit was then performed on these plotted points. If the linear regression provided an $R^2$ value $\geq$ 0.8 AND there are at least two concentrations of antagonist tested that provided a DR value greater than 1, then $pA_2$ values were calculated and reported as $pA_2$=Log(DR-1)–Log [antagonist] for the lowest concentration of antagonist tested for which (DR-1)>0 (Table 2). If these conditions were not met, then the antagonist was rerun in a $pA_2$ assay using different antagonist concentrations until the above conditions were met.

$pA_2$ values for Examples 1, 6 and 18 against the capsaicin agonist dose-response were determined in the assay described above and are presented in the following table.

TABLE 3

| Example No. | $pA_2$ | Pre- incubation (mins) |
|---|---|---|
| 1 | 8.76 | 2 |
| 6 | 8.73 | 2 |
| 18 | 8.28 | 30 |

Drug Substance

Pharmaceutically acceptable salts of the compounds of formula (I) include the acid addition and base salts thereof.

Suitable acid addition salts are formed from acids which form non-toxic salts. Examples include acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, EtOH. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:
(i) where the compound of formula (I) contains a carboxylic acid functionality (—COOH), an ester thereof, for example, replacement of the hydrogen with $(C_1-C_8)$alkyl;
(ii) where the compound of formula (I) contains an alcohol functionality (—OH), an ether thereof, for example, replacement of the hydrogen with $(C_1-C_6)$alkanoyloxymethyl; and
(iii) where the compound of formula (I) contains a primary or secondary amino functionality (—$NH_2$ or —NHR where R is not H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group, an aromatic moiety or a heteroaromatic ring including nitrogen of more than two, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, EtOH, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colorants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified controlled release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably. to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, EtOH, aqueous EtOH, or a suitable alternative agent for dispersing, solubilising, or extending release of the active, a propellant(s) as solvent and an optional surfactant, such as sorbitan trioleate, oleic acid, or an oligolactic acid.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 10 mg of the compound of formula (I). The overall daily dose will typically be in the range 1 µg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the compounds of the invention is typically in the range 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H₁ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid, (3R,4R,5R)-3-amino-4,5-dimethyl-octanoic acid, (2S)-2-Amino-4-ethyl-2-methylhexanoic acid and (2S)-2-aminomethyl-5-ethyl-heptanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-m ethyl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The invention claimed is:

1. A compound of the formula (I):

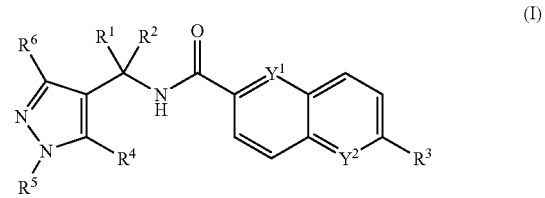

wherein
$Y^1$ and $Y^2$ are each independently N or CH; with the proviso that only one of $Y^1$ and $Y^2$ may be N;

$R^1$ and $R^2$ are each independently hydrogen, $(C_1-C_4)$alkyl, halo$(C_1-C_4)$alkyl, hydroxy$(C_1-C_4)$alkyl, or $(C_1-C_2)$alkoxy$(C_1-C_2)$alkyl; or $R^1$ and $R^2$, together with the carbon atom to which they are linked, can form a cyclopropyl group;

$R^3$ is $(C_1-C_4)$alkyl, $(C_1-C_4)$alkyl-cyclopropyl, $(C_1-C_2)$alkoxy$(C_1-C_4)$alkyl or hydroxy$(C_1-C_4)$alkyl, each optionally substituted by halo or halo$(C_1-C_2)$alkyl;

$R^4$ and $R^6$ are each independently hydrogen, halo, cyano, $(C_3-C_6)$cycloalkyl, $(C_1-C_6)$alkoxy or $(C_1-C_6)$alkyl, wherein $(C_1-C_6)$alkyl is optionally substituted with one or more substituents selected from halo, amino, cyano, hydroxy, $R^7R^8NC(O)$— and $R^7OC(O)$—;

$R^5$ is hydrogen, $(C_3-C_6)$cycloalkyl, or $(C_1-C_6)$alkyl, wherein $(C_1-C_6)$alkyl is optionally substituted with one or more substituents selected from halo, amino, cyano, hydroxy, $R^7R^8NC(O)$— or $R^7OC(O)$—;

with the proviso that at least one of $R^4$, $R^5$ and $R^6$ is not hydrogen; and, $R^7$ and $R^8$ are each independently hydrogen or $(C_1-C_4)$alkyl;

or a pharmaceutically acceptable salt thereof.

2. A compound according to claim 1, or a pharmaceutically acceptable salt thereof, wherein $Y^1$ is N and $Y^2$ is CH; or $Y^1$ is CH and $Y^2$ is N.

3. A compound according to claim 1, or a pharmaceutically acceptable salt thereof, wherein $Y^1$ is CH and $Y^2$ is CH.

4. A compound according to claim 1, or a pharmaceutically acceptable salt thereof, wherein $R^1$ and $R^2$ are each independently hydrogen, ethyl or methyl, wherein methyl and ethyl are optionally substituted with one or more fluoro atoms.

5. A compound according to claim 1, or a pharmaceutically acceptable salt thereof, wherein $R^1$ is hydrogen, ethyl or methyl and $R^2$ is hydrogen.

6. A compound according to claim 1, or a pharmaceutically acceptable salt thereof, wherein $R^3$ is 1-methylcylopropyl or $R^3$ is $(C_1-C_4)$alkyl, $(C_1-C_2)$alkoxy$(C_1-C_4)$alkyl or hydroxy$(C_1-C_4)$alkyl, each optionally substituted by halo or halo$(C_1-C_2)$alkyl.

7. A compound according to claim 1, or a pharmaceutically acceptable salt thereof, wherein $R^6$ is hydrogen or $(C_1-C_6)$alkyl.

8. A compound according to claim 1, or a pharmaceutically acceptable salt thereof, wherein $R^4$ is hydrogen, halo, cyano, $(C_1-C_6)$alkoxy or $(C_1-C_6)$alkyl, wherein $(C_1-C_6)$alkyl is optionally substituted with one or more substituents selected from halo and hydroxy.

9. A compound according to claim 1, or a pharmaceutically acceptable salt thereof, wherein $R^5$ is hydrogen, cyclopropyl, cyclobutyl or $(C_1-C_4)$alkyl, wherein $(C_1-C_4)$alkyl is optionally substituted with one or more substituents selected from halo, amino, cyano, hydroxy, $R^7R^8NC(O)$— and $R^7OC(O)$—.

10. A compound according to claim 1, said compound being selected from
- N-(1,5-dimethyl-1H-pyrazol-4-yl)ethyl)-2-(1,1,1-trifluoro-2-methylpropan-2-yl)quinoline-6-carboxamide;
- N-[(1,5-dimethyl-1H-pyrazol-4-yl)methyl]-2-(2,2,2-trifluoro-1,1-dimethylethyl)quinoline-6-carboxamide;
- N-(1-(5-cyano-1-methyl-1H-pyrazol-4-yl)ethyl)-2-(1,1,1-trifluoro-2-methylpropan-2-yl)quinoline-6-carboxamide;
- N-(1-(5-(hydroxymethyl)-1-methyl-1H-pyrazol-4-yl)ethyl)-2-(1,1,1-trifluoro-2-methylpropan-2-yl)quinoline-6-carboxamide;
- N-(1-(5-methyl-1-(2,2,2-trifluoroethyl)-1H-pyrazol-4-yl)ethyl)-2-(1,1,1-trifluoro-2-methylpropan-2-yl)quinoline-6-carboxamide;
- N-(1-(5-methyl-1-(2,2,2-trifluoroethyl)-1H-pyrazol-4-yl)ethyl)-2-(1,1,1-trifluoro-2-methylpropan-2-yl)quinoline-6-carboxamide;
- N-[1-(1,5-dimethyl-1H-pyrazol-4-yl)propyl]-2-(2,2,2-trifluoro-1,1-dimethylethyl)quinoline-6-carboxamide;
- N-[1-(5-methyl-1H-pyrazol-4-yl)ethyl]-2-(2,2,2-trifluoro-1,1-dimethylethyl)quinoline-6-carboxamide;
- 2-(5-methyl-4-(1-(2-(1,1,1-trifluoro-2-methylpropan-2-yl)quinoline-6-carboxamido)ethyl)-1H-pyrazol-1-yl)acetate;
- N-(1-(1-(2-hydroxyethyl)-5-methyl-1H-pyrazol-4-yl)ethyl)-2-(1,1,1-trifluoro-2-methylpropan-2-yl)quinoline-6-carboxamide;
- N-(1-(1-(2-hydroxy-2-methylpropyl)-5-methyl-1H-pyrazol-4-yl)ethyl)-2-(1,1,1-trifluoro-2-methylpropan-2-yl)quinoline-6-carboxamide;
- N-[1-(1,5-dimethyl-1H-pyrazol-4-yl)ethyl]-2-(1-methylcyclopropyl)quinoline-6-carboxamide;
- N-[1-(1,5-dimethyl-1H-pyrazol-4-yl)ethyl]-2-(2,2,2-trifluoro-1-hydroxy-1-methylethyl)quinoline-6-carboxamide;
- N-[(1-ethyl-5-methyl-1H-pyrazol-4-yl)methyl]-2-(2,2,2-trifluoro-1,1-dimethylethyl)quinoline-6-carboxamide;
- N-[1-(1-ethyl-5-methyl-1H-pyrazol-4-yl)ethyl]-2-(2,2,2-trifluoro-1,1-dimethylethyl)quinoline-6-carboxamide;
- N-(1-cyclobutyl-5-methyl-1H-pyrazol-4-yl)ethyl)-2-(2,2,2-trifluoro-1,1-dimethylpropan-2-yl)quinoline-6-carboxamide;
- N-(1-(5-chloro-1-methyl-1H-pyrazol-4-yl)ethyl)-2-(1,1,1-trifluoro-2-methylpropan-2-yl)quinoline-6-carboxamide;
- N-(1-(5-chloro-1-methyl-1H-pyrazol-4-yl)ethyl)-2-(trifluoromethyl)quinoline-6-carboxamide;
- N-(1-(1-ethyl-5-methyl-1H-pyrazol-4-yl)ethyl)-2-(1,1,1-trifluoro-2-methylpropan-2-yl)quinoline-6-carboxamide;
- N-(1-(1-methyl-5-(trifluoromethyl)-1H-pyrazol-4-yl)ethyl)-2-(trifluoromethyl)quinoline-6-carboxamide;
- N-(1-(1-methyl-5-(trifluoromethyl)-1H-pyrazol-4-yl)ethyl)-2-(1,1,1-trifluoro-2-methylpropan-2-yl)quinoline-6-carboxamide;
- N-(1-(1,5-dimethyl-1H-pyrazol-4-yl)ethyl)-2-(trifluoromethyl)quinoline-6-carboxamide;
- 6-tert-butyl-N-[1-(1,5-dimethyl-1H-pyrazol-4-yl)ethyl-]-2-naphthamide;
- 6-tert-butyl-N-[(3,5-dimethyl-1H-pyrazol-4-yl)methyl]-2-naphthamide;
- 6-tert-butyl-N-[(1,3-dimethyl-1H-pyrazol-4-yl)methyl]-2-naphthamide; 6-tert-butyl-N-[(1,5-dimethyl-1H-pyrazol-4-yl)methyl]-2-naphthamide;
- 6-tert-butyl-N-(1-(1,5-dimethyl-1H-pyrazol-4-yl)propyl)-2-naphthamide;
- N-(1-(1,5-dimethyl-1H-pyrazol-4-yl)ethyl)-6-(trifluoromethyl)-2-naphthamide;
- N-[1-(1,5-dimethyl-1H-pyrazol-4-yl)ethyl]-6-(1-methylcyclopropyl)-2-naphthamide;
- N-[1-(1,5-dimethyl-1H-pyrazol-4-yl)ethyl]-6-(2,2,2-trifluoro-1-hydroxy-1-methylethyl)-2-naphthamide;
- N-[1-(1,5-dimethyl-1H-pyrazol-4-yl)ethyl]-6-(2,2,2-trifluoro-1-methoxy-1-methylethyl)-2-naphthamide;
- 6-tert-butyl-N-[(1,5-dimethyl-1H-pyrazol-4-yl)methyl]quinoline-2-carboxamide;
- 6-tert-butyl-N-((1,3,5-trimethyl-1H-pyrazol-4-yl)methyl)-2-naphthamide;
- 6-tert-butyl-N-[(1-methyl-1H-pyrazol-4-yl)methyl]-2-naphthamide;
- N-[1-(1,5-dimethyl-1H-pyrazol-4-yl)ethyl]-6-(1-hydroxy-1-methylethyl)-2-naphthamide;
- (S)—N-(1-(5-chloro-1-methyl-1H-pyrazol-4-ylethyl)-2-(2,2,2-trifluoro-1,1-dimethylethyl)quinoline-6-carboxamide;
- (R)—N-(1-(5-chloro-1-methyl-1H-pyrazol-4-yl)ethyl)-2-(2,2,2-trifluoro-1,1-dimethylethyl)quinoline-6-carboxamide;
- (S)—N-(1-(5-chloro-1-methyl-1H-pyrazol-4-yl)ethyl)-2-(trifluoromethyl)quinoline-6-carboxamide;
- (R)—N-(1-(5-chloro-1-methyl-1H-pyrazol-4-yl)ethyl)-2-(trifluoromethyl)quinoline-6-carboxamide;
- (S)—N-(1-(1-methyl-5-(trifluoromethyl)-1H-pyrazol-4-yl)ethyl)-2-(trifluoromethyl)quinoline-6-carboxamide;
- (R)—N-(1-(1-methyl-5-(trifluoromethyl)-1H-pyrazol-4-yl)ethyl)-2-(trifluoromethyl)quinoline-6-carboxamide
- (S)—N-(1-(1-methyl-5-(trifluoromethyl)-1H-pyrazol-4-ylethyl)-2-(1,1,1-trifluoro-2-methylpropan-2-yl)quinoline-6-carboxamide;
- (R)—N-(1-(1-methyl-5-(trifluoromethyl)-1H-pyrazol-4-yl)ethyl)-2-(1,1,1-trifluoro-2-methylpropan-2-yl)quinoline-6-carboxamide;
- N-[(1R)-(1,5-dimethyl-1H-pyrazol-4-yl)ethyl)]-2-(2,2,2-trifluoro-1,1-dimethylethyl)quinoline-6-carboxamide;
- N-[(1S)-(1,5-dimethyl-1H-pyrazol-4-yl)ethyl)]-2-(2,2,2-trifluoro-1,1-dimethylethyl)quinoline-6-carboxamide; and
- N-(1-(5-chloro-1-methyl-1H-pyrazol-4-ylethyl)-2-(pentafluoroethyl)quinoline-6-carboxamide;

and the pharmaceutically acceptable salts thereof.

11. A pharmaceutical composition including a compound of the formula (I), or a pharmaceutically acceptable salt thereof, as defined in claim 1, together with a pharmaceutically acceptable excipient.

12. N-[1-(5-methyl-1H-pyrazol-4-yl)ethyl]-2-(2,2,2-trifluoro-1,1-dimethylethyl)quinoline-6-carboxamide.

* * * * *